US010703735B2

(12) United States Patent
Di Lucrezia et al.

(10) Patent No.: US 10,703,735 B2
(45) Date of Patent: Jul. 7, 2020

(54) 4-PHENYL-COUMARIN DERIVATIVES, PROCESSES FOR THEIR PREPARATION AND USES THEREOF FOR THE TREATMENT OF CANCER

(71) Applicants: Lead Discovery Center GmbH, Dortmund (DE); Max Planck Gesellschaft zur Förderung der Wissenschaften e. V., München (DE)

(72) Inventors: Raffaella Di Lucrezia, Wuppertal (DE); Tim Bergbrede, Dortmund (DE); Peter Nussbaumer, Dortmund (DE); Uwe Koch, Dortmund (DE); Bert Klebl, Dortmund (DE); Axel Choidas, Herdecke (DE); Anke Unger, Dortmund (DE); Nils-Göran Larsson, Sollentuna (SE); Maria Falkenberg-Gustafsson, Mölndal (SE); Claes M. Gustafsson, Mölndal (SE)

(73) Assignees: Lead Discovery Center GmbH, Dortmund (DE); Max Planck Gesellschaft zur Förderung der Wissenschaften e. V., München (DE)

( * ) Notice: Subject to any disclaimer, the term of this patent is extended or adjusted under 35 U.S.C. 154(b) by 0 days.

(21) Appl. No.: 16/519,856

(22) Filed: Jul. 23, 2019

(65) Prior Publication Data
US 2020/0031794 A1 Jan. 30, 2020

(30) Foreign Application Priority Data

Jul. 25, 2018 (EP) ..................................... 18185514

(51) Int. Cl.
C07D 311/04 (2006.01)
C07D 311/54 (2006.01)
C07D 413/12 (2006.01)
C07D 407/14 (2006.01)
C07D 407/12 (2006.01)

(52) U.S. Cl.
CPC .......... *C07D 311/54* (2013.01); *C07D 407/12* (2013.01); *C07D 407/14* (2013.01); *C07D 413/12* (2013.01)

(58) Field of Classification Search
CPC .................................................. C07D 311/04
USPC ....................................................... 549/283
See application file for complete search history.

(56) References Cited

U.S. PATENT DOCUMENTS

| 3,243,441 A * | 3/1966 | Ritter .................... C07D 311/16 549/289 |
| 3,243,442 A | 3/1966 | Ritter et al. |
| 3,282,938 A * | 11/1966 | Hanau .................. C07D 311/16 544/151 |
| 8,642,660 B2 * | 2/2014 | Goldfarb .............. A61K 31/122 514/641 |

FOREIGN PATENT DOCUMENTS

| CN | 106674176 A | 5/2017 |
| JP | H02191269 A | 7/1990 |
| JP | 2876129 | * 11/1999 |
| WO | 2008054475 A2 | 5/2008 |
| WO | 2013123071 A1 | 8/2013 |
| WO | 2016146583 A1 | 9/2016 |
| WO | 2016193231 A1 | 12/2016 |

OTHER PUBLICATIONS

Garazd et al., Chemistry of Natural Compounds (Translation of Khimiya Prirodnykh Soedinenii) (2000), Volume Date 1999, 35(4), 415-419.*
Henriksen et al., Bioorganic & Medicinal Chemistry (2010), 18(14), 5148-5156.*
European Search Report for European Application No. 19188009.5, dated Dec. 11, 2019 (9 pages).
Halawa et al., "Synthesis, reactions, antioxidant and anticancer evaluation of some novel coumarin derivatives using ethyl 2-(2-oxo-4-phenyl-2H-chromen-7-yloxy) acetate as a starting material", European Journal of Chemistry, vol. 5, Isse. 1, pp. 111-121, 2014, DOI: 10.5155/eurjchem.5.1.111-121.860, (11 pages).
Ananthan et al., "High-throughput screening for inhibitors of Mycobacterium tuberculosis H37Rv", Tuberculosis, vol. 89, pp. 334-353, 2009, doi:10.1016/j.tube.2009.05.008, (20 pages).
E-Space English Language Abstract for CN 106674176.
E-Space English Language Abstract for JP H02191269.
Database WPI Week 199037, Thomson Scientific, London, GB, 1990, XP-002788041, (2 Pages).
Brecht et al., "Mechanistic insights into selective killing of OXPHOS-dependent cancer cells by arctigenin", Toxicology in Vitro, No. 40, pp. 55-65, 2017, (11 pages).
Bubner et al., "Use of real-time PCR for determining copy number and zygosity in transgenic plants", Plant Cell Rep, No. 23, pp. 263-271, Sep. 11, 2004, DOI 10.1007/s00299-004-0859-y, (9 pages).
Caro et al., "Metabolic Signatures Uncover Distinct Targets in Molecular Subsets of Diffuse Large B Cell Lymphoma", Cancer Cell Article 22, pp. 547-560, Oct. 16, 2012, (14 pages).
Carroll et al., "Inhibition of Hepatitis C Virus RNA Replication by 2′-Modified Nucleoside Analogs*", The Journal of Biological Chemistry, vol. 278, No. 14, pp. 11979-11984, Jan. 27, 2003, (7 pages).
Denise et al., "5-Fluorouracil resistant colon cancer cells are addicted to OXPHOS to survive and enhance stem-like traits", Oncotarget, vol. 6, No. 39, pp. 41706-41721, Oct. 21, 2015, (16 pages).

(Continued)

*Primary Examiner* — Niloofar Rahmani
(74) *Attorney, Agent, or Firm* — Kagan Binder, PLLC

(57) ABSTRACT

The invention provides novel 4-phenyl-coumarin derivatives, processes for their preparation and uses thereof as specific mitochondrial RNA polymerase inhibitors for the treatment of cancer.

14 Claims, No Drawings

(56) References Cited

OTHER PUBLICATIONS

Dörr et al., "Synthetic lethal metabolic targeting of cellular senescence in cancer therapy", Research Letter, Nature, vol. 501, pp. 421-428, Sep. 13, 2019, doi:10.1038/nature12437, (8 pages).
Falkenberg et al., "Mitochondrial transcription factors B1 and B2 activate transcription of human mtDNA", Nature Genetics, vol. 31, pp. 289-294, Jun. 17, 2002, doi:10.1038/ng909, (6 pages).
Fulda et al., "Targeting mitochondria for cancer therapy", Nature Reviews, Drug Discovery, vol. 9, pp. 447-480, Jun. 2010, doi:10.1038/nrd3137, (27 pages).
Gosselin et al., "A Practical Synthesis of 5-Lipoxygenase Inhibitor MK-0633", JOC Article, American Chemical Society, No. 75, pp. 4154-4160, May 20, 2010, DOI: 10.1021/jo100561u, (7 pages).
Haq et al., "Oncogenic BRAF Regulates Oxidative Metabolism via PGC1a and MITF", Cancer Cell Article 23, pp. 302-315, Mar. 18, 2013, (14 pages).
Haynes et al., "Occurrence of Pharmaceutically Acceptable Anions and Cations in the Cambridge Structural Database", Journal of Pharmaceutical Sciences, vol. 94, No. 10, pp. 2111-2120, Oct. 2005, DOI 10.1002/jps.20441, (10 pages).
Heid et al., "Real Time Quantitative PCR", Cold Spring Harbor Laboratory Press ISSN 1054-9803/96, pp. 985-994, Jul. 29, 1996, doi:10.1101/gr.6.10.986, (10 pages).
Hsu et al., "Cancer Cell Metabolism: Warburg and Beyond", Cell 134, pp. 703-707, Sep. 5, 2008, DOI 10.1016/j.cell.2008.08.021, (5 pages).
Klomp et al., "Birt-Hogg-Dubé renal tumors are genetically distinct from other renal neoplasias and are associated with up-regulation of mitochondrial gene expression", BMC Medical Genomics, 3:59, pp. 1-12, 2010, doi:10.1186/1755-8794-3-59, (12 pages).
Leonetti e a., "Design, Synthesis, and 3D QSAR of Novel Potent and Selective Aromatase Inhibitors", Journal of Medicinal Chemistry, vol. 47, No. 27, pp. 6792-6803, Dec. 7, 2004, (12 pages).
Ling et al., "Combination of metformin and sorafenib suppresses proliferation and induces autophagy of hepatocellular carcinoma via targeting the mTOR pathway", International Journal of Oncology, 50: pp. 297-309, Dec. 9, 2016 DOI: 10.3892/ijo.2016.3799, (13 pages).
Mitsunobu et al., "Preparation of Esters of Carboxylic and Phosphoric Acid via Quaternary Phosphonium Salts", Bulletin of the Chemical Society of Japan, vol. 40, No. 10, pp. 2380-2382, 1967, (3 pages).
Nadji et al., "Immunohistochemistry of Estrogen and Progesterone Receptors Reconsidered", American Journal of Clinical Pathology, vol. 123, pp. 21-27, 2005, DOI: 10.1309/4WV79N2GHJ3X1841, (7 pages).
Pelicano et al., "Glycolysis inhibition for anticancer treatment", Nature Publishing Group, Oncogene, vol. 25, pp. 4633-4646, 2006, (14 pages).
Pelicano et al., "Mitochondrial dysfunction in some triple-negative breast cancer cell lines: role of mTOR pathway and therapeutic potential", Breast Cancer Research 16, Article 434, pp. 1-16, 2014, doi:10.1186/s13058-014-0434-6, (16 pages).
Posse et al., "TEFM is a potent stimulator of mitochondrial transcription elongation in vitro", Nucleic Acids Research, vol. 43, No. 5, pp. 2615-2624, Feb. 17, 2015, doi: 10.1093/nar/gkv105, (10 pages).
Rodrigues et al., "Enhanced OXPHOS, glutaminolysis and β-oxidation constitute the metastatic phenotype of melanoma cells", The Biochemical Journal, 473, pp. 703-715, 2016, doi:10.1042/BJ20150645, (13 pages).
Rodriguez-Enriquez et al., "Mitochondrial free fatty acid -oxidation supports oxidativephosphorylation and proliferation in cancer cells", The International Journal of Biochemistry & Cell Biology, 4647, pp. 1-13, Jun. 8, 2015, (13 pages).
Roesch et al., "Overcoming intrinsic multi-drug resistance in melanoma by blocking the mitochondrial respiratory chain of slow-cycling JARID1Bhigh cells", Cancer Cell, vol. 23, Isse. 6, pp. 811-825, Jun. 10, 2013, doi:10.1016/j.ccr.2013.05.003, (28 pages).
Salem et al., "Two-compartment tumor metabolism Autophagy in the tumor microenvironment and oxidative mitochondrial metabolism (OXPHOS) in cancer cells", Cell Cycle, vol. 11, Isse. 13, pp. 2545-2556, Jul. 1, 2012, (12 pages).
Sanchez-Alvarez et al., "Mitochondrial dysfunction in breast cancer cells prevents tumor growth Understanding chemoprevention with metformin", Cell Cycle, vol. 12, Isse. 1, pp. 172-182, Jan. 1, 2013, (11 pages).
Scarpulla, "Transcriptional paradigms in mammalian mitochondrial biogenesis and function", Physiological Reviews, 88, pp. 611-638, Mar. 31, 2008, doi:10.1152/physrev.00025.2007, (28 pages).
Scatena et al., "Glycolytic enzyme inhibitors in cancer treatment", Expert Opinion on Investigational Drugs, vol. 17, Isse. 10, pp. 1533-1545, 2008, doi:10.1517/13543780802411053, (13 pages).
Schöckel et al., "Targeting mitochondrial complex I using BAY 87-2243 reduces melanoma tumor growth", Cancer & Metabolism 3, article 11, pp. 2-16, 2015, DOI 10.1186/s40170-015-0138-0, (16 pages).
Sharma et al., "Cyclohexyl iodide promoted approach for coumarin analog synthesis using small scaffold", Mol Divers 17, pp. 651-659, 2013, DOI 10.1007/s11030-013-9461-y, (9 pages).
Siegel et al., "Cancer Statistics, 2016", CA Cancer Journal, vol. 66, No. 1, pp. 7-30, 2016, doi: 10.3322/caac.21332, (24 pages).
Tisdale, "Cachexia in Cancer Patients", Nature Reviews, vol. 2, pp. 862-871, Nov. 2002, doi: 10.1038/nrg927, (10 pages).
Vander Heiden et al., "Understanding the Warburg Effect: The Metabolic Requirements of Cell Proliferation", Science, vol. 324, Isse. 5930, pp. 1029-1033, May 22, 2009, DOI: 10.1126/science.1160809, (12 pages).
Walters et al., "Designing Screens:How to Make Your Hits a Hit", Nature Reviews, vol. 2, pp. 259-266, Apr. 2003, (8 pages).
Wanrooij et al., "The human mitochondrial replication fork in health and disease", Biochimica et Biophysica Acta, vol. 1797, Isse. 8, pp. 1378-1388, 2010, doi:10.1016/j.bbabio.2010.04.015, (11 pages).
Weinberg et al., "Targeting mitochondria metabolism for cancer therapy", Nature Chemical Biology, vol. 11, pp. 9-15, Jan. 2015, doi: 10.1038/nchembio.1712, (7 pages).
Whitaker-Menezes et al., "Evidence for a stromal-epithelial "lactate shuttle" in human tumors", Cell Cycle, vol. 10, Isse. 11, pp. 1772-1783, Jun. 1, 2011, (12 pages).
Yeung et al., "The identification of mitochondrial DNA variants in glioblastoma multiforme", Acta Neuropathologica Communications 2, Article 1, pp. 1-21, 2014, doi:10.1186/2051-5960-2-1, (21 pages).
Ariaans et al., "Anti-tumor effects of everolimus and metformin are complementary and glucose-dependent in breast cancer cells", BMC Cancer, vol. 17, Article 232, pp. 1-13, 2017, DOI 10.1186/s12885-017-3230-8, (13 pages).
Arnold et al., "Human mitochondrial RNA polymerase: Structure-function, mechanism and inhibition" Biochimica et Biophysica Acta, vol. 1819, pp. 948-960, 2012, doi:10.1016/j.bbagrm.2012.04.002, (13 pages).
Behera et al., "Progesterone stimulates mitochondrial activity with subsequent inhibition of apoptosis in MCF-10A benign breast epithelial cells", Am J Physiol Endocrinol Metab, vol. 297, pp. E1089-E1096, 2009, doi:10.1152/ajpendo.00209.2009, (8 pages).
Bhat et al., "The mTOR Pathway in Hepatic Malignancies", Hepatology, vol. 58, No. 2, pp. 810-818, 2013, (9 pages).
Bralha et al., "Targeting mitochondrial RNA polymerase in acute myeloid leukemia", Oncotarget, vol. 6, No. 35, pp. 37216-37228, Oct. 15, 2015, (13 pages).

* cited by examiner

4-PHENYL-COUMARIN DERIVATIVES, PROCESSES FOR THEIR PREPARATION AND USES THEREOF FOR THE TREATMENT OF CANCER

CROSS-REFERENCE TO RELATED APPLICATIONS

This application claims priority to European Application No. 18185514.9, filed Jul. 25, 2018 and titled "4-PHENYL-COUMARIN DERIVATIVES, PROCESSES FOR THEIR PREPARATION AND USES THEREOF FOR THE TREATMENT OF CANCER," which is incorporated herein by reference in its entirety.

FIELD OF THE INVENTION

The present invention relates to compounds of the general formula (I)

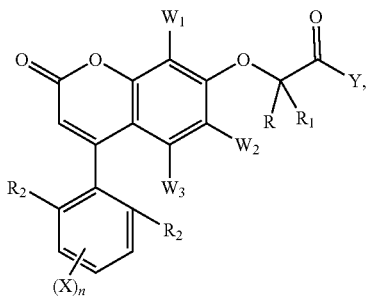

wherein R, $R_1$, $R_2$, n, X, Y, $W_1$, $W_2$, and $W_3$ have the designations cited below, or a pharmaceutically or veterinary acceptable salt, hydrate or solvate thereof, and to processes for the preparation of compounds of the general formula (I) or a pharmaceutically or veterinary acceptable salt, hydrate or solvate thereof. The invention also relates to compounds of the general formula (I) or a pharmaceutically or veterinary acceptable salt, hydrate or solvate thereof for use as a medicament. Further, the invention relates to compounds of the general formula (I) or a pharmaceutically or veterinary acceptable salt, hydrate or solvate thereof for use in the treatment of cancer. Moreover, the invention relates to compounds of the general formula (I) or a pharmaceutically or veterinary acceptable salt, hydrate or solvate thereof for treating cancer in simultaneous, alternating or subsequent combination with another cancer therapy.

BACKGROUND OF THE INVENTION

Despite enormous research efforts during the last decades and advanced cancer treatments, cancer remains a major public health problem worldwide and is the second leading cause of death in the United States. In the US population, incidence and death rates are even increasing for several cancer types, including liver and pancreas—two of the most fatal cancers (Siegel et al. 2016). Thus, there is still an urgent need to obtain additional and improved treatment options for fighting cancer besides the established chemotherapies, radiation and upcoming immunotherapies.

Interfering with the cancer metabolism is another principle to tackle tumor growth. In contrast to normal differentiated cells, which rely primarily on mitochondrial oxidative phosphorylation to generate energy, most cancer cells instead rely on aerobic glycolysis, a phenomenon termed "the Warburg effect" (Vander Heiden et al. 2009). Aerobic glycolysis in the cytoplasm leads to pyruvate generated from glucose, which is not transported into mitochondria for total oxidation for yielding more energy but is converted to lactate, originally described by Warburg (Hsu et al. 2008). Lactate is transferred to the liver, where the carbon skeleton is used to synthesize glucose known as the "neoplastic or pathological Cori cycle" contributing to the clinical metabolic state of Cachexia, a condition existing in neoplastic patients who suffer massive loss of normal body mass as the neoplasm continues its growth (Tisdale 2002). Consequently, inhibiting aerobic glycolysis (Warburg effect) and/or neoplastic anabolism (pathological Cori cycle) may be another effective way to interfere with cancer metabolism and effectively treat cancer patients. The inhibition of glycolysis in connection with the Warburg effect for cancer treatment has been described by Pelicano, H. et al. (2006) and Scatena et al. (2008).

However, the relevance of mitochondrial respiration in tumors is varied depending on tumor type. An oxidative class of tumors and tumors with dual capacity for glycolytic and oxidative metabolism is evident and the importance of mitochondria in tumor cell survival and proliferation, including utilization of alternative oxidizable substrates such as glutamine and fatty acids, has been increasingly appreciated. The diversity of carbon substrate utilization pathways in tumors is indicative of metabolic heterogeneity that may not only be relevant across different types of cancer but also manifest within a group of tumors that otherwise share a common diagnosis (Caro et al. 2012). Accordingly, tumors show heterogeneity in fuel utilization even within the same disease entity with some having a significant mitochondrial component, marked by elevated oxidative phosphorylation (OXPHOS), increased contribution of mitochondria to total cellular energy budget, greater incorporation of fatty acid- and glucose-derived carbons into the TCA cycle, and increased lipogenesis from these carbon substrates (Caro et al. 2012).

Indeed, recent evidence supports the hypothesis that acquired resistance to therapy is accompanied by a metabolic shift from aerobic glycolysis toward respiratory metabolism, suggesting that metabolic plasticity can have a role in survival of cells responsible for tumor relapse, suggesting that metabolic plasticity can have a role in survival of cells responsible for tumor relapse. For example, it has been observed that several drug-resistant tumor cells show a higher respiratory activity than parental cells. The metabolic adaptation allows OXPHOS-addicted cancer cells to easily survive drug treatments, but leaves cells susceptible to inhibitors of OXPHOS (Denise et al. 2015).

Cancer cell mitochondria are structurally and functionally different from their normal counterparts. Moreover, tumor cells exhibit an extensive metabolic reprogramming that renders them more susceptible to mitochondrial perturbations than non-immortalized cells. Based on these premises, mitochondrially-targeted agents emerge as a means to selectively target tumors. The correction of cancer-associated mitochondrial dysfunctions and the (re)activation of cell death programs by pharmacological agents that induce or facilitate mitochondrial membrane permeabilization represent attractive strategies for cancer therapy. Further, autophagy in the tumor stroma and oxidative mitochondrial metabolism (OXPHOS) in cancer cells can both dramatically promote tumor growth, independently of tumor angiogenesis (Salem et al. 2012) and that cancer-associated fibroblasts undergo aerobic glycolysis, thereby producing lactate, which is utilized as a metabolic substrate by adjacent cancer cells. In this model, "energy transfer" or "metabolic-coupling" between the tumor stroma and epithelial cancer cells "fuels" tumor growth and metastasis, via oxidative mitochondrial metabolism in anabolic cancer cells, the "reverse Warburg effect" (Whitaker-Menezes et al. 2011).

Accordingly, these findings provide a rationale and for novel strategies for anti-cancer therapies by employing inhibitors of OXPHOS and mitochondrial functions. Mitochondrial targeted anti-cancer drugs are reviewed by Fulda et al. (2010) and Weinberg and Chandel (2015) including inhibitors of mitochondrial complex 1, inhibitors of the electron transfer chain (ETC) complex, inhibitors of mitochondrial ribosomal machinery, inhibitors of the translation of ETC subunits, inhibitors of mitochondrial chaperone proteins, inhibitors of glutaminases, aminotransferases or glutamate dehydrogenases, short term inhibition of autophagy, mitochondrial-targeted antioxidants.

WO 2008/054475 A2 describes coumarin derivatives as inhibitors of neuraminidase for use in reducing or inhibiting biofilm formation for non-medical use.

Recently, mitochondrial RNA polymerase (POLRMT, also known as h-mtRNAP) has been proposed as a new target in acute myeloid leukemia (Bralha et al. 2015). POLRMT is responsible for the transcription of the 13 subunits of the OXPHOS complexes, two rRNAs and 22 tRNAs required for mitochondrial translation and acts as the RNA primase for mitochondrial DNA replication (Scarpulla 2008, Wanrooij et al. 2010). Therefore, this enzyme is of fundamental importance for both expression and replication of the human mitochondrial genome (Arnold et al. 2012).

A number of nucleoside analogues used as antiviral agents to target viral RNA polymerases demonstrate off-target inhibition of POLRMT (Arnold et al. 2012); POLRMT is distantly related to bacteriophage T7 class of single-subunit RNAPs. The finding that treatment with 2-C-methyladenosine, identified as an inhibitor of the RNA-dependent RNA polymerase of hepatitis C virus (Carroll et al. 2003), triggers the death of AML cells allegedly through rather unspecific inhibition of mitochondrial transcription confirms this rational (Bralha et al. 2015).

Thus, there is a need for alternative novel compounds, which specifically inhibit POLRMT and are suitable for use as a medicament. In particular, a need exists for novel compounds that can be used in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer. Furthermore, POLRMT inhibitors are of interest, which can be used in a method for treating cancer in simultaneous, alternating or subsequent combination with another cancer therapy.

Accordingly, the present invention provides specific POLRMT inhibitors for the treatment of cancer.

SUMMARY OF THE INVENTION

The present invention, in one aspect, relates to a compound of the general formula (I)

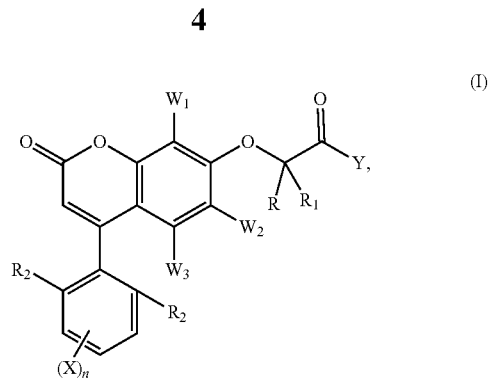

wherein
R is —H or —$C_1$-$C_4$-alkyl;
$R_1$ is —H or -methyl;
$R_2$ is —H;
n=0, 1 or 2;
X is -halogen, —$C_1$-$C_4$-alkyl, —OMe or —CN, with n=1 or 2;
Y is —$NR_3R_4$ with
$R_3$ is —H, or —$C_1$-$C_4$-alkyl, and
$R_4$ is —H, —$C_1$-$C_4$-alkyl or —$C_3$-$C_8$-cycloalkyl;
an unsubstituted or substituted pyridine residue;
an unsubstituted or substituted pyridinylmethyl residue;
an unsubstituted or substituted morpholinylethyl residue;
an unsubstituted or substituted furanylmethyl residue;
an unsubstituted or substituted phenyl residue;
an unsubstituted or substituted benzyl residue;
an unsubstituted or substituted phenethyl residue;
the group

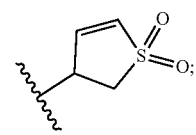 [SMILES: *C1C=CS(=O)(=O)C1]

or
the group

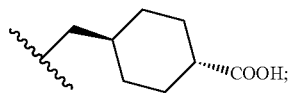 [SMILES: *C[C@H]1CC[C@H](C(=O)O)CC1]

or
Y is —$NR_3R_4$ with N, $R_3$ and $R_4$ forming an unsubstituted or substituted 5- or 6-membered saturated heterocycle,

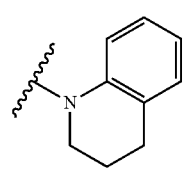 [SMILES: *N1CCCc2ccccc21]

or
Y is —$OR_{11}$, with $R_{11}$ is —H or —$C_1$-$C_4$-alkyl, phenyl, benzyl or 2-ethoxyethyl; and $W_1$, $W_2$, and $W_3$ are identical or different, and are —H, -halogen, or —$C_1$-$C_4$-alkyl;

or a pharmaceutically or veterinary acceptable salt, hydrate or solvate thereof for use as a medicament.

In one embodiment, the invention relates to the compound for use as defined above, wherein
R is —H, -methyl or -ethyl;
$R_1$ is —H;
$R_2$ is —H;
n=0 or 1, preferably n=0;
X is -halogen, —$C_1$-$C_4$-alkyl, —OMe or —CN, with n=1;
Y is —$NR_3R_4$ with
$R_3$ is —H, or —$C_1$-$C_4$-alkyl, preferably —H or -methyl, and
$R_4$ is —H, —$C_1$-$C_4$-alkyl or —$C_3$-$C_8$-cycloalkyl;
an unsubstituted or substituted pyridine residue;
an unsubstituted or substituted pyridinylmethyl residue;
an unsubstituted or substituted morpholinylethyl residue;
an unsubstituted or substituted furanylmethyl residue;
an unsubstituted or substituted phenyl residue;
an unsubstituted or substituted benzyl residue;
an unsubstituted or substituted phenethyl residue;
the group

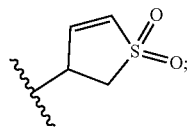 [SMILES: *C1C=CS(=O)(=O)C1]

or
the group

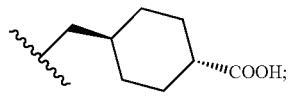 [SMILES: *C[C@H]1CC[C@H](C(=O)O)CC1]

or
Y is —$NR_3R_4$ with N, $R_3$ and $R_4$ forming an unsubstituted or substituted 5- or 6-membered saturated heterocycle,

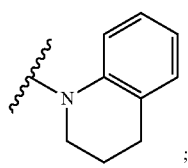

or
Y is —$OR_{11}$, with $R_{11}$ is —H or —$C_1$-$C_4$-alkyl, phenyl, benzyl or 2-ethoxyethyl; and
$W_1$, $W_2$, and $W_3$ are identical or different, and are —H, -halogen, or —$C_1$-$C_4$-alkyl.

In another embodiment, the invention relates to the compound for use as defined above, wherein
R is —H or -methyl;
$R_1$ is —H; and
$W_1$, $W_2$, and $W_3$ are identical or different, and are —H or —Cl.

In another embodiment, the invention relates to the compound for use as defined above, wherein
$W_1$, $W_2$, and $W_3$ are identical and are —H.

In another embodiment, the invention relates to the compound for use as defined above, wherein
$W_1$ and $W_3$ are identical and are —H; and $W_2$ is —Cl.

In another embodiment, the invention relates to the compound for use as defined above, wherein
R is -methyl; and
$R_1$ is —H.

In another embodiment, the invention relates to the compound for use as defined above, wherein
R is —H and
$R_1$ is —H.

In another embodiment, the invention relates to the compound for use as defined above, wherein
n=1; and
X is -halogen.

In another embodiment, the invention relates to the compound for use as defined above, wherein
n=0, 1 or 2, preferably 0, or
X is -halogen, or —CN, with n=1 or 2;
Y is —$NR_3R_4$ with
$R_3$ is —H, or —$C_1$-$C_4$-alkyl, and
$R_4$ is —$C_1$-$C_4$-alkyl or —$C_3$-$C_6$-cycloalkyl; or
an unsubstituted or substituted pyridine residue; or
an unsubstituted or substituted phenyl residue;
Y is —$NR_3R_4$ with N, $R_3$ and $R_4$ forming an unsubstituted or substituted 5- or 6-membered saturated heterocycle; or
Y is —$OR_{11}$, with $R_{11}$ is —H or —$C_1$-$C_4$-alkyl.

In another aspect, the invention relates to a compound of the general formula (I) as defined herein for use in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

In another aspect, the invention relates to a compound of the general formula (I) as defined herein for use in a method for treating cancer in simultaneous, alternating or subsequent combination with another cancer therapy, preferably selected from chemotherapy, immunotherapy, hormone therapy, stem cell transplantation therapy, radiation therapy or surgery.

In another aspect, the invention relates to compounds of the general formula (I)

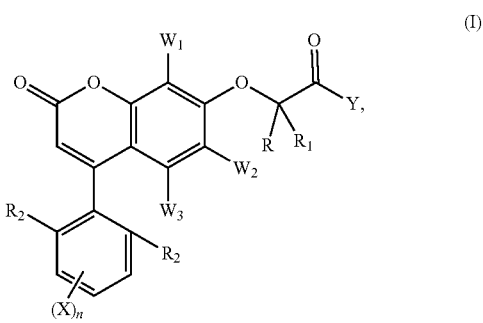

wherein
R is —H or —$C_1$-$C_4$-alkyl;
$R_1$ is —H or -methyl;

$R_2$ is —H;
n=0, 1 or 2;
X is -halogen, —$C_1$-$C_4$-alkyl, —OMe or —CN, with n=1 or 2;
Y is —$NR_3R_4$ with
$R_3$ is —H, or —$C_1$-$C_4$-alkyl, and
$R_4$ is —H, —$C_1$-$C_4$-alkyl or —$C_3$-$C_8$-cycloalkyl;
an unsubstituted or substituted pyridine residue;
an unsubstituted or substituted pyridinylmethyl residue;
an unsubstituted or substituted morpholinylethyl residue;
an unsubstituted or substituted furanylmethyl residue;
an unsubstituted or substituted phenyl residue;
an unsubstituted or substituted benzyl residue;
an unsubstituted or substituted phenethyl residue;
the group

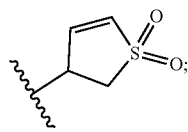 [SMILES: *C1C=CS(=O)(=O)C1]

or
the group

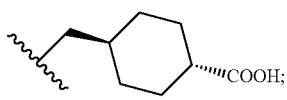 [SMILES: *C[C@H]1CC[C@H](C(=O)O)CC1]

or
Y is —$NR_3R_4$ with N, $R_3$ and $R_4$ forming an unsubstituted or substituted 5- or 6-membered saturated heterocycle,

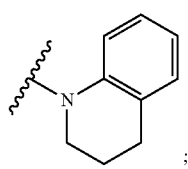

or
Y is —$OR_{11}$, with $R_{11}$ is —H or —$C_1$-$C_4$-alkyl, phenyl, benzyl or 2-ethoxyethyl; and
$W_1$, $W_2$, and $W_3$ are identical or different, and are —H, -halogen, or —$C_1$-$C_4$-alkyl;
or a pharmaceutically or veterinary acceptable salt, hydrate or solvate thereof.
In one embodiment, the invention relates to compounds of the general formula (I),
wherein
R is —H, -methyl or -ethyl;
$R_1$ is —H;
$R_2$ is —H;
n=0 or 1, preferably n=0;
X is -halogen, —$C_1$-$C_4$-alkyl, —OMe or —CN, with n=1;
Y is —$NR_3R_4$ with
$R_3$ is —H, or —$C_1$-$C_4$-alkyl, preferably —H or -methyl, and
$R_4$ is —H, —$C_1$-$C_4$-alkyl or —$C_3$-$C_8$-cycloalkyl;
an unsubstituted or substituted pyridine residue;
an unsubstituted or substituted pyridinylmethyl residue;
an unsubstituted or substituted morpholinylethyl residue;
an unsubstituted or substituted furanylmethyl residue;
an unsubstituted or substituted phenyl residue;
an unsubstituted or substituted benzyl residue;
an unsubstituted or substituted phenethyl residue;
the group

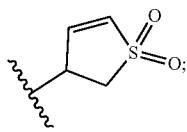 [SMILES: *C1C=CS(=O)(=O)C1]

or
the group

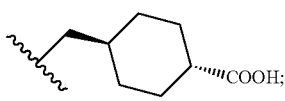 [SMILES: *C[C@H]1CC[C@H](C(=O)O)CC1]

or
Y is —$NR_3R_4$ with N, $R_3$ and $R_4$ forming an unsubstituted or substituted 5- or 6-membered saturated heterocycle,

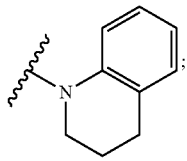 [SMILES: *N1CCCc2ccccc21]

or
Y is —$OR_{11}$, with $R_{11}$ is —H or —$C_1$-$C_4$-alkyl, phenyl, benzyl or 2-ethoxyethyl; and
$W_1$, $W_2$, and $W_3$ are identical or different, and are —H, -halogen, or —$C_1$-$C_4$-alkyl.
In one embodiment, the invention relates to a compound of the general formula (I),
wherein
R is —H or -methyl;
$R_1$ is —H; and
$W_1$, $W_2$, and $W_3$ are identical or different, and are —H or —Cl.

DETAILED DESCRIPTION OF THE INVENTION

Definitions, Abbreviations and Acronyms

"5- or 6-membered saturated heterocycle" represents an unsubstituted or substituted ring system containing 5 or 6 ring atoms and containing in addition to C atoms one N atom and optionally one additional heteroatom. The additional heteroatoms are preferably selected from O, N or S. Especially preferred are heterocycles with only one N as a heteroatom. Preferably, these substituted heterocycles are single or twofold substituted.

"$C_1$-$C_4$-alkyl" represents a straight-chain or branched-chain alkyl group with 1 to 4 carbon atoms. Examples of straight-chain and branched groups include, but are not limited to, methyl, ethyl, propyl, isopropyl, butyl, isobutyl, and tert.-butyl, preferably methyl and ethyl and most preferred methyl.

"$C_3$-$C_8$-cycloalkyl" represents a carbocyclic saturated ring system having 3 to 8 carbon atoms, preferably 3 to 6 carbon atoms. Examples of $C_3$-$C_8$-cycloalkyl include, but are not limited cyclopropyl, cyclobutyl, cyclopentyl, cyclohexyl, cycloheptyl or cyclooctyl, preferably cyclopentyl and cyclohexyl.

"Substitution" or "substituted" represents one or more substituents commonly known in the art, or as specifically defined herein. The substituents are preferably selected from $C_1$-$C_4$-alkyl, —COO($CH_2$)$_n$H or —COO($CH_2$)$_n$OH with n=0-4, —CN, and halogen. Preferred substituents are methyl, ethyl or —COOH.

"Halogen" represents fluoro, chloro, bromo or iodo, preferably fluoro and chloro.

"Stereoisomer(s)" as it relates to a compound of formula (I) and to its intermediate compounds represents any possible enantiomers or diastereomers of a compound of formula (I) and its salts or hydrates. In particular, the term "stereoisomer" means a single compound or a mixture of two or more compounds, wherein at least one chiral center is predominantly present in one definite isomeric form, in particular the S-enantiomer, the R-enantiomer and the racemate of a compound of formula (I). It is also possible that two or more stereogenic centers are predominantly present in one definite isomeric form of a derivative of a compound of formula (I) as defined above. In the sense of the present invention, "predominantly" has the meaning of at least 60%, preferably at least 70%, particularly preferably at least 80%, most preferably at least 90%. According to the present invention, also stereoisomers of a compound of formula (I) may be present as a salt or a hydrate.

The terms stereoisomer, salt, and hydrate may also be used in conjunction with one another. For example, a stereoisomer of a compound of formula (I) may have a salt. Combinations of these terms are considered to be within the scope of the invention.

References to compounds by number refer to the compounds as defined in Table 2.

Technical terms are used by their common sense. If a specific meaning is conveyed to certain terms, definitions of terms will be given in the following in the context of which the terms are used.

The below mentioned general or preferred residue definitions apply both to the end products of the formula (I) and also, correspondingly, to the starting materials or intermediates of formulae (A) to (J) required in each case for the preparation. These residue definitions can be combined with one another at will, i.e. including combinations between the given preferred residues. Further, individual definitions may not apply.

Novel POLRMT Inhibitors

As indicated above, there is a need for alternative novel compounds, which inhibit POLRMT and are suitable for use as a medicament. In particular, a need exists for novel compounds that can be used in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer. Further, POLRMT inhibitors are of interest, which can be used in a method for treating cancer in simultaneous, alternating or subsequent combination with another cancer therapy.

A problem of the present invention was therefore to provide novel alternative compounds having the above-mentioned desired characteristics.

In one aspect, according to the present invention there is provided a compound of the general formula (I)

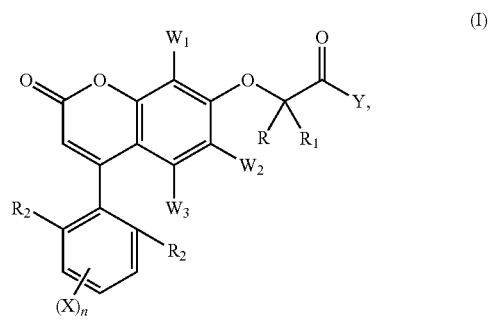

wherein
R is —H or —$C_1$-$C_4$-alkyl;
$R_1$ is —H or -methyl;
$R_2$ is —H;
n=0, 1 or 2;
X is -halogen, —$C_1$-$C_4$-alkyl, —OMe or —CN, preferably -halogen, —$C_1$-$C_4$-alkyl, or —CN, with n=1 or 2;
Y is —$NR_3R_4$ with
  $R_3$ is —H. or —$C_1$-$C_4$-alkyl, and
  $R_4$ is —H, —$C_1$-$C_4$-alkyl or —$C_3$-$C_8$-cycloalkyl;
    an unsubstituted or substituted pyridine residue;
    an unsubstituted or substituted pyridinylmethyl residue;
    an unsubstituted or substituted morpholinylethyl residue;
    an unsubstituted or substituted furanylmethyl residue;
    an unsubstituted or substituted phenyl residue;
    an unsubstituted or substituted benzyl residue;
    an unsubstituted or substituted phenethyl residue;
    the group

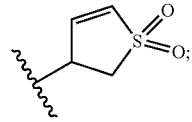

or
  the group

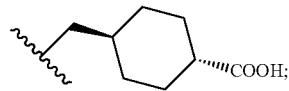 [SMILES: *C[C@H]1CC[C@H](C(=O)O)CC1]

or
Y is —$NR_3R_4$ with N, $R_3$ and $R_4$ forming an unsubstituted or substituted 5- or 6-membered saturated heterocycle, preferably an unsubstituted 5-membered saturated heterocycle, an unsubstituted or substituted 6-membered saturated heterocycle,

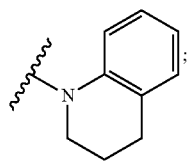

or

Y is —OR$_{11}$, with R$_{11}$ is —H or —C$_1$-C$_4$-alkyl, phenyl, benzyl or 2-ethoxyethyl; and W$_1$, W$_2$, and W$_3$ are identical or different, and are —H, -halogen, or —C$_1$-C$_4$-alkyl, or a pharmaceutically or veterinary acceptable salt, hydrate or solvate thereof.

Further included are pharmaceutically or veterinary acceptable salts, hydrates or solvates of the compounds of formula (I) or its intermediate compounds disclosed herein. A pharmaceutically or veterinary acceptable salt can be an anionic counterion, e.g. an acetate, a bromide, camsylate, chloride, citrate, formate, fumarate, lactate, maleate, mesylate, nitrate, oxalate, phosphate, sulfate, tartrate, thiocyanate, or tosylate, or preferably a cationic counterion, e.g. ammonium, arginine, diethylamine, ethylenediamine, piperazine, potassium, sodium, or any other counter ion disclosed in Haynes et al. (2005). Some compounds of the invention contain one or more chiral centers due to the presence of asymmetric carbon atoms, which gives rise to stereoisomers, for example to diastereoisomers with R or S stereochemistry at each chiral center. The invention includes all such stereoisomers and diastereoisomers and mixtures thereof.

As shown in the Examples, the inventors have now surprisingly and unexpectedly found that the compounds of general formula (I) or a pharmaceutically or veterinary acceptable salt, hydrate or solvate thereof, are useful as mitochondrial RNA polymerase (POLRMT) inhibitors and thereby inhibit mitochondrial DNA replication and/or mitochondrial transcription.

In the following, preferred groups of the compounds of general formula (I) of the present invention are described. The preferred groups constitute preferred embodiments of the compounds of general formula (I). Any combinations of the embodiments of the compounds of general formula (I) of the invention described herein are considered to be within the scope of the invention.

In one embodiment, the invention relates to a compound of formula (I) as defined above, wherein R is —H or -methyl;

R$_1$ is —H; and

W$_1$, W$_2$, and W$_3$ are identical or different, and are —H or —Cl.

In another embodiment, the invention relates to a compound of formula (I) as defined above, wherein W$_1$, W$_2$, and W$_3$ are identical and are —H.

In another embodiment, the invention relates to a compound of formula (I) as defined above, wherein W$_1$ and W$_3$ are identical and are —H; and W$_2$ is —Cl.

In another embodiment, the invention relates to a compound of formula (I) as defined above, wherein R is -methyl; and R$_1$ is —H.

In another embodiment, the invention relates to a compound of formula (I) as defined above, wherein R is —H and R$_1$ is —H.

In another embodiment, the invention relates to a compound of formula (I) as defined above, wherein n=1; and X is -halogen.

A preferred group of compounds are compounds of formula (I), wherein

R is —H, -methyl or -ethyl;

R$_1$ is —H;

R$_2$ is —H;

n=0 or 1, preferably n=0;

X is -halogen, —C$_1$-C$_4$-alkyl, —OMe or —CN, preferably -halogen, —C$_1$-C$_4$-alkyl, or —CN, with n=1;

Y is —NR$_3$R$_4$ with

R$_3$ is —H, or —C$_1$-C$_4$-alkyl, preferably —H or -methyl, and

R$_4$ is —H, —C$_1$-C$_4$-alkyl or —C$_3$-C$_8$-cycloalkyl;
an unsubstituted or substituted pyridine residue;
an unsubstituted or substituted pyridinylmethyl residue;
an unsubstituted or substituted morpholinylethyl residue;
an unsubstituted or substituted furanylmethyl residue;
an unsubstituted or substituted phenyl residue;
an unsubstituted or substituted benzyl residue;
an unsubstituted or substituted phenethyl residue;
the group

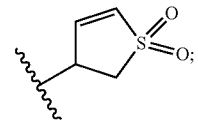

or
the group

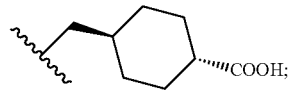 [SMILES: *C[C@H]1CC[C@H](C(=O)O)CC1]

or

Y is —NR$_3$R$_4$ with N, R$_3$ and R$_4$ forming an unsubstituted or substituted 5- or 6-membered saturated heterocycle, preferably an unsubstituted 5-membered saturated heterocycle, an unsubstituted or substituted 6-membered saturated heterocycle,

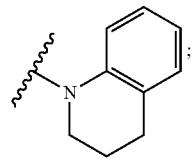 [SMILES: *N1CCCc2ccccc21]

or

Y is —OR$_{11}$, with R$_{11}$ is —H or —C$_1$-C$_4$-alkyl, phenyl, benzyl or 2-ethoxyethyl; and W$_1$, W$_2$, and W$_3$ are identical or different, and are —H, -halogen, or —C$_1$-C$_4$-alkyl.

Examples for compounds of this group are compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99.

An especially preferred group of compounds are compounds of formula (I), wherein n=0, i.e. compounds with an unsubstituted phenyl ring having the general formula (IA). Thus, in one embodiment, the invention relates to compounds of the general formula (IA)

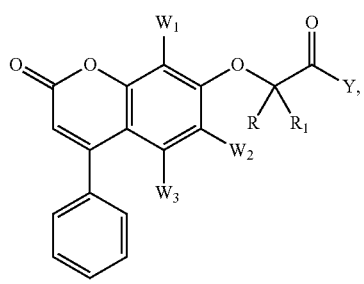

(IA)

wherein

R is —H or —$C_1$-$C_4$-alkyl;

$R_1$ is —H or -methyl;

Y is —$NR_3R_4$ with $R_3$ is —H, or —$C_1$-$C_4$-alkyl, and $R_4$ is —H, —$C_1$-$C_4$-alkyl or —$C_3$-$C_8$-cycloalkyl;

an unsubstituted or substituted pyridine residue;

an unsubstituted or substituted pyridinylmethyl residue;

an unsubstituted or substituted morpholinylethyl residue;

an unsubstituted or substituted furanylmethyl residue;

an unsubstituted or substituted phenyl residue;

an unsubstituted or substituted benzyl residue;

an unsubstituted or substituted phenethyl residue;

the group

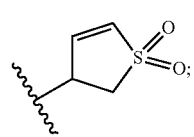 [SMILES: *C1C=CS(=O)(=O)C1]

or the group

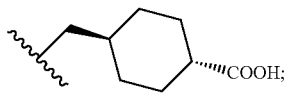 [SMILES: *C[C@H]1CC[C@H](C(=O)O)CC1]

or

Y is —$NR_3R_4$ with N, $R_3$ and $R_4$ forming an unsubstituted or substituted 5- or 6-membered saturated heterocycle,

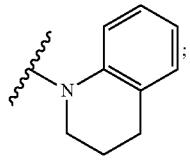 [SMILES: *N1CCCc2ccccc21]

or

Y is —$OR_{11}$, with $R_1$ is —H or —$C_1$-$C_4$-alkyl, phenyl, benzyl or 2-ethoxyethyl; and $W_1$, $W_2$, and $W_3$ are identical or different, and are —H, -halogen, or —$C_1$-$C_4$-alkyl, or a pharmaceutically or veterinary acceptable salt, hydrate or solvate thereof.

Examples for compounds of formula (IA) are compounds 1, 2, 3, 4, 5, 6, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99.

Another preferred group of compounds are compounds of formulae (I) and (IA) as defined above, wherein R is —H or -methyl;

$R_1$ is —H; and $W_1$, $W_2$, and $W_3$ are identical or different, and are —H or —Cl.

Examples for compounds of this group are compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 72, 73, 74, 75, 76, 77, 78, 79, 80, 81, 82, 83, 84, 85, 86, 88, 89, 90, 92, 93, 95, 96, 98 and 99.

Another preferred group of compounds of formulae (I) and (IA) are compounds of formulae (I) and (IA) as defined above, wherein $W_1$, $W_2$, and $W_3$ are identical and are —H. Examples for compounds of this group are compounds 1, 2, 3, 4, 5, 6, 7, 8, 9, 12, 14, 15, 16, 18, 19, 20, 21, 22, 23, 24, 25, 26, 29, 30, 31, 32, 33, 34, 35, 36, 37, 38, 39, 40, 41, 43, 44, 48, 51, 52, 53, 54, 55, 56, 60, 61, 62, 63, 64, 65, 66, 67, 68, 69, 70, 71, 72, 73, 74, 75, 76, 77, 81, 93 and 96.

Another preferred group of compounds are compounds of formulae (I) and (IA) as defined above, wherein $W_1$ and $W_3$ are identical and are —H; and $W_2$ is —Cl. Examples for compounds of this group are compounds 10, 11, 13, 17, 27, 28, 42, 45, 46, 47, 49, 50, 57, 58, 59, 78, 79, 82, 83, 84, 85, 86, 88, 89, 90, 92, 95, 98 and 99.

Another preferred group of compounds are compounds of formulae (I) and (IA) as defined above, wherein R is -methyl; and $R_1$ is —H. Examples for compounds of this group are compounds 1, 2, 3, 4, 5, 6, 7, 8, 9, 10, 11, 12, 13, 14, 15, 16, 17, 18, 19, 20, 21, 24, 25, 26, 27, 28, 29, 30, 31, 33, 34, 35, 36, 37, 38, 39, 41, 42, 50, 51, 52, 53, 55, 56, 58, 60, 61, 62, 63, 64, 65, 66, 67, 68, 69, 70, 72, 79, 80, 87, 89, 93, 96 and 97.

Another preferred group of compounds are compounds of formulae (I) and (IA) as defined above, wherein R is —H and $R_1$ is —H. Examples for compounds of this group are compounds 22, 23, 40, 43, 44, 45, 46, 47, 48, 49, 54, 57, 59, 73, 74, 75, 76, 77, 78, 81, 82, 83, 84, 85, 86, 88, 90, 91, 92, 94, 95, 98 and 99.

Another preferred group of compounds are compounds of formula (I) as defined above, wherein n=1; and X is -halogen. Examples for compounds of this group are compounds 3, 4, 7, 8 and 41.

A preferred group of compounds are compounds of formula (I), wherein
n=0, 1 or 2,
X is halogen, or —CN, with n=1 or 2;
Y is —NR$_3$R$_4$ with
R$_3$ is —H, or —C$_1$-C$_4$-alkyl, and
R$_4$ is —C$_1$-C$_4$-alkyl or —C$_3$-C$_8$-cycloalkyl; or
an unsubstituted or substituted pyridine residue; or
an unsubstituted or substituted phenyl residue;
Y is —NR$_3$R$_4$ with N, R$_3$ and R$_4$ forming an unsubstituted or substituted 5- or 6-membered saturated heterocycle; or
Y is —OR$_{11}$, with R$_1$ is —H or —C$_1$-C$_4$-alkyl, and
wherein R, R$_1$, R$_2$, W$_1$, W$_2$, and W$_3$ are as defined above.
Examples for compounds of this group are compounds 1, 2, 3, 4, 5, 6, 7, 8, 9, 10, 11, 12, 13, 14, 15, 16, 17, 18, 19, 20, 21, 22, 23, 25, 26, 28, 30, 31, 32, 33, 34, 35, 36, 37, 38, 39, 40, 41, 43, 44, 45, 46, 47, 48, 49, 50, 51, 52, 53, 54, 55, 56, 57, 58, 60, 61, 62, 63, 64, 65, 66, 68, 69, 71, 72, 74, 76, 77, 80, 81, 82, 85, 87, 88, 91, 92, 94 and 97. A preferred subgroup of these compounds are compounds, wherein n=0, i.e. compounds 1, 2, 5, 6, 10, 11, 12, 13, 14, 15, 16, 17, 18, 19, 20, 21, 22, 23, 25, 26, 28, 30, 31, 32, 33, 34, 35, 36, 37, 38, 39, 40, 43, 44, 45, 46, 47, 48, 49, 50, 51, 52, 53, 54, 55, 56, 57, 58, 60, 61, 62, 63, 64, 66, 68, 69, 71, 72, 74, 76, 77, 80, 81, 82, 85, 87, 88, 91, 92, 94 and 97. Another preferred subgroup of these compounds are compounds, wherein X is -halogen, preferably —Cl, —Br, or —F, or —CN, with n=1 or 2, i.e. compounds 3, 4, 7, 8 and 41.

Another preferred subgroup of these compounds are compounds of formula (I), wherein
n=0, 1 or 2,
X is —Cl, —Br, or —F, or —CN
Y is —NR$_3$R$_4$ with
R$_3$ is —H, or -methyl, and
R$_4$ is -methyl, ethyl, -isopropyl or -cyclopropyl; or
an unsubstituted or substituted pyridine residue; or
an unsubstituted or substituted phenyl residue;
Y is —NR$_3$R$_4$ with N, R$_3$ and R$_4$ forming an unsubstituted or substituted 5- or 6-membered saturated heterocycle; or
Y is —OR$_{11}$, with R$_{11}$ is —H or —C$_1$-C$_4$-alkyl, and
wherein R, R$_1$, R$_2$, W$_1$, W$_2$, and W$_3$ are as defined above.
More preferred are these compounds, wherein R is —H and R$_1$ is methyl and wherein n=0 (especially compounds 13, 14, 21, 36, 37, 38 and 69).
More preferred are these compounds, wherein the substituted phenyl residue is substituted at the para position.
More preferred are these compounds, wherein R$_{11}$ is —H, -methyl, -ethyl or -isopropyl.

Another more preferred group of compounds are compounds of formula (I), wherein
R is —H;
R$_1$ is -methyl;
wherein n=0
Y is —NR$_3$R$_4$ with
R$_3$ is —H and
R$_4$ is an unsubstituted pyridine residue (for example compounds 6, 11, 22, 55 and 61), or an unsubstituted pyridinylmethyl residue (for example compounds 59 and 99), and
wherein R$_2$, W$_1$, W$_2$, and W$_3$ are as defined above.
Another more preferred group of compounds are compounds of formula (I), wherein Y is —NR$_3$R$_4$ with R$_3$ is —H and R$_4$ is an unsubstituted morpholinoethyl residue and wherein n=0 (especially compounds 70, 79 and 83), and wherein R, R$_1$, R$_2$, W$_1$, W$_2$, and W$_3$ are as defined above.

Another more preferred group of compounds are compounds of formula (I), wherein
R is —H;
R$_1$ is —H or -methyl;
wherein n=0
Y is —NR$_3$R$_4$ with
R$_3$ is —H or methyl, and
R$_4$ is an unsubstituted or substituted phenyl residue, and wherein the phenyl residue is substituted with —OCH$_3$, —C$_2$H$_4$OH or —C$_3$H$_6$OH (for example compounds 5, 16, 17, 18, 25, 28, 40, 57 and 72), and
wherein R$_2$, W$_1$, W$_2$, and W$_3$ are as defined above.

Another more preferred group of compounds are compounds of formula (I), wherein
R is —H;
R$_1$ is —H or -methyl;
wherein n=0
Y is —NR$_3$R$_4$ with
R$_3$ is —H or methyl, and
R$_4$ is the group

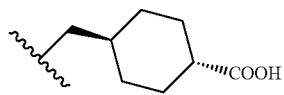 [SMILES: *C[C@H]1CC[C@H](C(=O)O)CC1]

for example compounds 89 or 98), and
wherein R$_2$, W$_1$, W$_2$, and W$_3$ are as defined above.

Another more preferred group of compounds are compounds of formula (I), wherein Y is —NR$_3$R$_4$ with N, R$_3$ and R$_4$ forming an unsubstituted or substituted 5- or 6-membered saturated heterocycle or

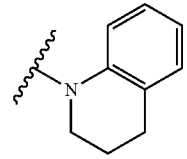 [SMILES: *N1CCCc2ccccc21]

(for example compounds 10, 13, 14, 15, 19, 20, 21, 23, 31, 35, 36, 37, 38, 39, 43, 45, 54, 60, 62, 63, 64, 68, 69, 78 and 85), and wherein R, R$_1$, R$_2$, n, X, W$_1$, W$_2$, and W$_3$ are as defined above. A more preferred subgroup of these compounds are compounds with N, R$_3$ and R$_4$ forming an unsubstituted or substituted piperidine residue wherein the piperidine is substituted with —COOH, —COOCH$_3$, —COOC$_2$H$_5$, —CONH$_2$, —CONHCH$_3$ or —CN (for example compounds 10, 13, 14, 15, 19, 21, 23, 35, 36, 37, 38, 39, 43, 54, 60, 62, 63, 64, 68, 69, 85, especially preferred are —COOH and —CH$_2$COOH as substituents (for example compounds 13, 14, 21, 36, 37, 54, 69 and 85). Preferably these compounds have n=0 and R is —H and R$_1$ is -methyl (for example compounds 10, 13, 14, 15, 19, 21, 35, 36, 37, 38, 39, 60, 62, 63, 64, 68 and 69). Another more preferred subgroup of these compounds are compounds with N, R$_3$ and R$_4$ forming a morpholino residue (for example compound 45). Another more preferred subgroup of the compounds are compounds with N, R$_3$ and R$_4$ forming a pyrrolidine (for example compound 31). Another more preferred subgroup of these compounds are compounds with N, R$_3$ and R$_4$ forming

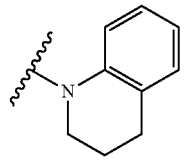 [SMILES: *N1CCCc2ccccc21]

(especially compound 78).

Another more preferred group of compounds are compounds of formula (I), wherein Y is —OR$_{11}$, with R$_{11}$ is —H or —C$_1$-C$_4$-alkyl, phenyl, benzyl or 2-ethoxyethyl (for example compounds 1, 3, 4, 7, 8, 9, 24, 32, 33, 41, 44, 49, 50, 51, 52, 53, 56, 58, 65, 66, 71, 73, 74, 76, 77, 81, 82, 87, 88, 91, 92, 93, 94 and 97), and wherein R, R$_1$, R$_2$, n, X, W$_1$, W$_2$, and W$_3$ are as defined above. A more preferred subgroup of these compounds are compounds with n=0 and with R is —H and R$_1$ is —H or methyl (for example compounds 1, 24, 33, 44, 49, 50, 51, 52, 53, 56, 58, 66, 73, 74, 76, 77, 81, 82, 87, 88, 91, 92, 93, 94 and 97). Another more preferred subgroup of these compounds are compounds with n=1 and with X is halogen, and with R is —H and R$_1$ is —H or methyl (for example compounds 3, 4, 7, 8 and 41). An even more preferred subgroup of compounds are compounds with R$_{11}$ is —H (for example compounds 51, 66, 88 and 97), -methyl (for example compounds 56, 58 and 91), -ethyl (for example compounds 3, 4, 7, 8, 9, 32, 33, 41, 49, 50, 52, 65, 71, 81 and 87), -propyl (for example compound 92), -isopropyl (for example compound 53), -tert-butyl (for example compounds 1, 44, 82 and 94), -phenyl (for example compound 24), -benzyl (for example compound 93) or -2-ethoxyethlyen (for example compound 73).

Another preferred group of compounds are compounds of formula (I), wherein Y is —NR$_3$R$_4$, wherein R$_3$=H and R$_4$=H (for example compounds 67, 75, 84), and wherein R, R$_1$, R$_2$, n, X, W$_1$, W$_2$, and W$_3$ are as defined above.

In another preferred embodiment, compounds, wherein n=1, X is —OMe at the para position, Y is —OH, W$_1$=—H or -methyl, W$_2$=—H and W$_3$=—H are excluded from the group of compounds of formula (I) of the invention.

In another preferred embodiment, the compounds of formula (I) of the invention do not comprise the compounds:

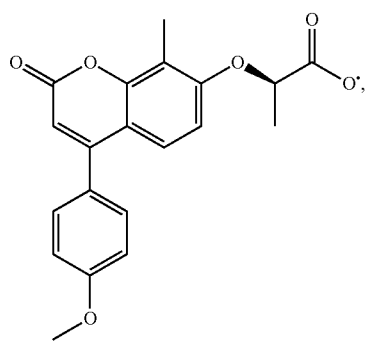

(Rank 21 of WO 2008/054475)

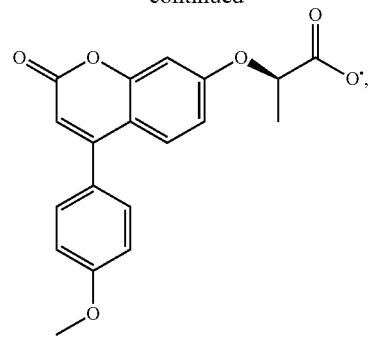

(Rank 22 of WO 2008/054475)

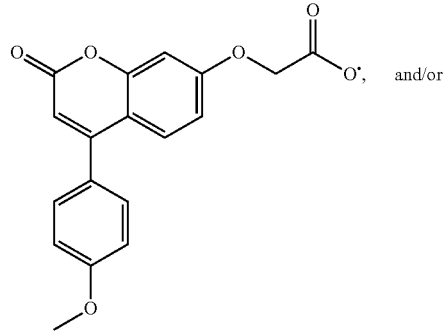

and/or (Rank 34 of WO 2008/054475)

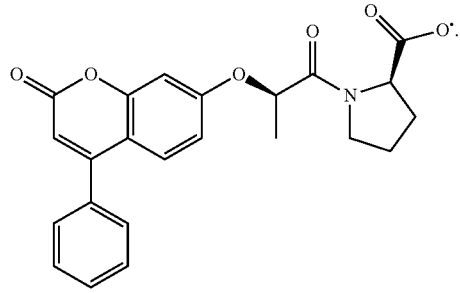

(Rank 66 of WO 2008/054475)

It is further mentioned that some of the compounds of the invention may actually function as prodrugs, i.e. they are quickly converted into the active POLRMT inhibitor upon administration to the patient. Examples of potential prodrugs are especially esters (see for example compounds 1, 3, 4, 7, 8, 9, 10, 15, 23, 24, 32, 33, 35, 38, 41, 43, 44, 49, 50, 52, 53, 56, 58, 63, 64, 65, 71, 73, 74, 76, 77, 81, 82, 87, 91, 92, 93, and 94).

A specific subset of compounds of the invention are compounds of formula (I) selected from:
tert-butyl 2-(2-oxo-4-phenyl-chromen-7-yl)oxypropanoate
N,N-dimethyl-2-(2-oxo-4-phenyl-chromen-7-yl)oxy-propanamide
ethyl 2-[4-(4-chlorophenyl)-2-oxo-chromen-7-yl]oxypropanoate
ethyl 2-[4-(3-chlorophenyl)-2-oxo-chromen-7-yl]oxypropanoate
N-[4-(3-hydroxypropyl)phenyl]-2-(2-oxo-4-phenyl-chromen-7-yl)oxy-propanamide
2-(2-oxo-4-phenyl-chromen-7-yl)oxy-N-(2-pyridyl)propanamide
ethyl 2-[4-(3-fluorophenyl)-2-oxo-chromen-7-yl]oxypropanoate ethyl 2-[4-(4-fluorophenyl)-2-oxo-chromen-7-yl]oxypropanoate
ethyl 2-[2-oxo-4-(p-tolyl)chromen-7-yl]oxypropanoate
methyl 1-[2-(6-chloro-2-oxo-4-phenyl-chromen-7-yl)oxypropanoyl]piperidine-3-carboxylate
2-(6-chloro-2-oxo-4-phenyl-chromen-7-yl)oxy-N-(2-pyridyl)propanamide
N-isopropyl-2-(2-oxo-4-phenyl-chromen-7-yl)oxy-propanamide
1-[2-(6-chloro-2-oxo-4-phenyl-chromen-7-yl)oxypropanoyl]piperidine-3-carboxylic acid
1-[2-(2-oxo-4-phenyl-chromen-7-yl)oxypropanoyl]piperidine-3-carboxylic acid
methyl 1-[2-(2-oxo-4-phenyl-chromen-7-yl)oxypropanoyl]piperidine-3-carboxylate
N-[4-(2-hydroxyethyl)phenyl]-2-(2-oxo-4-phenyl-chromen-7-yl)oxy-propanamide
2-(6-chloro-2-oxo-4-phenyl-chromen-7-yl)oxy-N-[4-(2-hydroxyethyl)phenyl]propanamide
N-[4-(2-hydroxyethyl)phenyl]-N-methyl-2-(2-oxo-4-phenyl-chromen-7-yl)oxy-propanamide
1-[2-(2-oxo-4-phenyl-chromen-7-yl)oxypropanoyl]piperidine-3-carbonitrile
7-[1-methyl-2-oxo-2-[3-(2H-tetrazol-5-yl)-1-piperidyl]ethoxy]-4-phenyl-chromen-2-one
(3S)-1-[(2R)-2-(2-oxo-4-phenyl-chromen-7-yl)oxypropanoyl]piperidine-3-carboxylic acid
2-(2-oxo-4-phenyl-chromen-7-yl)oxy-N-(2-pyridyl)acetamide
methyl 1-[2-(2-oxo-4-phenyl-chromen-7-yl)oxyacetyl]piperidine-3-carboxylate
phenyl 2-(2-oxo-4-phenyl-chromen-7-yl)oxypropanoate
2-(2-oxo-4-phenyl-chromen-7-yl)oxy-N-phenyl-propanamide
N-methyl-2-(2-oxo-4-phenyl-chromen-7-yl)oxy-propanamide
2-(6-chloro-2-oxo-4-phenyl-chromen-7-yl)oxy-N-(2-hydroxy-2-phenyl-ethyl)propanamide
2-(6-chloro-2-oxo-4-phenyl-chromen-7-yl)oxy-N-[4-(3-hydroxypropyl)phenyl]propanamide
N-(2-hydroxy-2-phenyl-ethyl)-2-(2-oxo-4-phenyl-chromen-7-yl)oxy-propanamide
N-ethyl-2-(2-oxo-4-phenyl-chromen-7-yl)oxy-propanamide
7-(1-methyl-2-oxo-2-pyrrolidin-1-yl-ethoxy)-4-phenyl-chromen-2-one
ethyl 2-methyl-2-(2-oxo-4-phenyl-chromen-7-yl)oxypropanoate
ethyl (2R)-2-(2-oxo-4-phenyl-chromen-7-yl)oxypropanoate
(2R)—N,N-dimethyl-2-(2-oxo-4-phenyl-chromen-7-yl)oxy-propanamide
ethyl (3S)-1-[(2R)-2-(2-oxo-4-phenyl-chromen-7-yl)oxypropanoyl]piperidine-3-carboxylate
(3S)-1-[2-(2-oxo-4-phenyl-chromen-7-yl)oxypropanoyl]piperidine-3-carboxylic acid
(3R)-1-[2-(2-oxo-4-phenyl-chromen-7-yl)oxypropanoyl]piperidine-3-carboxylic acid
methyl (3R)-1-[2-(2-oxo-4-phenyl-chromen-7-yl)oxypropanoyl]piperidine-3-carboxylate
7-[1-methyl-2-oxo-2-(1-piperidyl)ethoxy]-4-phenyl-chromen-2-one
N-[4-(2-hydroxyethyl)phenyl]-N-methyl-2-(2-oxo-4-phenyl-chromen-7-yl)oxy-acetamide
ethyl 2-[4-(4-bromophenyl)-2-oxo-chromen-7-yl]oxypropanoate
2-(6-chloro-2-oxo-4-phenyl-chromen-7-yl)oxy-N-(2-furylmethyl)propanamide
ethyl 1-[2-(2-oxo-4-phenyl-chromen-7-yl)oxyacetyl]piperidine-3-carboxylate
tert-butyl 2-(2-oxo-4-phenyl-chromen-7-yl)oxyacetate
6-chloro-7-(2-morpholino-2-oxo-ethoxy)-4-phenyl-chromen-2-one
2-(6-chloro-2-oxo-4-phenyl-chromen-7-yl)oxy-N-cyclopropyl-acetamide
2-(6-chloro-2-oxo-4-phenyl-chromen-7-yl)oxy-N,N-diethyl-acetamide
N,N-diethyl-2-(2-oxo-4-phenyl-chromen-7-yl)oxy-acetamide
ethyl 2-(6-chloro-2-oxo-4-phenyl-chromen-7-yl)oxyacetate
ethyl 2-(6-chloro-2-oxo-4-phenyl-chromen-7-yl)oxypropanoate
2-(2-oxo-4-phenyl-chromen-7-yl)oxypropanoic acid
ethyl 2-(2-oxo-4-phenyl-chromen-7-yl)oxypropanoate
isopropyl 2-(2-oxo-4-phenyl-chromen-7-yl)oxypropanoate
1-[2-(2-oxo-4-phenyl-chromen-7-yl)oxyacetyl]piperidine-3-carboxylic acid
2-(2-oxo-4-phenyl-chromen-7-yl)oxy-N-(3-pyridyl)propanamide
methyl 2-(2-oxo-4-phenyl-chromen-7-yl)oxypropanoate
2-(6-chloro-2-oxo-4-phenyl-chromen-7-yl)oxy-N-[4-(2-hydroxyethyl)phenyl]acetamide
methyl 2-(6-chloro-2-oxo-4-phenyl-chromen-7-yl)oxypropanoate
2-(6-chloro-2-oxo-4-phenyl-chromen-7-yl)oxy-N-(3-pyridylmethyl)acetamide
1-[2-(2-oxo-4-phenyl-chromen-7-yl)oxypropanoyl]piperidine-3-carboxamide
2-(2-oxo-4-phenyl-chromen-7-yl)oxy-N-(4-pyridyl)propanamide
N-methyl-1-[2-(2-oxo-4-phenyl-chromen-7-yl)oxypropanoyl]piperidine-3-carboxamide
methyl 1-[2-(2-oxo-4-phenyl-chromen-7-yl)oxypropanoyl]piperidine-4-carboxylate
ethyl rac-(3S)-1-[2-(2-oxo-4-phenyl-chromen-7-yl)oxypropanoyl]piperidine-3-carboxylate
ethyl 2-[4-(4-methoxyphenyl)-2-oxo-chromen-7-yl]oxypropanoate
(2R)-2-(2-oxo-4-phenyl-chromen-7-yl)oxypropanoic acid
2-(2-oxo-4-phenyl-chromen-7-yl)oxypropanamide
rac-(3S)—N,N-dimethyl-1-[2-(2-oxo-4-phenyl-chromen-7-yl)oxypropanoyl]piperidine-3-carboxamide
1-[2-(2-oxo-4-phenyl-chromen-7-yl)oxypropanoyl]piperidine-4-carboxylic acid
N-(2-morpholinoethyl)-2-(2-oxo-4-phenyl-chromen-7-yl)oxy-propanamide ethyl 2-(2-oxo-4-phenyl-chromen-7-yl)oxobutanoate
N-(4-methoxyphenyl)-2-(2-oxo-4-phenyl-chromen-7-yl)oxy-propanamide
2-ethoxyethyl 2-(2-oxo-4-phenyl-chromen-7-yl)oxyacetate
propyl 2-(2-oxo-4-phenyl-chromen-7-yl)oxyacetate
2-(2-oxo-4-phenyl-chromen-7-yl)oxyacetamide
butyl 2-(2-oxo-4-phenyl-chromen-7-yl)oxyacetate
isobutyl 2-(2-oxo-4-phenyl-chromen-7-yl)oxyacetate
6-chloro-7-[2-(3,4-dihydro-2H-quinolin-1-yl)-2-oxoethoxy]-4-phenyl-chromen-2-one
2-(6-chloro-2-oxo-4-phenyl-chromen-7-yl)oxy-N-(2-morpholinoethyl)propanamide
2-(5-fluoro-2-oxo-4-phenyl-chromen-7-yl)oxy-N,N-dimethyl-propanamide
ethyl 2-(2-oxo-4-phenyl-chromen-7-yl)oxyacetate
tert-butyl 2-(6-chloro-2-oxo-4-phenyl-chromen-7-yl)oxyacetate
2-(6-chloro-2-oxo-4-phenyl-chromen-7-yl)oxy-N-(2-morpholinoethyl)acetamide 2-(6-chloro-2-oxo-4-phenyl-chromen-7-yl)oxyacetamide
1-[2-(6-chloro-2-oxo-4-phenyl-chromen-7-yl)oxyacetyl]piperidine-3-carboxylic acid
2-(6-chloro-2-oxo-4-phenyl-chromen-7-yl)oxy-N-cyclooctyl-acetamide
ethyl 2-(5-fluoro-2-oxo-4-phenyl-chromen-7-yl)oxypropanoate
2-(6-chloro-2-oxo-4-phenyl-chromen-7-yl)oxyacetic acid
4-[[2-(6-chloro-2-oxo-4-phenyl-chromen-7-yl)oxypropanoylamino]methyl]cyclohexanecarboxylic acid
2-(6-chloro-2-oxo-4-phenyl-chromen-7-yl)oxy-N-(2-hydroxy-2-phenyl-ethyl)acetamide
methyl 2-(8-methyl-2-oxo-4-phenyl-chromen-7-yl)oxyacetate
propyl 2-(6-chloro-2-oxo-4-phenyl-chromen-7-yl)oxyacetate
benzyl 2-(2-oxo-4-phenyl-chromen-7-yl)oxypropanoate
tert-butyl 2-(8-methyl-2-oxo-4-phenyl-chromen-7-yl)oxyacetate
2-(6-chloro-2-oxo-4-phenyl-chromen-7-yl)oxy-N-(1,1-dioxo-2,3-dihydrothiophen-3-yl)acetamide
2-[2-(2-oxo-4-phenyl-chromen-7-yl)oxypropanoylamino]-2-phenyl-acetic acid
2-(2-oxo-4-phenyl-6-propyl-chromen-7-yl)oxypropanoic acid
4-[[[2-(6-chloro-2-oxo-4-phenyl-chromen-7-yl)oxyacetyl]amino]methy]cycohexanecarboxylic acid
2-(6-chloro-2-oxo-4-phenyl-chromen-7-yl)oxy-N-(2-pyridylmethyl)acetamide.

Processes for the Preparation of Compounds of the General Formula (I)

In one aspect, the present invention provides a novel process for the preparation of a compound of formula (I) of the invention comprising the steps of:

(a) reacting a compound of formula (A)

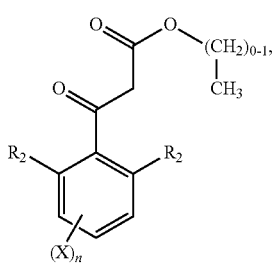

(A)

wherein $R_2$, n, and X are as defined above,
with a substituted or unsubstituted resorcin of formula (AA)

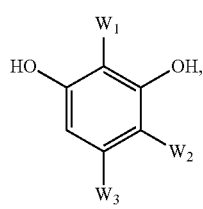

(AA)

wherein
$W_1$, $W_2$ and $W_3$ are as defined above,
to obtain a compound of formula (B)

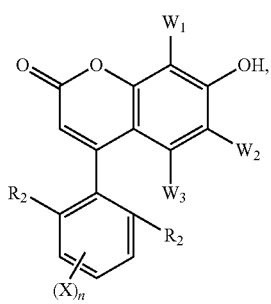

(B)

wherein $R_2$, n, X, $W_1$, $W_2$ and $W_3$ as defined above, and (b) alkylating a compound of formula (B) with an alkylating agent, preferably with an alkylating agent of the formula Z—OH or Z—Br, wherein Z is the group

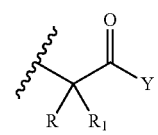

wherein R, $R_1$ and Y are as defined above,
to obtain a compound of formula (C)

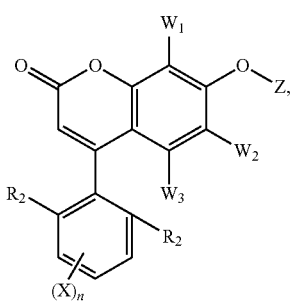

(C)

wherein $R_2$, n, X, $W_1$, $W_2$, $W_3$ and Z are as defined above.
The compounds of formula (C) correspond to compounds of formula (I) as defined above.

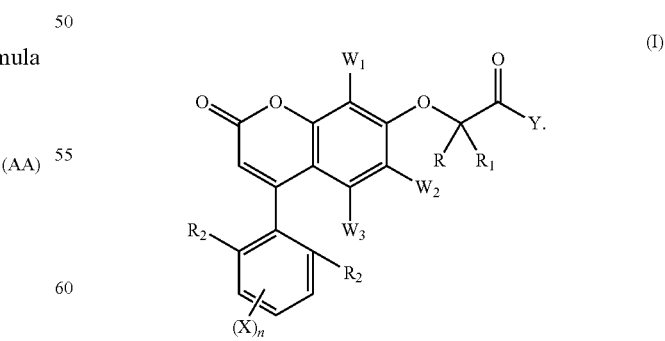

(I)

The compounds of formula (A) used as a starting material in process step (a) are either commercially available or are prepared in similar manners as described in literature procedures or in the specific examples. Substituted or unsubstituted resorcins used as a starting material in process step (a) are commercially available or can be obtained by standard procedures known to the skilled person.

The desired coumarine compounds of formula (B) may be prepared according to process step (a) from the corresponding β-ketoesters of formula (A) and the required resorcinol through a Pechmann cyclisation such as the one described by Leonetti et al. (2004) or Gosselin et al. (2010). Further literature examples include publications such as Tasler et al., WO 2016/146583A1, p. 49—Scheme 1, or Sharma et al. (2013).

In process step (b), alkylation of the compounds of formula (B) can be carried out with any suitable alkylating agent under standard alkylation conditions, e.g. with an alkylbromide (Z—Br), or with an alcohol (Z—OH) according to the Mitsunobu reaction (Mitsunobu et al. 1967).

Both process steps (a) and (b) can be carried out according to standard procedures known in the art, whereas further guidance can be found in the reaction schemes and examples disclosed below.

In one aspect, the invention relates to an intermediate compound of formula (B) as defined above.

In another aspect, the present invention relates to a process for the preparation of a compound of formula (I) of the invention, wherein Y is —$NR_3R_4$, and wherein $R_3$ and $R_4$ are as defined above corresponding to a compound of formula (F), comprising the steps of:

(a) hydrolyzing a compound of formula (D)

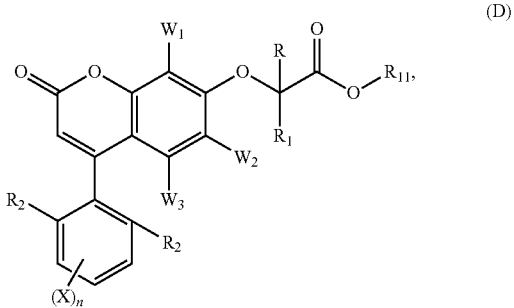

(D)

wherein $R_{11}$ is —$C_1$-$C_4$-alkyl, phenyl, benzyl or 2-ethoxyethyl, and

R, $R_1$, $R_2$, n, X, $W_1$, $W_2$ and $W_3$ are as defined above, to obtain a compound of formula (E)

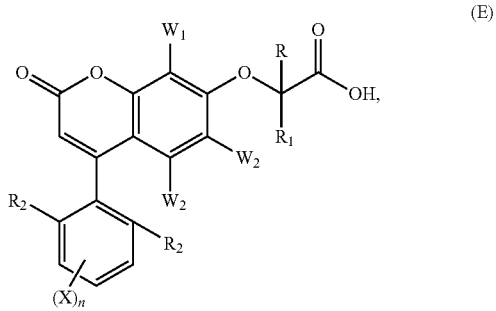

(E)

wherein R, $R_1$, $R_2$, n, X, $W_1$, $W_2$ and $W_3$ are as defined above, and (b) amidating a compound of formula (E) to obtain a compound of formula (F)

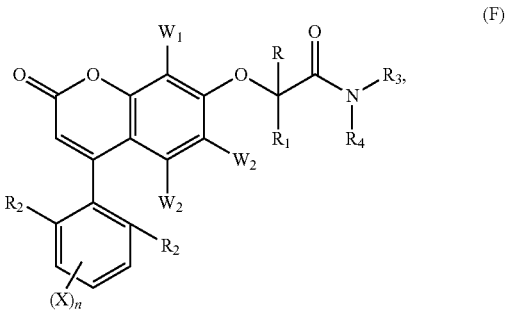

(F)

wherein R, $R_1$, $R_2$, $R_3$, $R_4$, n, X, $W_1$, $W_2$ and $W_3$ are as defined above, The compounds of formula (D) used as starting material in process step (a) correspond to compound of formula (I), wherein Y=—$OR_{11}$, and can be obtained for example by the first process for the preparation of compounds of formula (I) as described above.

The optionally substituted amines used as starting materials in process step (b) are commercially available or can be prepared by standard procedures.

In one aspect, the invention relates to an intermediate compound of formula (E) as defined above.

Again, both reaction steps can be carried out according to standard procedures known in the art, whereas further guidance can be found in the reaction schemes and examples disclosed below. For example, process step (b) can be carried out with an optionally substituted amine according to known standard procedures.

The general synthesis of a compound of formula (I) of this invention as described above is exemplified below in Schemes 1 to 3.

Scheme 1 shows the preparation of a compound of formula (C) corresponding to compounds of formula (I) as defined above. As mentioned above, the starting materials are either commercially available or are prepared in similar manners as described in literature procedures or in the specific examples. The desired coumarines of formula (B) were commercially available or were prepared from the corresponding β-ketoesters of formula (A), wherein X is defined as above, and the required resorcinol through a Pechmann cyclisation such as the one described by Leonetti et al. (2004) or Gosselin et al. (2010). Further literature examples include publications such as Tasler et al., WO 2016/146583A1, p. 49—Scheme 1, or Sharma et al. (2013).

The coumarins of formula (B) can be further alkylated with a commercial alkylbromide (Z—Br) or subjected to a Mitsunobu (Z—OH) reaction with a commercial alcohol to produce compounds of formula (C).

It is apparent to the skilled person that the sequence of the synthetic steps is dependent on the starting materials' availability and functional group compatibility and could vary from compound to compound.

Scheme 1: Exemplary preparation of a compound of formula (C)

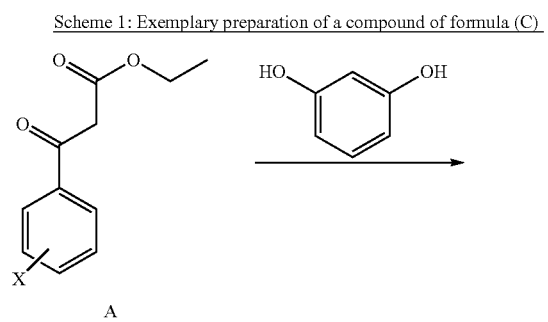

A

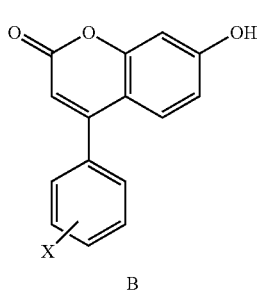

B

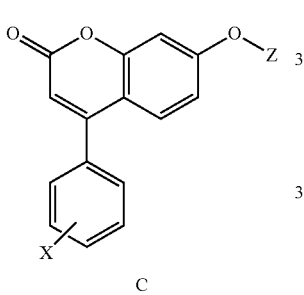

C

For the examples described in this patent, Z was a potentially substituted alkyl acetate group; this was usually further modified by hydrolysis to the corresponding carboxylic acid of formula (E), followed by coupling with a commercially available, optionally substituted amine, according to standard procedures known in the art, and as described in Scheme 2, to produce compounds of formula (F). The residues X, R, $R_1$, $R_3$, $R_4$, and $R_{11}$ shown in the formulae (D), (E), and (F) are as defined above. The specific procedures are described in detail in the Examples.

Scheme 2: Exemplary preparation of a compound of formula (F)

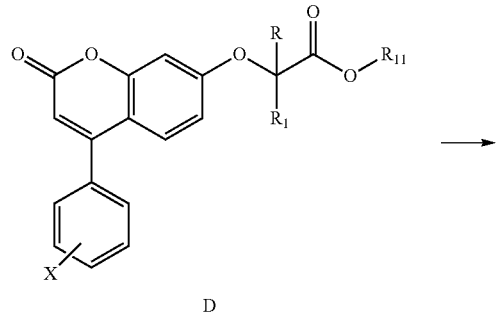

D

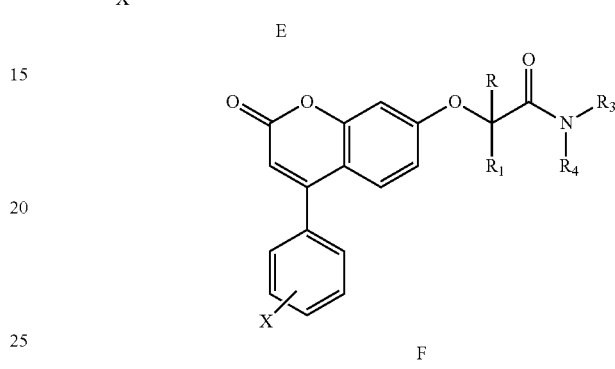

E

F

When $R_3$ and $R_4$ form an optionally substituted cyclic amide, this amide can carry an ester moiety, as highlighted in formula G, which can be further hydrolyzed to obtain compounds of substructure H. The compounds of formula (G) used as starting material can be obtained for example by the process for the preparation of compounds of formula (I) as described above. Examples are outlined in Scheme 3. When the commercially available esters were racemic, the coupling reaction could be followed by chiral preparative HPLC. The residues X, R and $R_1$ shown in the formulae (G) and (H) are as defined above, k=1 or 2; and $R_{12}$ is -methyl or -ethyl.

Scheme 3: Exemplary preparation of a compound of formula (H)

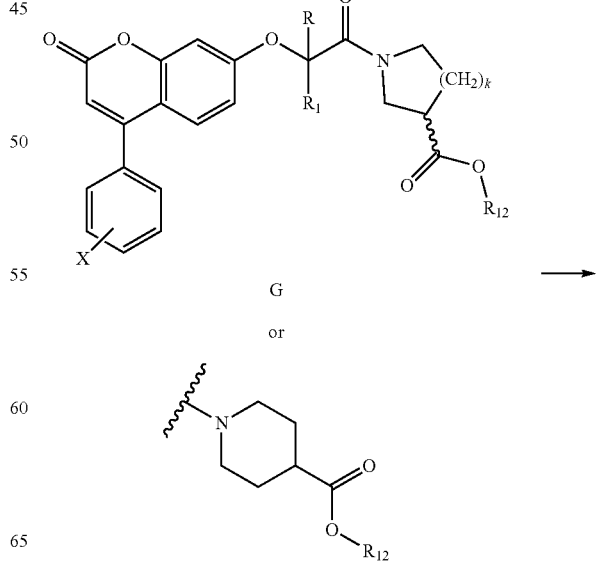

G or

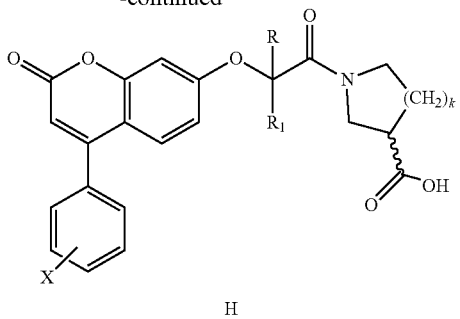

Use of the Novel Compounds of Formula (I) as a Medicament

Furthermore, it has been found that the compounds of formula (I) are suitable for use as a medicament. Specifically, it has been found that the compounds of formula (I) can be used in the treatment of cancer, preferably in the treatment of melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

POLRMT inhibitors previously have been described to trigger the death of AML cells allegedly through rather unspecific inhibition of mitochondrial transcription confirms this rational (Bralha et al. 2015). As described in the examples below, the compounds of formula (I) of the invention were surprisingly and unexpectedly shown to have cytostatic activity on a number of tumor cells and tumor models both in vitro and in vivo.

Accordingly, the compounds of formula (I) of the invention and their pharmaceutically or veterinary acceptable salts, hydrates or solvates, exhibit valuable pharmacological properties and are therefore useful as a medicament or pharmaceutical. The medicament or pharmaceutical can be further formulated with additional pharmaceutically or veterinary acceptable carriers and/or excipients, e.g. for oral administrations in the form of tablets. Tablets may contain suitable binders, lubricants, disintegrating agents, coloring agents, flavoring agents, flow-inducing agents and/or melting agents, generally known in the art.

Thus, in one aspect, the invention relates to a compound of the general formula (I) as defined herein for use as a medicament.

Compounds of the invention exhibit a marked and selective inhibitory effect on the POLRMT. This can be determined for example in the Homogeneous TR-FRET assay (see example 4) or the Quantitative real time-PCR assay (see example 5). The skilled person however may use different assays to determine the direct or indirect inhibition of POLRMT.

As mentioned above, it has been found that the compounds of formula (I) of the invention are useful in the treatment of cancer. There is evidence that in melanoma and especially in metastatic melanoma OXPHOS plays a major role in cancer cells and that inhibition of mitochondria in general may lead to superior treatment success. For example, it was shown that H3K4-demethylase (JARID1B) and OXPHOS dependent drug resistance play a role in metastatic melanoma (Roesch et al. 2013). Haq t al. (2013) describe that the standard of care (SoC) treatment with MEK inhibitors in melanoma leads to PGC1-a-dependent increase in OXPHOS as a drug-resistance escape route. It was also shown that the inhibition of mutated BRAF by vemurafenib increases OXPHOS dependency of BRAF mutated melanoma cells (Schöckel et al. 2015). And further, enhanced OXPHOS, glutaminolysis and 1-oxidation constitute the metastatic phenotype of melanoma cells (Rodrigues et al. 2016).

For pancreatic cancer selective killing of OXPHOS-dependent Panc-1 cells has been described for treatment with arctigenin (Brecht et al. 2017). In hepatocellular carcinoma, standard of care (SoC) treatment with MEK inhibitor is leading to PGC1-a-dependent increase in OXPHOS as a drug-resistance escape route (Bhat et al. 2013, Ling et al. 2017). For lymphoma it has been demonstrated that OXPHOS is dependent on mt-complex III inhibitor antimycinA (Dörr et al. 2013). As described above, acute myeloid leukemia, POLRMT inhibitors previously have been described to trigger the death of AML cells allegedly through rather unspecific inhibition of mitochondrial transcription (Bralha et al. 2015).

Also breast cancer should be a suitable cancer indication as overexpression of progesterone receptor is present in more than 50% of all breast cancer patients, whereas progesterone is stimulating mitochondrial activity with subsequent inhibition of apoptosis (Nadji et al. 2005, Behera et al. 2009). Further, the inhibition of mTOR leads to a shift towards OXPHOS-dependence and there is a glucose-dependent effect of mTOR inhibitors in combination with metformin (Pelicano et al. 2014, Ariaans et al. 2017). Additionally, it is described that mitochondrial dysfunction caused by metformin prevents tumor growth in breast cancer (Sanchez-Alvarez et al. 2013).

For glioblastoma it is known that malignant repopulation is dependent on OXPHOS (Yeung et al. 2014). With respect to cervical cancer, POLRTM inhibitors inhibit free fatty acid oxidation (data not shown), which otherwise promote cervical cancer cell proliferation (Rodriguez-Enriquez et al. 2015). In renal cancer there is evidence that Birt-Hogg-Dub6 renal tumors are associated with up-regulation of mitochondrial gene expression (Klomp et al. 2010). In colon carcinoma the rational is based on the finding that 5-fluorouracil resistant colorectal/colon cancer cells are addicted to OXPHOS to survive and enhance stem-like traits (Denise et al. 2015).

Accordingly, in another aspect, the invention relates to compounds of formula (I) of the invention as defined herein for use in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

The compounds of the invention are preferably useful in a method for treating cancer in simultaneous, alternating or subsequent combination with another cancer therapy, preferably selected from chemotherapy, immunotherapy, hormone therapy, stem cell transplantation therapy, radiation therapy or surgery. It is likely that the cytostatic activity of the POLRMT inhibitors on tumor cells can be further enhanced by combining the treatment with the respective standard of care in order to get improved/additive treatment results. In this context simultaneous, alternating or subsequent application of the various treatments is envisaged. Any of the standard classes of cancer therapy, chemotherapy, immunotherapy, hormone therapy, stem cell transplantation therapy, radiation therapy or surgery, appears to be feasible for combination with the POLRMT inhibitors of this invention.

Thus, in another aspect, the invention relates to a compound of the general formula (I) as defined herein for use in a method for treating cancer in simultaneous, alternating or subsequent combination with another cancer therapy, preferably selected from chemotherapy, immunotherapy, hormone therapy, stem cell transplantation therapy, radiation therapy or surgery.

The present invention also concerns a method for treating a patient suffering from cancer, which comprises the step of administering a therapeutically effective amount of a compound as described above, preferably in simultaneous, alternating or subsequent combination with another cancer therapy as e.g. disclosed above.

EXAMPLES

Abbreviations and Acronyms

Abbreviations and Acronyms used in the description and in the Examples are:
aq. aqueous
br. broad
$Bu_3SnN_3$ tributyltin azide
$CHCl_3$ chloroform
cHex cyclohexane
$Cs_2CO_3$ cesium carbonate
d doublet
DCM dichloromethane
DIAD diisopropylazodicarboxylate
DMF dimethylformamide
DMSO dimethylsulfoxide
DMSO-$d_6$ deuterated dimethylsulphoxide
EDC 1-Ethyl-3-(3-dimethylaminopropyl)carbodiimide
ES electrospray
$Et_3N$ triethylamine
EtOAc ethyl acetate
h hour
HCl hydrochloric acid
$H_2O$ water
HOBt 1H-benzo[d][1,2,3]triazol-1-ol
m multiplet
MeCN acetonitrile
MeOH methanol
min minutes
MS mass spectrometry
$NaHCO_3$ sodium hydrogencarbonate
NaCl sodium chloride
NaH sodium hydride
$NH_4Cl$ ammonium chloride
NMR nuclear magnetic resonance
$PPh_3$ triphenylphosphine
q quartet
rt room temperature
s singlet
sat. saturated
t triplet
THF tetrahydrofuran

1. Methods of Making the Compounds of Formula (I) of the Present Invention

In general, the compounds of formula (I) of the invention might be prepared by standard techniques known in the art, by known processes analogous thereto, and/or by the processes described herein, using starting materials which are either commercially available or producible according to conventional chemical methods. The particular processes to be utilised in the preparation of the compounds of formula (I) of this invention depend upon the specific compound desired. Such factors as the type of substitution at various locations of the molecule and the commercial availability of the starting materials play a role in the path to be followed and in the chosen reaction conditions for the preparation of the specific compounds of formula (I) of this invention. Those factors are readily recognised by one of ordinary skill in the art.

The following preparative methods are presented to aid the reader in the synthesis of the compounds of the present invention.

2. Experimental Procedures

LC-MS Method

HPLC—electrospray mass spectra (HPLC ES-MS) were obtained using a Waters Acquity Ultra Performance Liquid Chromatography (UPLC) equipped SQ 3100 Mass detector spectrometer.
Column: Acquity UPLC BEH C18 1.7 µm, 2.1×50 mm
Flow: 0.500 mL/min
Eluents: A: $H_2O$ with 0.05% formic acid and B: MeCN with 0.05% formic acid.
Gradient: Elution from 5% to 100% B over 3.5 min with an initial hold of 0.5 min and a final hold at 100% B of 0.5 min. Total run time: 5 min.
The gradient described could be altered in function of the physico-chemical properties of the compound analyzed and is in no way restrictive.

Preparative HPLC Method

Preparative HPLC was performed using a Waters System consisting of a Waters 2767 Sample Manager, a Waters 2545 Binary Gradient Module, a Waters SFO (System Fluidics Organizer), a Waters 3100 Mass Detector, and a Waters 2498 UV/Visible Detector.
Column: XBridge® Prep C18 5 µm OBD™, 19×150 mm
Flow: 20 mL/min
Eluents: A: $H_2O$ with 0.1% TFA and B: MeCN with 0.1% TFA.
General Gradient: Elution from X % to Y % B over 20 min with an initial hold of 2 min and a final increase to 100% B over 2 min and hold at 100% B of 2 min followed by a 1 min gradient back to the initial composition. Total run time: 26 min. X=Y–30% where Y=concentration of elution on the above described LC-MS method.
The gradient described could be altered in function of the physico-chemical properties of the compound analysed and is in no way restrictive.

Chiral LC-MS Method

Chiral HPLC—electrospray mass spectra (HPLC ES-MS) were obtained using a Waters Acquity Ultra Performance Liquid Chromatography (UPLC) equipped SQ 3100 Mass detector spectrometer.
Column: Lux 5u Cellulose-2; 150×4.6 mm
Flow: 0.500 mL/min-1.000 mL/min
Eluents: A: $H_2O$ with 0.05% formic acid and B: MeCN with 0.05% formic acid.
Gradient: Elution from X % to Y % B over 15 min with an initial hold of 0.5 min and a return to 100% B and final hold at of 2.5 min. Total run time: 18 min. Example for compound 47: X=55%; Y=65%
The gradient could be altered in function of the physico-chemical properties of the compound analyzed and is in no way restrictive.

Chiral Preparative HPLC Method

Preparative HPLC was performed using a Waters System consisting of a Waters 2767 Sample Manager, a Waters 2545

Binary Gradient Module, a Waters SFO (System Fluidics Organizer), a Waters 3100 Mass Detector, and a Waters 2498 UV/Visible Detector.

Column: Lux 5u Cellulose-2, 150×21.2 mm (Phenomenex)

Flow: 20 mL/min-30 mL/min

Eluents: A: $H_2O$ with 0.1% TFA and B: MeCN with 0.1% TFA.

Gradient example for compound 108: Elution from 30% to 50% B over 30 min with an initial hold of 3 min and a final hold at 100% B of 6 min. Total run time: 39 min.

The gradient could be altered in function of the physico-chemical properties of the compound analysed and is in no way restrictive.

GC-MS Method

Gas Chromatography—Mass spectra were obtained using Agilent 7820A GC with 5977E MSD.

Column: HP-5MS 30 m, 0.25 mm ID, 0.25 μm

Flow: 2 mL/min. He

Injection: 100 μl/s, 250° C.; Split Flow: 20 mL/min. Split Ratio: 10

Detection: Agilent 5977E

Gradient: 0 min 50° C.; 0.5 min 50° C.; 7.6 min 300° C.; 9.6 min 300° C.

The gradient described could be altered in function of the physico-chemical properties of the compound analyzed and is in no way restrictive.

NMR Methods

Proton ($^1H$) nuclear magnetic resonance (NMR) spectra were measured with an Oxford Varian 400/54 (400 MHz) spectrometer or a Bruker Avance II (300 MHz) spectrometer with residual protonated solvent ($CHCl_3$ δ 7.26; MeOH δ 3.30; DMSO δ 2.49) as standard. The NMR data of the synthesized examples, are in agreement with their corresponding structural assignments.

Synthetic Methods

The general synthesis of a compound of this invention is described as disclosed above, e.g. as shown in Schemes 1 to 3.

3. Experimental Examples of the Invention

The following specific examples are presented to illustrate the invention, but they should not be construed as limiting the scope of the invention in any way. In the tables listing the intermediates, the compounds might have characterization such as $(M+H)^+$ mass spectrometry data, HPLC purity and/or NMR. Those that have no characterization are commercially available, and a CAS number is given.

3.1 Preparation of Intermediates for the Preparation of Compounds of Formula (I)

At least one example for the preparation of an intermediate per method is described below:

3.1.1 Preparation of Intermediate Compounds of Formula (B)

The β-ketoester starting materials of formula (A) required for the Pechmann condensation reaction are purchased from standard suppliers. The coumarins of formula (B) are either commercially available, or synthesized as described in the example below.

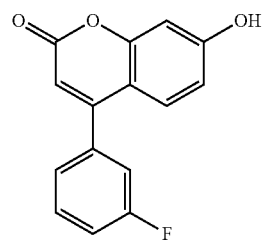 [SMILES: O=c1cc(-c2cccc(F)c2)c2ccc(O)cc2o1]

Resorcinol (200 mg, 1.82 mmol) was dissolved in (3-fluorobenzoyl)acetic acid ethyl ester (347 mg, 297 μL, 1.65 mmol) and a (1:1) mixture of $H_2SO_4$/TFA (4.2 mL) was added at 0° C. The mixture was allowed to warm up to rt and stirred 2 h, upon which $H_2O$ was added. The resulting precipitate was filtered, washed with $H_2O$ (10 mL) and dried in vacuo to yield the desired product 4B (399 mg, 94%) as a pink solid.

$^1H$ NMR (400 MHz, DMSO-d) δ 10.65 (s, 1H), 7.59 (ddd, J=9.2, 7.6, 5.9 Hz, 1H), 7.43-7.30 (m, 3H), 7.25 (d, J=8.5 Hz, 1H), 6.82-6.73 (m, 2H), 6.19 (s, 1H).

MS (ES) $C_{15}H_9FO_3$ requires: 256, found: 257 $(M+H)^+$, 95%.

The coumarin intermediates 5B to 12B were synthesized in a similar manner as for intermediate 4B (see Table 1).

TABLE 1

| | Hydroxy-Coumarins of formula (B) | | |
|---|---|---|---|
| Intermediate | Structure | $(M + H)^+$, purity | |
| 1B |  | CAS: 2555-30-8 | |
| 2B |  | CAS: 21392-48-3 | |
| 3B |  | CAS: 53391-72-3 | |

TABLE 1-continued

Hydroxy-Coumarins of formula (B)

| Intermediate | Structure | (M + H)+, purity |
|---|---|---|
| 4B | 4-(3-fluorophenyl)-7-hydroxycoumarin | MS (ES) $C_{15}H_9FO_3$ requires: 256, found 257 (M + H)+, 95% |
| 5B | 4-(4-fluorophenyl)-7-hydroxycoumarin | MS (ES) $C_{15}H_9FO_3$ requires: 256, found 257 (M + H)+, 95% |
| 6B | 4-(4-chlorophenyl)-7-hydroxycoumarin | MS (ES) $C_{15}H_9ClO_3$ requires: 272/274, found 273/275 (M + H)+, 100% |
| 7B | 4-(4-methylphenyl)-7-hydroxycoumarin | MS (ES) $C_{16}H_{12}O_3$ requires: 252, found 253 (M + H)+, 94% |
| 8B | 4-(4-bromophenyl)-7-hydroxycoumarin | MS (ES) $C_{15}H_9BrO_3$ requires: 272/274, found 317/319 (M + H)+, 97% |
| 9B | 4-(3-chlorophenyl)-7-hydroxycoumarin | MS (ES) $C_{15}H_9ClO_3$ requires: 272/274, found 273/275 (M + H)+, 91% |
| 10B | 5-fluoro-7-hydroxy-4-phenylcoumarin | MS (ES) $C_{15}H_9FO_3$ requires: 256, found 257 (M + H)+, 98% |

3.1.2 Preparation of Intermediate Compounds of Formula (D)

Intermediate 4D—Synthesis According to Method 2 (M2)

Ethyl 2-((4-(3-fluorophenyl)-2-oxo-2H-chromen-7-yl)oxy)propanoate (4D-7)

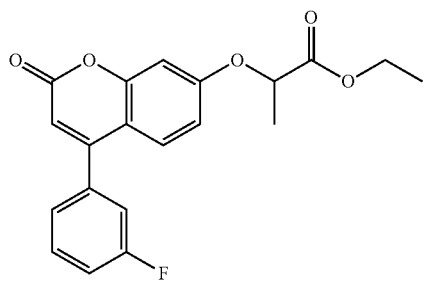 [SMILES: CCOC(=O)C(C)Oc1ccc2c(-c3cccc(F)c3)cc(=O)oc2c1]

Intermediate 4B (256 mg, 0.391 mmol) was dissolved in DMF (1 mL) and Cs$_2$CO$_3$ (170 mg, 0.781 mmol), followed by ethyl 2-bromopropanoate (76 µL, 0.586 mmol) were added. The reaction was stirred at 70° C. for 1 h. The mixture was diluted with water and extracted with EtOAc. The organic layer was washed with water and brine, dried over MgSO$_4$, filtered and evaporated in vacuo. The crude product was purified by flash chromatography on silica gel using a gradient of EtOAc in cHex to yield the desired product 4D (90.8 mg, 59%) as an off-white solid.

$^1$H NMR (400 MHz, Chloroform-d) δ 7.55-7.44 (m, 1H), 7.39-7.32 (m, 1H), 7.29-7.16 (m, 2H), 7.15 (dddd, 1H), 6.86-6.78 (m, 2H), 6.22 (s, 1H), 4.81 (q, 1H), 4.25 (q, 2H), 1.67 (d, 3H), 1.33-1.23 (m, 3H).

MS (ES) $C_{20}H_{17}FO_5$ requires: 356, found: 357 (M+H)+, 100%.

Intermediate (R)-1D—Synthesis According to Method 3 (M3)

(R)-ethyl 2-((2-oxo-4-phenyl-2H-chromen-7-yl)oxy)propanoate ((R)-1D)

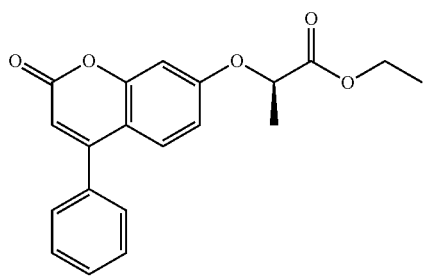 [SMILES: CCOC(=O)[C@@H](C)Oc1ccc2c(-c3ccccc3)cc(=O)oc2c1]

7-Hydroxy-4-phenylcoumarin (1B) (150 mg, 0.63 mmol) and PPh₃ (181 mg, 0.693 mmol) were dissolved in THF (6.3 mL), and (−)-Ethyl (S)-2-hydroxypropionate (111 mg, 0.945 mmol) was added. The reaction was cooled to 0° C. and DIAD (496 µl, 2.52 mmol) was added dropwise. The reaction was then stirred at rt for 1 h. The mixture was diluted with EtOAc and washed with a sat. NaHCO₃ solution, a sat. NH₄Cl solution, and water. The organic layer was dried over MgSO₄, filtered and evaporated in vacuo. The crude product was purified by flash chromatography on silica gel using a gradient of EtOAc in cHex to yield the desired product (R)-1D (218 mg, 100%) as a colorless glue.

¹H NMR (400 MHz, Chloroform-d) δ 7.47-7.42 (m, 3H), 7.38-7.34 (m, 2H), 7.32 (dd. J=8.3, 0.9 Hz, 1H), 6.76-6.71 (m, 2H), 6.16 (d, J=0.6 Hz, 1H), 4.74 (q, J=6.8 Hz, 1H), 4.21-4.14 (m, 2H), 1.60 (dd, J=6.7, 0.7 Hz, 3H), 1.24-1.20 (m, 3H).

MS (ES) $C_{20}H_{18}O_5$ requires: 338, found: 339 (M+H)⁺, 100%.

3.1.3 Preparation of Intermediate Compounds of Formula (E)

Intermediate (R)-1E—Synthesis According to Method 4 (M4)

(R)-2-((2-oxo-4-phenyl-2H-chromen-7-yl)oxy)propanoic acid ((R)-1E-66)

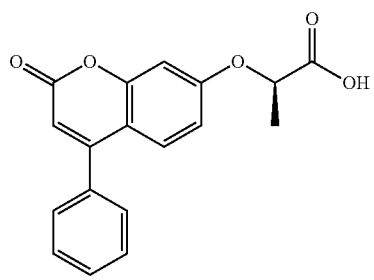 [SMILES: C[C@@H](Oc1ccc2c(-c3ccccc3)cc(=O)oc2c1)C(=O)O]

Intermediate (R)-1D (210 mg, 0.621 mmol) was dissolved in a (3:1) mixture of THF/MeOH (4 mL) and 2M NaOH aq. solution (2 mL) was added. The reaction was stirred at rt for 30 min, upon which 2M HCl (2.5 mL) was added. The mixture was extracted with EtOAc, and the combined organic layers were dried over MgSO₄, filtered, and evaporated in vacuo to yield the desired product (R)-1E (160 mg, 83%) as a white wax.

¹H NMR (400 MHz, DMSO-d) δ 13.13 (s, 1H), 7.59-7.46 (m, 5H), 7.33 (d1H), 6.97 (d, 1H), 6.89 (dd, 1H), 6.23 (s, 1H), 5.05 (q, 1H), 1.52 (d, 3H).

MS (ES) $C_{18}H_{14}O_5$ requires: 310, found: 311 (M+H)⁺, 100%.

The esters and carboxylic acids intermediates 1, 3, 4, 8, 9, 24, 32, 41, 53, 71, 81, 87 shown in Table 2 were synthesized in a similar manner as for intermediates 1D, (R)-1D and (R)-1E. Further esters are commercially available or their synthesis is described elsewhere.

3.1.4 Preparation of Intermediate Compounds of Formula (G)

Intermediate 1G—Synthesis According to Method 5 (M5)

(3R)-methyl 1-(2-((2-oxo-4-phenyl-2H-chromen-7-yl)oxy)propanoyl)piperidine-3-carboxylate (1G-38)

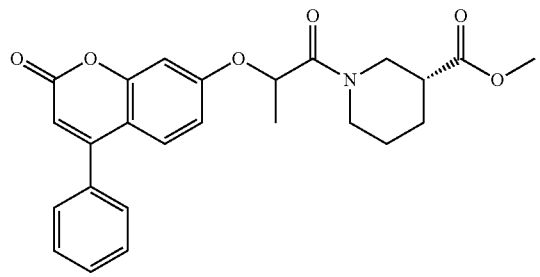 [SMILES: COC(=O)[C@@H]1CCCN(C(=O)C(C)Oc2ccc3c(-c4ccccc4)cc(=O)oc3c2)C1]

Intermediate 1E (30 mg, 0.097 mmol), EDC.HCl (22 mg, 0.116 mmol), and HOBt.xH₂O (16 mg, 0.116 mmol) were dissolved in DMF (1 mL) and (R)-piperidine-3-carboxylic acid methyl ester (33 mg, 0.232 mmol) was added slowly. Et₃N (16 µL, 11.7 mmol) was added, and the mixture was stirred at 80° C. for 2 h. The reaction was diluted with EtOAc and washed with water, a sat. NaHCO₃ solution, a sat.NH₄Cl solution, and again with water. The organic phase was dried over MgSO₄, filtered and evaporated in vacuo. The crude product was purified by flash chromatography on silica gel using a gradient of EtOAc in cHex to yield the desired product 1G (33 mg, 78%) as a colorless glue.

¹H NMR (400 MHz, DMSO-d₆) δ 7.60-7.47 (m, 5H), 7.33 (t, J=9.2 Hz, 1H), 6.99 (s, OH), 6.96-6.80 (m, 2H), 6.22 (d, J=1.8 Hz, 1H), 5.46 (ddt, J=18.7, 12.6, 6.5 Hz, 1H), 4.24-3.72 (m, 2H), 3.69-3.54 (m, 3H), 3.25-2.93 (m, 1H), 2.67-2.37 (m, 2H), 2.02-1.58 (m, 3H), 1.56-1.36 (m, 4H).

MS (ES) $C_{25}H_{25}NO_6$ requires: 435. found: 436 $(M+H)^+$, 100%.

3.2 Preparation of Compounds of Formula (I) of the Invention

Compound 37—Synthesis According to Method 4 (M4)

(3R)-1-(2-((2-oxo-4-phenyl-2H-chromen-7-yl)oxy)propanoyl)piperidine-3-carboxylic acid (37)

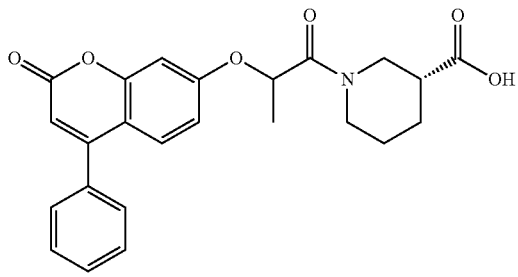

Intermediate 1G (28 mg, 0.0652 mmol) was dissolved in THF (1 mL) and 2 M NaOH aq. solution (0.5 mL) was added. A few drops of MeOH were added until the mixture was homogeneous. The reaction was stirred at rt for 1 h, neutralized with 2 M HCl, and stirred for a further 30 min. The mixture was extracted with EtOAc and the combined organic phases were washed with water, dried over $MgSO_4$, filtered and evaporated in vacuo to yield the desired product 37 (26 mg, 95%) as a white solid.

$^1$H NMR (400 MHz, DMSO-$d_6$) δ 12.39 (s, 1H), 7.60-7.47 (m, 5H), 7.38-7.27 (m, 1H), 7.01-6.80 (m, 2H), 6.22 (d, J=3.4 Hz, 1H), 5.55-5.38 (m, 1H), 4.31-3.45 (m, 2H), 3.24-3.08 (m, 2H), 2.92-2.69 (m, 1H), 2.35-2.22 (m, 1H), 2.02-1.87 (m, 1H), 1.82-1.36 (m, 6H).

MS (ES) $C_{24}H_{23}NO_8$ requires: 421, found: 422 $(M+H)^+$, 97%

Compound 20—Synthesis According to Method 6 (M6)

7-((1-(3-(2H-tetrazol-5-yl)piperidin-1-yl)-1-oxopropan-2-yl)oxy)-4-phenyl-2H-chromen-2-one (20)

The tetrazole derivative (20) described in Table 2 was synthesized from the corresponding nitrile according to Method 6:

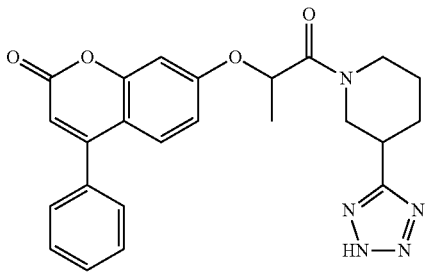 [SMILES: CC(Oc1ccc2c(-c3ccccc3)cc(=O)oc2c1)C(=O)N1CCCC(c2nn[nH]n2)C1]

Compound (19) (57 mg, 0.142 mmol) was dissolved in o-dichlorobenzene (1.4 mL) and $Bu_3SnN_3$ (236 mg, 0.710 mmol) was added in a sealed tube. The reaction was stirred at 125° C. for 1 h 30 min. The mixture was allowed to cool to rt, filtered through a plug of silica and washed with DCM (30 mL) and 20% MeOH in DCM (400 mL). The latest fraction was evaporated in vacuo, re-suspended in EtOAc, and extracted with a 20:1 sat. $NaHCO_3$/1 M NaOH solution. The combined aq. phases were re-acidified to pH 1 and extracted with EtOAc. The combined organic phases were dried over $MgSO_4$, filtered, and evaporated in vacuo. The crude product was purified by flash chromatography on silica gel using a gradient of MeOH in DCM to yield the desired product (20) (32 mg, 50%) as an off-white solid.

$^1$H NMR (400 MHz, DMSO-$d_6$) δ 7.60-7.46 (m, 5H), 7.32 (q, J=10.1, 9.5 Hz, 1H), 7.01-6.75 (m, 2H), 6.23 (d, J=1.9 Hz, 1H), 5.49 (ddt, J=26.7, 13.0, 6.4 Hz, 1H), 4.45-2.69 (m, 5H), 2.22-2.05 (m, 1H), 1.91-1.61 (m, 2H), 1.56-1.40 (m, 4H).

MS (ES) $C_{24}H_{23}N_5O_4$ requires: 445, found: 446 $(M+H)^+$, 100%

The compounds of formula (I) exemplifying the invention are described in Table 2 and Table 3.

It should be assumed that methods 2 and 3, optionally followed by methods 4, 5 and again method 4, were used to yield the target compound.

TABLE 2

| | Compounds of formula (I) of the invention | | |
|---|---|---|---|
| | Structure | $^1$H-NMR | LC purity |
| 1 | 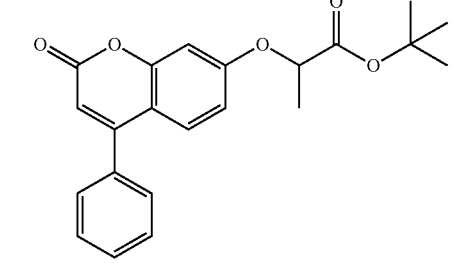 | $^1$H NMR (300 MHz, Chloroform-d) δ 7.47-7.28 (m, 6H), 6.78-6.68 (m, 2H), 6.16 (s, 1H), 4.62 (q, J = 6.8 Hz, 1H), 1.56 (d, J = 6.7 Hz, 3H), 1.40 (s, 9H). | 94% |

TABLE 2-continued

Compounds of formula (I) of the invention

| | Structure | ¹H-NMR | LC purity |
|---|---|---|---|
| 2 | [4-phenyl-coumarin-7-yloxy-propanoyl N,N-dimethylamide] | ¹H NMR (300 MHz, Methanol-d₄) δ 7.50-7.26 (m, 6H), 6.81-6.67 (m, 2H), 6.09 (d, J = 2.3 Hz, 1H), 5.25 (qd, J = 6.7, 2.2 Hz, 1H), 3.10 (d, J = 2.1 Hz, 3H), 2.87 (d, J = 2.3 Hz, 3H), 1.47 (dd, J = 6.7, 2.3 Hz, 3H). | 95% |
| 3 | [4-(4-chlorophenyl)-coumarin-7-yloxy-propanoic acid ethyl ester] | ¹H NMR (400 MHz, Chloroform-d) δ 7.54-7.46 (m, 2H), 7.42-7.29 (m, 3H), 6.85-6.77 (m, 2H), 6.20 (s, 1H), 4.81 (q, J = 6.8 Hz, 1H), 4.24 (qd, 7.1, 0.6 Hz, 2H), 1.67 (dd, J = 6.8, 0.7 Hz, 3H), 1.29 (td, J = 7.2, 0.7 Hz, 3H). | 99% |
| 4 | [4-(3-chlorophenyl)-coumarin-7-yloxy-propanoic acid ethyl ester] | ¹H NMR (400 MHz, Chloroform-d) δ 7.53-7.36 (m, 3H), 7.39-7.21 (m, 2H), 6.81 (dqd, J = 5.1, 2.6, 0.7 Hz, 2H), 6.20 (d, J = 0.7 Hz, 1H), 4.86-4.75 (m, 1H), 4.23 (qd, J = 7.2, 0.8 Hz, 2H), 1.66 (dd, J = 6.8, 0.8 Hz, 3H), 1.32-1.25 (m, 3H). | 96% |
| 5 | [4-phenyl-coumarin-7-yloxy-propanoyl amide with 4-(3-hydroxypropyl)aniline] | ¹H NMR (300 MHz, Chloroform-d) δ 3.09 (s, 1H), 7.50-7.27 (m, 8H), 7.13-7.02 (m, 2H), 6.92 (d, J = 2.6 Hz, 1H), 6.80 (dd, J = 8.9, 2.6 Hz, 1H), 6.17 (s, 1H), 4.80 (q, J = 6.7 Hz, 1H), 3.57 (t, J = 6.4 Hz, 2H), 2.73 (s, 1H), 2.59 (dd, J = 8.7, 6.8 Hz, 2H), 1.85-1.69 (m, 2H), 1.63 (d, J = 6.6 Hz, 3H). | 97% |
| 6 | [4-phenyl-coumarin-7-yloxy-propanoyl N-(2-pyridyl)amide] | ¹H NMR (300 MHz, Chloroform-d) δ 8.63 (s, 1H), 8.25-8.13 (m, 2H), 7.73-7.60 (m, 1H), 7.51-7.29 (m, 6H), 7.01 (ddd, J = 7.4, 4.9, 1.1 Hz, 1H), 6.91 (d, J = 2.6 Hz, 1H), 6.81 (dd, J = 8.9, 2.6 Hz, 1H), 6.18 (s, 1H), 4.83 (q, J = 6.7 Hz, 1H), 1.65 (d, J = 6.8 Hz, 3H). | 98% |

TABLE 2-continued

Compounds of formula (I) of the invention

| | Structure | ¹H-NMR | LC purity |
|---|---|---|---|
| 7 | (structure: 4-(3-fluorophenyl)-7-(1-ethoxycarbonylethoxy)coumarin) | ¹H NMR (400 MHz, Chloroform-d) δ 7.55-7.44 (m, 1H), 7.39-7.32 (m, 1H), 7.29-7.16 (m, 2H), 7.15 (dddd, J = 9.1, 2.6, 1.6, 0.4 Hz, 1H), 6.86-6.78 (m, 2H), 6.22 (s, 1H), 4.81 (q, J = 6.8 Hz, 1H), 4.25 (q, J = 7.1 Hz, 2H), 1.67 (d, J = 6.8 Hz, 3H), 1.33-1.23 (m, 3H). | 100% |
| 8 | (structure: 4-(4-fluorophenyl)-7-(1-ethoxycarbonylethoxy)coumarin) | ¹H NMR (400 MHz, Chloroform-d) δ 7.47-7.38 (m, 2H), 7.39-7.31 (m, 1H), 7.29-7.16 (m, 2H), 6.86-6.78 (m, 2H), 6.21 (d, J = 1.2 Hz, 1H), 4.81 (dt, J = 7.7, 6.2 Hz, 1H), 4.24 (tdd, J = 6.8, 1.0 Hz, 2H), 1.70-1.63 (m, 3H), 1.33-1.23 (m, 3H). | 100% |
| 9 | (structure: 4-(4-methylphenyl)-7-(1-ethoxycarbonylethoxy)coumarin) | ¹H NMR (400 MHz, Chloroform-d) δ 7.46-7.39 (m, 1H), 7.34-7.30 (m, 4H), 6.80 (d, J = 7.5 Hz, 2H), 6.21 (s, 1H), 4.81 (q, J = 6.8 Hz, 1H), 4.24 (q, J = 7.1 Hz, 2H), 2.45 (s, 3H), 1.66 (d, J = 6.8 Hz, 3H), 1.33-1.23 (m, 4H). | 90% |
| 10 | (structure: 6-chloro-4-phenyl-7-[1-(3-methoxycarbonylpiperidin-1-yl)-1-oxopropan-2-yloxy]coumarin) | ¹H NMR (300 MHz, Chloroform-d) δ 7.53-7.33 (m, 4H), 7.40-7.30 (m, 2H), 6.96-6.73 (m, 1H), 6.23-6.14 (m, 1H), 5.33-4.94 (m, 1H), 4.50 (d, J = 13.3 Hz, 0.26H), 4.35-3.98 (m, 1H), 3.92-3.73 (m, 1H), 3.69-3.56 (m, 3H), 3.36 (t, J = 9.5 Hz, 0.30H), 3.27-3.01 (m, 1H), 2.85 (q, J = 13.0 Hz, 0.56H), 2.60-1.83 (m, 1H), 1.79-1.37 (m, 6H). | 99% |
| 11 | (structure: 6-chloro-4-phenyl-7-[1-(pyridin-2-ylamino)-1-oxopropan-2-yloxy]coumarin) | ¹H NMR (300 MHz, Chloroform-d) δ 8.86 (s, 1H), 8.28-8.13 (m, 2H), 7.67 (td, J = 7.9, 1.3 Hz, 1H), 7.47 (d, J = 3.5 Hz, 4H), 7.41-7.29 (m, 2H), 7.01 (dd, 7.4, 4.9 Hz, 1H), 6.93 (s, 1H), 6.22 (s, 1H), 4.88 (q, J = 6.7 Hz, 1H), 1.72 (d, J = 6.7 Hz, 3H). | 99% |

TABLE 2-continued

Compounds of formula (I) of the invention

| | Structure | ¹H-NMR | LC purity |
|---|---|---|---|
| 12 | (structure) | ¹H NMR (300 MHz, Chloroform-d) δ 7.45 (q, J = 3.6 Hz, 3H), 7.35 (q, J = 4.0 Hz, 3H), 6.85 (t, J = 3.2 Hz, 1H), 6.78-6.67 (m, 1H), 6.22-6.06 (m, 2H), 4.72-4.58 (m, 1H), 4.13-3.95 (m, 1H), 1.53 (dd, J = 6.7, 3.8 Hz, 3H), 1.07 (ddd, J = 27.5, 6.6, 3.8 Hz, 6H). | 98% |
| 13 | (structure) | ¹H NMR (300 MHz, Methanol-d₄) δ 7.55-7.25 (m, 6H), 6.84 (d, J = 32.4 Hz, 1H), 6.14 (t, J = 4.1 Hz, 1H), 5.53-5.19 (m, 1H), 4.45-3.77 (m, 2H), 3.10-2.15 (m, 2H), 2.09-1.10 (m, 8H). | 98% |
| 14 | (structure) | ¹H NMR (300 MHz, Chloroform-d) δ 8.48 (s, 1H), 7.45-7.29 (m, 6H), 6.85-6.66 (m, 2H), 6.28-5.98 (m, 1H), 5.31-4.92 (m, 1H), 4.58-3.64 (m, 2H), 3.53-2.70 (m, 2H), 2.63-1.92 (m, 2H), 1.79-1.28 (m, 5H). | 95% |
| 15 | (structure) | ¹H NMR (300 MHz, Chloroform-d) δ 7.44 (d, J = 3.3 Hz, 2H), 7.41-7.17 (m, 4H), 6.87-6.69 (m, 2H), 6.13 (d, J = 4.3 Hz, 1H), 5.24-4.90 (m, 1H), 4.52-3.76 (m, 2H), 3.74-3.48 (m, 4H), 3.32-2.74 (m, 2H), 2.56-2.21 (m, 1H), 2.11-1.81 (m, 1H), 1.78-1.13 (m, 5H). | 98% |
| 16 | (structure) | ¹H NMR (400 MHz, DMSO-d₆) δ 10.12 (s, 1H), 7.58-7.45 (m, 7H), 7.36 (dd, J = 8.9, 0.8 Hz, 1H), 7.13 (d, J = 8.3 Hz, 2H), 7.06-7.00 (m, 1H), 7.00-6.92 (m, 1H), 6.23 (d, J = 0.9 Hz, 1H), 5.03 (q, J = 6.5 Hz, 1H), 4.56 (td, J = 5.2, 0.9 Hz, 1H), 3.53 (td, J = 7.1, 5.2 Hz, 2H), 2.64 (t, J = 7.1 Hz, 2H), 1.57 (d, J = 6.5 Hz, 3H). | 98% |

TABLE 2-continued

Compounds of formula (I) of the invention

| | Structure | ¹H-NMR | LC purity |
|---|---|---|---|
| 17 | (structure) | ¹H NMR (400 MHz, DMSO-d₆) δ 10.17 (s, 1H), 7.61-7.53 (m, 3H), 7.55-7.46 (m, 4H), 7.35 (s, 1H), 7.19-7.12 (m, 3H), 6.31 (s, 1H), 5.15 (q, J = 6.5 Hz, 1H), 4.61-4.53 (m, 1H), 3.54 (td, J = 7.1, 5.2 Hz, 2H), 2.66 (t, J = 7.1 Hz, 2H), 1.62 (d, J = 6.5 Hz, 3H). | 96% |
| 18 | (structure) | ¹H NMR (400 MHz, DMSO-d₆) δ 7.61-7.46 (m, 5H), 7.37-7.23 (m, 5H), 6.68 (d, J = 10.1 Hz, 2H), 6.21 (s, 1H), 4.80 (d, J = 6.7 Hz, 1H), 4.60 (td, J = 5.3, 0.8 Hz, 1H), 3.53 (q, J = 6.7 Hz, 2H), 3.14 (s, 3H), 2.69 (t, J = 7.0 Hz, 2H), 1.39-1.33 (m, 3H). | 94% |
| 19 | (structure) | ¹H NMR (400 MHz, DMSO-d₆) δ 7.58-7.46 (m, 5H), 7.31 (q, J = 10.5, 9.4 Hz, 1H), 6.97 (dd, J = 21.1, 10.6 Hz, 1H), 6.85 (dd, J = 8.9, 2.5 Hz, 1H), 6.22 (s, 1H), 5.49 (q, J = 6.4 Hz, 1H), 3.95-3.34 (m, 4H), 3.16-3.00 (m, 1H), 1.93-1.66 (m, 2H), 1.66-1.42 (m, 5H). | 90% |
| 20 | (structure) | ¹H NMR (400 MHz, DMSO-d₆) δ 7.60-7.46 (m, 5H), 7.32 (q, J = 10.1, 9.6 Hz, 1H), 7.01-6.75 (m, 2H), 6.23 (d, J = 1.9 Hz, 1H), 5.49 (ddt, J = 26.7, 13.0, 6.4 Hz, 1H), 4.45-2.69 (m, 5H), 2.22-2.05 (m, 1H), 1.91-1.61 (m, 2H), 1.56-1.40 (m, 4H). | 93% |
| 21 | (structure) | ¹H NMR (400 MHz, DMSO-d₆) δ 12.34 (br. s, 1H), 7.60-7.47 (m, 5H), 7.32 (dd, J = 16.8, 8.8 Hz, 1H), 6.98-6.90 (m, 1H), 6.91-6.80 (m, 1H), 6.25-6.19 (m, 1H), 5.52-5.43 (d, 1H), 4.29-3.46 (m, 2H), 3.23-3.07 (m, 1H), 2.89-2.16 (m, 1H), 2.01-1.93 (m, 1H), 1.80-1.66 (m, 1H), 1.64-1.40 (m, 3H), 1.49-1.39 (m, 3H). | 95% |

TABLE 2-continued

Compounds of formula (I) of the invention

| | Structure | ¹H-NMR | LC purity |
|---|---|---|---|
| 22 | 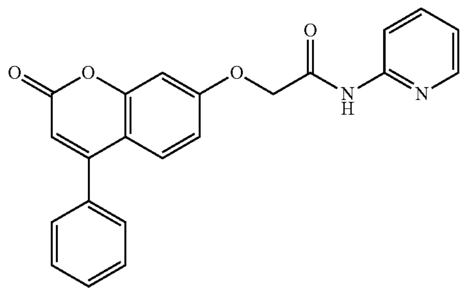 [SMILES: O=C(COc1ccc2c(-c3ccccc3)cc(=O)oc2c1)Nc1ccccn1] | ¹H NMR (300 MHz, Pyridine-d₅) δ 12.86 (s, 1H), 10.20 (s, 2H), 10.03 (d, J = 8.5 Hz, 1H), 9.89 (dd, J = 13.0, 5.7 Hz, 1H), 9.15 (t, J = 7.8 Hz, 1H), 9.06 (s, 1H), 9.00 (s, 1H), 8.91 (dd, 6.9, 3.2 Hz, 3H), 8.86-8.78 (m, 1H), 8.70 (d, J = 6.9 Hz, 2H), 8.56-8.43 (m, 2H), 6.72 (s, 2H). | 90% |
| 23 | 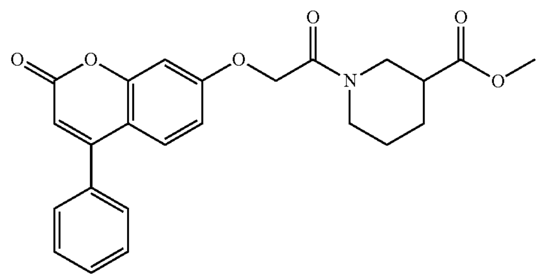 [SMILES: COC(=O)C1CCCN(C(=O)COc2ccc3c(-c4ccccc4)cc(=O)oc3c2)C1] | ¹H NMR (300 MHz, Chloroform-d) δ 7.50-7.29 (m, 6H), 6.82 (ddd, J = 11.9, 5.0, 2.5 Hz, 2H), 6.17 (d, J = 2.3 Hz, 1H), 4.95-4.79 (m, 1H), 4.81-4.68 (m, 1H), 4.45 (d, J = 14.0 Hz, 0.34H), 3.77-3.48 (m, 5H), 3.36 (ddd, J = 12.9, 8.4, 3.6 Hz, 0.67H), 3.15-2.85 (m, 1H), 2.47 (ddt, J = 34.8, 10.6, 4.9 Hz, 1H), 2.10-1.36 (m, 4H). | 99% |
| 24 | 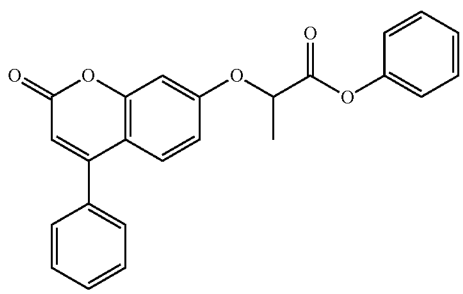 [SMILES: CC(Oc1ccc2c(-c3ccccc3)cc(=O)oc2c1)C(=O)Oc1ccccc1] | ¹H NMR (300 MHz, Chloroform-d) δ 7.47-7.22 (m, 8H), 7.22-7.10 (m, 1H), 7.10-6.95 (m, 2H), 6.91-6.72 (m, 2H), 6.17 (s, 1H), 4.99 (q, J = 6.8 Hz, 1H), 1.76 (d, J = 6.7 Hz, 3H). | 98% |
| 25 | 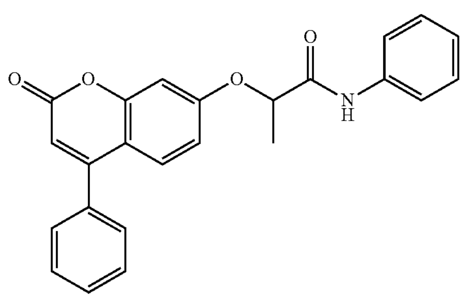 [SMILES: CC(Oc1ccc2c(-c3ccccc3)cc(=O)oc2c1)C(=O)Nc1ccccc1] | ¹H NMR (300 MHz, Chloroform-d) δ 8.05 (s, 1H), 7.53-7.40 (m, 5H), 7.46-7.25 (m, 3H), 7.30-7.16 (m, 2H), 7.13-7.00 (m, 1H), 6.93 (d, J = 2.5 Hz, 1H), 6.80 (dd, J = 8.9, 2.6 Hz, 1H), 6.18 (s, 1H), 4.81 (q, J = 6.7 Hz, 1H), 1.64 (d, J = 6.7 Hz, 3H). | 99% |
| 26 | 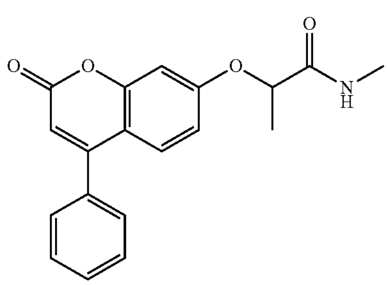 [SMILES: CNC(=O)C(C)Oc1ccc2c(-c3ccccc3)cc(=O)oc2c1] | ¹H NMR (300 MHz, Chloroform-d) δ 7.45 (dp, J = 5.6, 1.8 Hz, 3H), 7.42-7.29 (m, 3H), 6.85 (d, J = 2.6 Hz, 1H), 6.72 (dd, J = 8.9, 2.6 Hz, 1H), 6.33 (s, 1H), 6.18 (s, 1H), 4.71 (q, J = 6.7 Hz, 1H), 2.79 (d, J = 4.9 Hz, 3H), 1.55 (d, J = 6.8 Hz, 3H). | 96% |

TABLE 2-continued

Compounds of formula (I) of the invention

| | Structure | ¹H-NMR | LC purity |
|---|---|---|---|
| 27 | 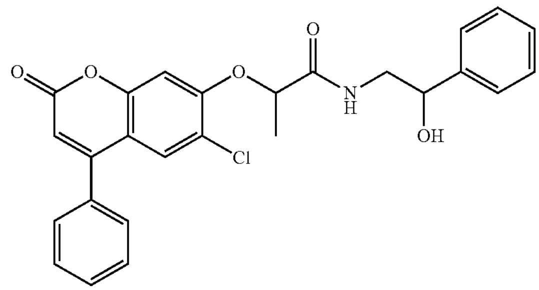 [SMILES: CC(Oc1cc2oc(=O)cc(-c3ccccc3)c2cc1Cl)C(=O)NCC(O)c1ccccc1] | ¹H NMR (300 MHz, Chloroform-d) δ 7.47 (q, J = 3.6, 3.1 Hz, 3H), 7.46-7.28 (m, 3H), 7.34-7.10 (m, 6H), 7.01 (dt, J = 11.4, 5.9 Hz, 1H), 6.81 (d, J = 12.8 Hz, 1H), 6.18 (d, J = 2.0 Hz, 1H), 4.79 (dt, J = 8.0, 4.1 Hz, 1H), 4.70 (q, J = 6.8 Hz, 1H), 3.74-3.53 (m, 1H), 3.37 (ddt, J = 13.4, 7.9, 5.5 Hz, 1H), 1.56 (t, J = 7.3 Hz, 3H). | 100% |
| 28 | 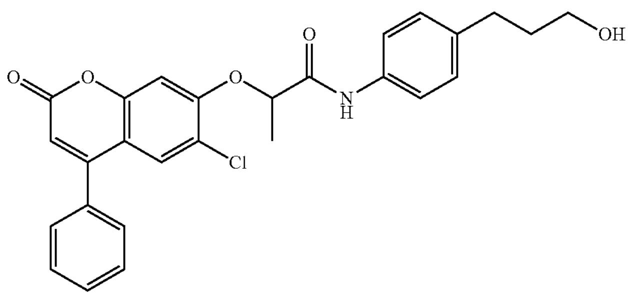 [SMILES: CC(Oc1cc2oc(=O)cc(-c3ccccc3)c2cc1Cl)C(=O)Nc1ccc(CCCO)cc1] | ¹H NMR (300 MHz, Chloroform-d) δ 8.42 (s, 1H), 7.53-7.29 (m, 8H), 7.11 (d, J = 8.2 Hz, 2H), 6.94 (s, 1H), 6.23 (s, 1H), 4.87 (q, J = 6.7 Hz, 1H), 3.59 (t, J = 6.4 Hz, 2H), 2.68-2.56 (m, 2H), 1.88-1.65 (m, 5H), OH not seen. | 100% |
| 29 | 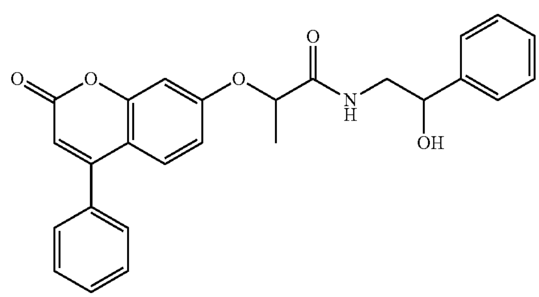 [SMILES: CC(Oc1ccc2c(-c3ccccc3)cc(=O)oc2c1)C(=O)NCC(O)c1ccccc1] | ¹H NMR (300 MHz, Chloroform-d) δ 7.45 (q, J = 3.1 Hz, 3H), 7.34 (ddt, J = 5.7, 4.2, 1.9 Hz, 3H), 7.28-7.09 (m, 5H), 6.79 (td, J = 8.8, 4.3 Hz, 2H), 6.69 (ddd, 8.6, 5.8, 2.5 Hz, 1H), 6.15 (d, J = 2.2 Hz, 1H), 4.71 (dtd, J = 25.3, 7.3, 6.8, 4.6 Hz, 2H), 3.64 (dddd, 17.2, 15.4, 8.8, 5.2 Hz, 1H), 3.43-3.24 (m, 1H), 1.52 (dd, J = 6.7, 5.6 Hz, 3H). | 98% |
| 30 | 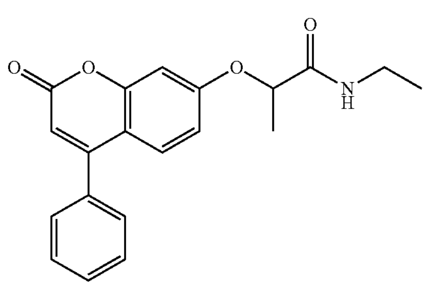 | ¹H NMR (300 MHz, Chloroform-d) δ 7.50-7.38 (m, 3H), 7.42-7.27 (m, 3H), 6.79-6.68 (m, 2H), 6.15 (s, 1H), 4.74 (q, J = 6.8 Hz, 1H), 4.17 (q, J = 7.1 Hz, 2H), 1.59 (d, J = 6.7 Hz, 3H), 1.21 (t, J = 7.1 Hz, 3H). | 95% |
| 31 | 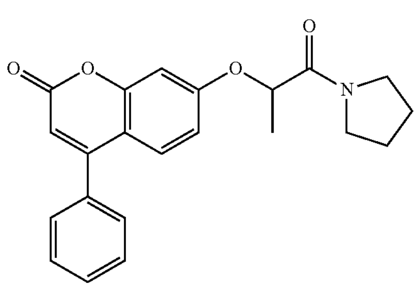 [SMILES: CC(Oc1ccc2c(-c3ccccc3)cc(=O)oc2c1)C(=O)N1CCCC1] | ¹H NMR (300 MHz, Chloroform-d) δ 7.44 (hept, J = 2.2 Hz, 3H), 7.41-7.24 (m, 3H), 6.81-6.66 (m, 2H), 6.16 (s, 1H), 4.84 (q, J = 6.7 Hz, 1H), 3.60 (dt, J = 10.4, 6.4 Hz, 1H), 3.53-3.41 (m, 1H), 3.47-3.27 (m, 2H), 2.07-1.64 (m, 4H), 1.56 (d, J = 6.7 Hz, 3H). | 98% |

TABLE 2-continued

Compounds of formula (I) of the invention

| | Structure | ¹H-NMR | LC purity |
|---|---|---|---|
| 32 | 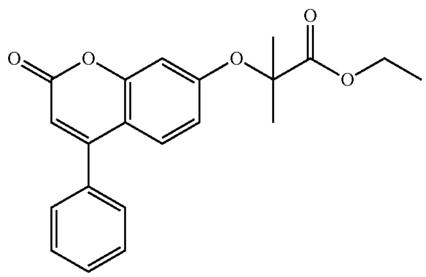 [SMILES: CCOC(=O)C(C)(C)Oc1ccc2c(-c3ccccc3)cc(=O)oc2c1] | ¹H NMR (300 MHz, Chloroform-d) δ 7.43 (dt, J = 4.5, 1.7 Hz, 3H), 7.35 (ddq, J = 4.4, 3.2, 2.0 Hz, 2H), 7.33-7.16 (m, 1H), 6.74-6.59 (m, 2H), 6.14 (d, J = 1.5 Hz, 1H), 4.25-4.10 (m, 2H), 1.59 (s, 6H), 1.24-1.12 (m, 3H). | 98% |
| 33 | 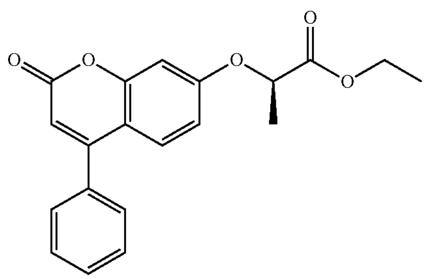 [SMILES: CCOC(=O)[C@@H](C)Oc1ccc2c(-c3ccccc3)cc(=O)oc2c1] | ¹H NMR (400 MHz, Chloroform-d) δ 7.47-7.42 (m, 3H), 7.38-7.34 (m, 2H), 7.32 (dd, J = 8.3, 0.9 Hz, 1H), 6.76-6.71 (m, 2H), 6.16 (d, J = 0.6 Hz, 1H), 4.74 (q, J = 6.8 Hz, 1H), 4.21-4.14 (m, 2H), 1.60 (dd, J = 6.7, 0.7 Hz, 3H), 1.24-1.20 (m, 3H). | 100% |
| 34 | 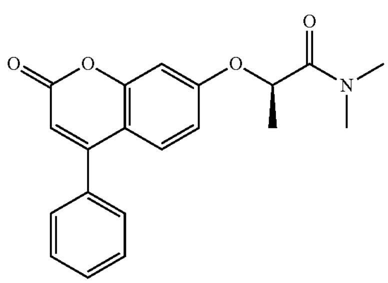 [SMILES: C[C@@H](Oc1ccc2c(-c3ccccc3)cc(=O)oc2c1)C(=O)N(C)C] | ¹H NMR (400 MHz, Chloroform-d) δ 7.48-7.40 (m, 3H), 7.40-7.27 (m, 3H), 6.76 (dd, J = 8.9, 2.6 Hz, 1H), 6.70 (d, J = 2.5 Hz, 1H), 6.15 (s, 1H), 4.99 (q, J = 6.7 Hz, 1H), 3.07 (s, 3H), 2.91 (s, 3H), 1.58 (d, J = 6.7 Hz, 3H). | 97% |
| 35 | 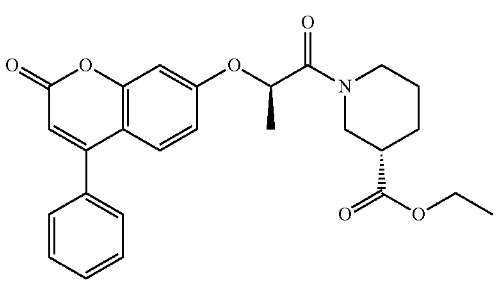 [SMILES: CCOC(=O)[C@H]1CCCN(C(=O)[C@@H](C)Oc2ccc3c(-c4ccccc4)cc(=O)oc3c2)C1] | ¹H NMR (400 MHz, DMSO-d₆) δ 7.59-7.48 (m, 5H), 7.32 (dd, J = 14.1, 9.0 Hz, 1H), 6.94 (d, J = 15.5 Hz, 1H), 6.85 (dd, J = 15.6, 9.2 Hz, 1H), 6.22 (s, 1H), 5.48-5.45 (m, 1H), 4.22-4.11 (m, 1H), 4.08-4.00 (m, 3H), 3.84-3.76 (m, 1H), 3.68-3.49 (m, 1H), 3.15 (d, J = 5.3, 3H), 2.04-1.85 (m, 1H), 1.44 (dd, J = 14.2, 6.5 Hz, 3H), 1.24-1.04 (m, 4H). | 98% |
| 36 | 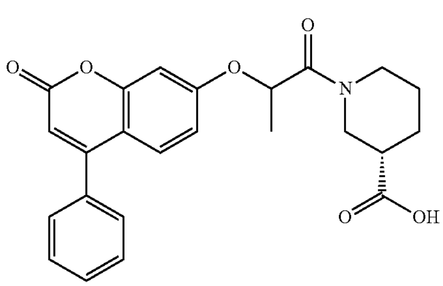 [SMILES: CC(Oc1ccc2c(-c3ccccc3)cc(=O)oc2c1)C(=O)N1CCC[C@H](C(=O)O)C1] | ¹H NMR (400 MHz, DMSO-d₆) δ 12.43 (s, 1H), 7.61-7.48 (m, 5H), 7.40-7.28 (m, 1H), 6.96 (ddd, J = 16.6, 7.7, 2.4 Hz, 1H), 6.93-6.81 (m, 1H), 6.27-6.21 (m, 1H), 5.48 (ddd, J = 22.6, 16.3, 6.6 Hz, 1H), 4.36-3.48 (m, 2H), 3.25-2.71 (m, 2H), 2.46-2.21 (m, 1H), 2.05-1.83 (m, 1H), 1.81-1.38 (m, 6H). | 95% |

TABLE 2-continued

Compounds of formula (I) of the invention

| | Structure | ¹H-NMR | LC purity |
|---|---|---|---|
| 37 | 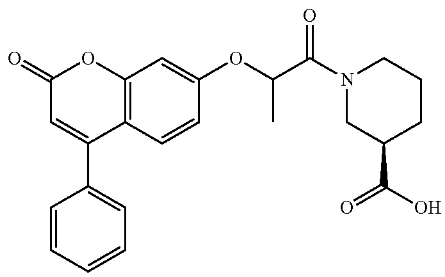 [SMILES: CC(Oc1ccc2c(-c3ccccc3)cc(=O)oc2c1)C(=O)N1CCC[C@@H](C(=O)O)C1] | ¹H NMR (400 MHz, DMSO-d₆) δ 12.39 (s, 1H), 7.60-7.47 (m, 5H), 7.38-7.27 (m, 1H), 7.01-6.80 (m, 2H), 6.22 (d, J = 3.4 Hz, 1H), 5.55-5.38 (m, 1H), 4.31-3.45 (m, 2H), 3.24-3.08 (m, 2H), 2.92-2.69 (m, 1H), 2.35-2.22 (m, 1H), 2.02-1.87 (m, 1H), 1.82-1.36 (m, 6H). | 94% |
| 38 | 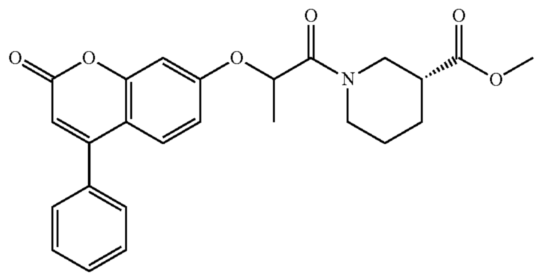 [SMILES: COC(=O)[C@@H]1CCCN(C(=O)C(C)Oc2ccc3c(-c4ccccc4)cc(=O)oc3c2)C1] | ¹H NMR (400 MHz, DMSO-d₆) δ 7.60-7.47 (m, 5H), 7.33 (t, J = 9.2 Hz, 1H), 6.99 (s, 0H), 6.96-6.80 (m, 2H), 6.22 (d, J = 1.8 Hz, 1H), 5.46 (ddt, J = 18.7, 12.6, 6.5 Hz, 1H), 4.24-3.72 (m, 2H), 3.69-3.54 (m, 3H), 3.25-2.93 (m, 1H), 2.67-2.37 (m, 2H), 2.02-1.58 (m, 3H), 1.56-1.36 (m, 4H). | 95% |
| 39 | 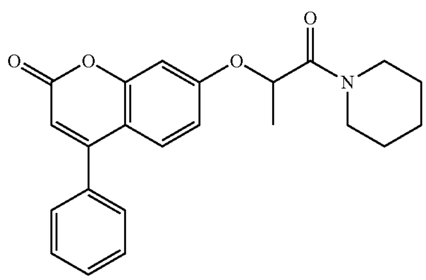 [SMILES: CC(Oc1ccc2c(-c3ccccc3)cc(=O)oc2c1)C(=O)N1CCCCC1] | ¹H NMR (400 MHz, DMSO-d₆) δ 7.60-7.47 (m, 5H), 7.37-7.29 (m, 1H), 7.01-6.81 (m, 2H), 6.22 (d, J = 0.8 Hz, 1H), 5.44 (q, J = 6.5 Hz, 1H) | 98% |
| 40 | 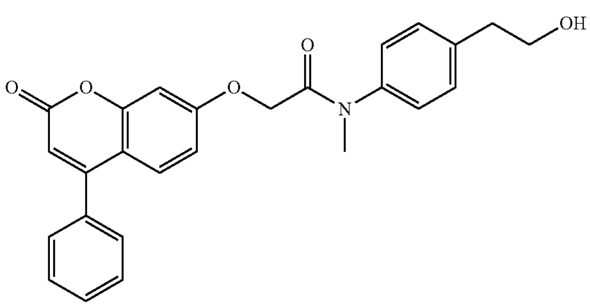 [SMILES: CN(C(=O)COc1ccc2c(-c3ccccc3)cc(=O)oc2c1)c1ccc(CCO)cc1] | ¹H NMR (400 MHz, DMSO-d₆) δ 7.58-7.46 (m, 5H), 7.38 (d, J = 8.0 Hz, 2H), 7.31 (d, J = 8.7 Hz, 3H), 6.88 (s, 1H), 6.78 (d, J = 8.7 Hz, 1H), 6.22 (d, J = 1.0 Hz, 1H), 4.66-4.55 (m, 3H), 3.61 (q, J = 6.5 Hz, 2H), 3.16 (s, 3H), 2.78-2.69 (m, 2H). | 90% |
| 41 | 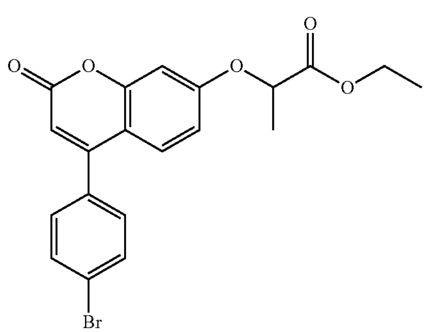 [SMILES: CCOC(=O)C(C)Oc1ccc2c(-c3ccc(Br)cc3)cc(=O)oc2c1] | ¹H NMR (400 MHz, Chloroform-d) δ 7.66 (dd, J = 8.0, 1.0 Hz, 2H), 7.36-7.23 (m, 3H), 6.85-6.77 (m, 2H), 6.21 (d, J = 0.7 Hz, 1H), 4.81 (q, J = 6.8 Hz, 1H), 4.30-4.19 (m, 2H), 1.67 (d, J = 6.8 Hz, 3H), 1.29 (td, J = 7.1, 0.8 Hz, 3H). | 98% |

TABLE 2-continued

| | Compounds of formula (I) of the invention | | |
|---|---|---|---|
| | Structure | ¹H-NMR | LC purity |
| 42 | | CAS: 900294-20-4 | 98% |
| 43 | | CAS: 380495-52-3 | 98% |
| 44 | | CAS: 314742-89-7 | 99% |
| 45 | | CAS: 500204-58-0 | 96% |
| 46 | | CAS: 380475-99-0 | 94% |

TABLE 2-continued

| | Compounds of formula (I) of the invention | | |
|---|---|---|---|
| | Structure | ¹H-NMR | LC purity |
| 47 | | CAS: 431069-80-6 | 99% |
| 48 | | CAS: 406475-53-4 | 99% |
| 49 | | CAS: 297147-97-8 | 98% |
| 50 | | CAS: 297148-30-2 | 96% |
| 51 | | CAS: 270596-08-2 | 98% |

TABLE 2-continued

Compounds of formula (I) of the invention

| | Structure | ¹H-NMR | LC purity |
|---|---|---|---|
| 52 | 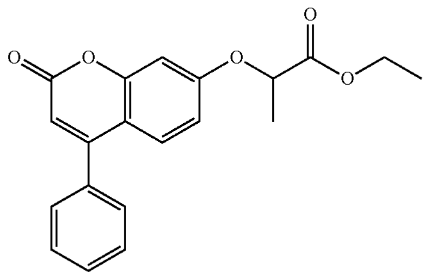 [SMILES: CCOC(=O)C(C)Oc1ccc2c(-c3ccccc3)cc(=O)oc2c1] | ¹H NMR (400 MHz, Chloroform-d) δ 7.56-7.47 (m, 3H), 7.47-7.35 (m, 3H), 6.85-6.76 (m, 2H), 6.23 (d, J = 0.6 Hz, 1H), 4.81 (q, J = 6.8 Hz, 1H), 4.24 (qd, J = 7.1, 0.6 Hz, 2H), 1.67 (dd, J = 6.8, 0.6 Hz, 3H), 1.29 (td, J = 7.2, 0.6 Hz, 3H). | 99% |
| 53 | 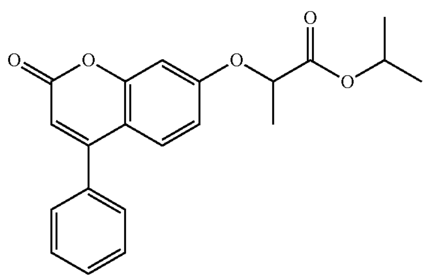 [SMILES: CC(C)OC(=O)C(C)Oc1ccc2c(-c3ccccc3)cc(=O)oc2c1] | ¹H NMR (300 MHz, Chloroform-d) δ 7.50-7.39 (m, 3H), 7.43-7.27 (m, 3H), 6.79-6.68 (m, 2H), 6.16 (s, 1H), 5.02 (hept, J = 6.3 Hz, 1H), 4.70 (q, J = 6.8 Hz, 1H), 1.58 (d, J = 6.8 Hz, 3H), 1.19 (dd, J = 23.8, 6.3 Hz, 6H). | 95% |
| 54 | 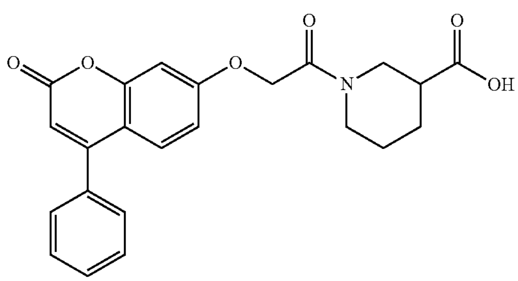 [SMILES: O=C(O)C1CCCN(C(=O)COc2ccc3c(-c4ccccc4)cc(=O)oc3c2)C1] | ¹H NMR (300 MHz, Methanol-d₄) δ 7.48-7.34 (m, 4H), 7.40-7.22 (m, 2H), 6.92-6.75 (m, 2H), 6.07 (d, J = 4.4 Hz, 1H), 5.12-4.83 (m, 2H), 3.72-3.30 (m, 3H), 3.19-2.91 (m, 1H), 2.48 (dq, J = 64.7, 5.0, 4.3 Hz, 1H), 2.05-1.36 (m, 4H). | 100% |
| 55 | 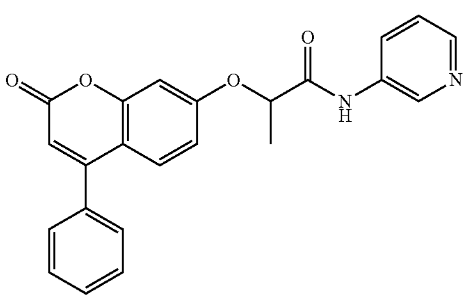 [SMILES: CC(Oc1ccc2c(-c3ccccc3)cc(=O)oc2c1)C(=O)Nc1cccnc1] | ¹H NMR (400 MHz, Chloroform-d) δ 8.61 (dd, J = 2.7, 0.8 Hz, 1H), 8.39 (dd, J = 4.8, 1.5 Hz, 1H), 8.29-8.16 (m, 2H), 7.56-7.48 (m, 3H), 7.49-7.38 (m, 3H), 7.30 (dd, J = 8.4, 4.8 Hz, 1H), 7.02 (dd, J = 2.6, 0.8 Hz, 1H), 6.88 (ddd, J = 8.9, 2.6, 0.8 Hz, 1H), 6.26 (d, J = 0.8 Hz, 1H), 4.94 (q, J = 6.8 Hz, 1H), 1.72 (dd, J = 6.8, 0.8 Hz, 3H). | 95% |
| 56 | 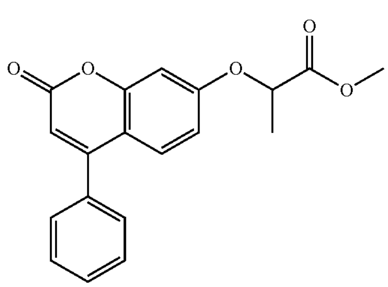 [SMILES: COC(=O)C(C)Oc1ccc2c(-c3ccccc3)cc(=O)oc2c1] | CAS: 304896-93-3 | 98% |

TABLE 2-continued

Compounds of formula (I) of the invention

| | Structure | ¹H-NMR | LC purity |
|---|---|---|---|
| 57 | (6-chloro-2-oxo-4-phenyl-2H-chromen-7-yloxy)-N-[4-(2-hydroxyethyl)phenyl]acetamide | CAS: 902040-50-0 | 96% |
| 58 | methyl 2-(6-chloro-2-oxo-4-phenyl-2H-chromen-7-yloxy)propanoate | CAS: 313471-01-1 | 83% |
| 59 | 2-(6-chloro-2-oxo-4-phenyl-2H-chromen-7-yloxy)-N-(pyridin-3-ylmethyl)acetamide | CAS: 901269-44-1 | 97% |
| 60 | 1-[2-(2-oxo-4-phenyl-2H-chromen-7-yloxy)propanoyl]piperidine-3-carboxamide | ¹H NMR (400 MHz, DMSO-d₆) δ 7.59-7.47 (m, 5H), 7.40-7.26 (m, 2H), 7.01-6.92 (m, 1H), 6.96-6.78 (m, 2H), 6.22 (d, J = 5.0 Hz, 1H), 5.57-5.36 (m, 1H), 4.36-4.17 (m, 1H), 3.98-3.80 (m, 1H), 3.38-2.82 (m, 1H), 2.74-2.07 (m, 2H), 1.97-1.79 (m, 1H), 1.70 (t, J = 16.7 Hz, 1H), 1.56 (d, J = 14.7 Hz, 1H), 1.54-1.39 (m, 3H), 1.36-1.19 (m, 1H). | 96% |
| 61 | 2-(2-oxo-4-phenyl-2H-chromen-7-yloxy)-N-(pyridin-4-yl)propanamide | ¹H NMR (400 MHz, Chloroform-d) δ 8.51-8.42 (m, 3H), 7.57-7.51 (m, 2H), 7.50-7.39 (m, 3H), 7.43-7.31 (m, 3H), 6.94 (d, J = 2.6 Hz, 1H), 6.80 (dd, J = 8.9, 2.6 Hz, 1H), 6.20 (s, 1H), 4.88 (q, J = 6.8 Hz, 1H), 1.65 (d, J = 6.7 Hz, 3H). | 93% |

TABLE 2-continued

Compounds of formula (I) of the invention

| | Structure | ¹H-NMR | LC purity |
|---|---|---|---|
| 62 | 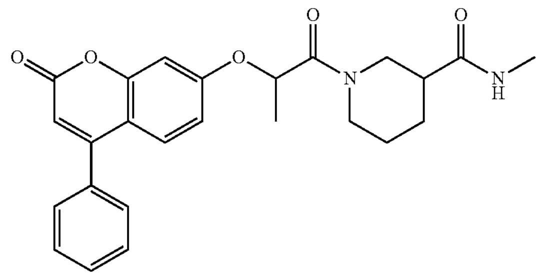 [SMILES: CNC(=O)C1CCCN(C(=O)C(C)Oc2ccc3c(-c4ccccc4)cc(=O)oc3c2)C1] | ¹H NMR (400 MHz, DMSO-d₆) δ 7.88-7.76 (m, 1H), 7.59-7.47 (m, 5H), 7.41-7.26 (m, 1H), 7.00-6.89 (m, 1H), 6.89-6.81 (m, 1H), 6.26-6.19 (m, 1H), 5.57-5.33 (m, 6.5 Hz, 1H), 4.30-4.20 (m, 1H), 3.98-3.77 (m, 1H), 3.43-2.84 (m, 1H), 2.74-2.43 (m, 4H), 2.42-1.78 (m, 1H), 1.78-1.67 (m, 1H), 1.67-1.56 (m, 1H), 1.49-1.39 (m, 3H), 1.35-1.19 (m, 2H). | 95% |
| 63 | 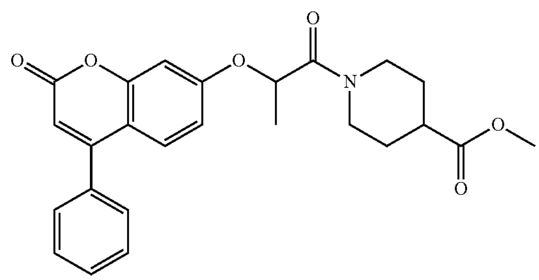 [SMILES: COC(=O)C1CCN(C(=O)C(C)Oc2ccc3c(-c4ccccc4)cc(=O)oc3c2)CC1] | ¹H NMR (400 MHz, DMSO-d₆) δ 7.59-7.47 (m, 5H), 7.33 (d, J = 8.9 Hz, 1H), 6.93 (d, J = 13.9 Hz, 1H), 6.85 (d, J = 9.0 Hz, 1H), 6.23 (d, J = 0.5 Hz, 1H), 5.45 (dd, J = 12.9, 6.7 Hz, 1H), 4.16 (s, 1H), 3.93 (d, J = 13.6 Hz, 1H), 3.60 (d, J = 4.5 Hz, 3H), 3.28-3.24 (m, 1H), 3.20-2.57 (m, 2H), 1.85 (s, 2H), 1.67-1.34 (m, 5H). | 98% |
| 64 | 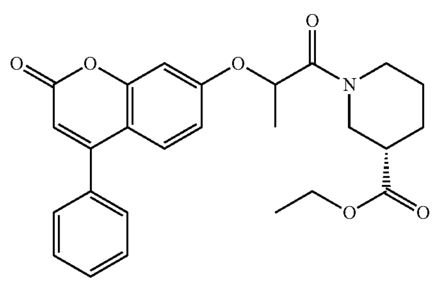 [SMILES: CCOC(=O)[C@H]1CCCN(C(=O)C(C)Oc2ccc3c(-c4ccccc4)cc(=O)oc3c2)C1] | ¹H NMR (400 MHz, DMSO-d₆) δ 7.59-7.46 (m, 5H), 7.38-7.27 (m, 1H), 7.05-6.79 (m, 2H), 6.25-6.20 (m, 1H), 5.47 (ddd, J = 21.6, 16.8, 6.6 Hz, 1H), 4.24-3.91 (m, 3H), 3.84-3.49 (m, 1H), 3.26-3.16 (m, 1H), 3.13-2.98 (m, 1H), 2.80-2.36 (m, 1H), 2.02-1.84 (m, 1H), 1.80-1.32 (m, 5H), 1.23-1.03 (m, 4H). | 90% |
| 65 | 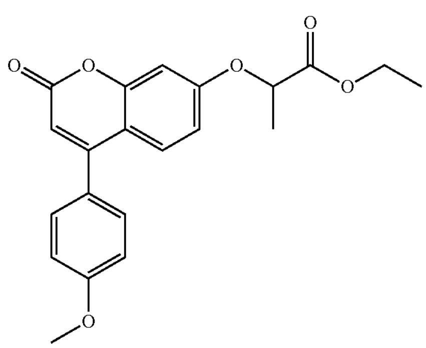 [SMILES: CCOC(=O)C(C)Oc1ccc2c(-c3ccc(OC)cc3)cc(=O)oc2c1] | CAS: 270596-07-1 | 100% |
| 66 | 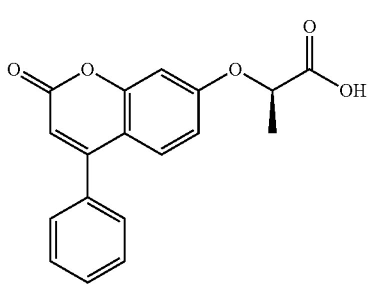 [SMILES: C[C@@H](Oc1ccc2c(-c3ccccc3)cc(=O)oc2c1)C(=O)O] | ¹H NMR (400 MHz, DMSO-d₆) δ 13.13 (s, 1H), 7.59-7.46 (m, 5H), 7.33 (d, J = 8.9 Hz, 1H), 6.97 (d, J = 2.5 Hz, 1H), 6.89 (dd, J = 8.9, 2.5 Hz, 1H), 6.23 (s, 1H), 5.05 (q, J = 6.8 Hz, 1H), 1.52 (d, J = 6.9 Hz, 3H). | 99% |

TABLE 2-continued

Compounds of formula (I) of the invention

| | Structure | ¹H-NMR | LC purity |
|---|---|---|---|
| 67 | 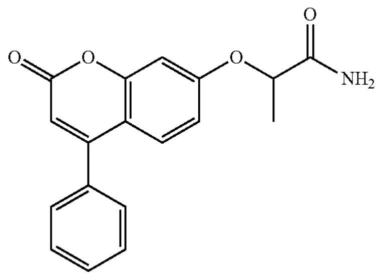 [SMILES: CC(Oc1ccc2c(-c3ccccc3)cc(=O)oc2c1)C(N)=O] | ¹H NMR (300 MHz, DMSO-d₆) δ 7.71 (s, 1H), 7.616-7.57 (m, 5H), 7.47-7.36 (m, 2H), 7.09-6.93 (m, 2H), 6.31 (d, J = 4.4 Hz, 1H), 4.89 (q, J = 6.7 Hz, 1H), 1.54 (d, J = 6.3 Hz, 3H). | 95% |
| 68 | 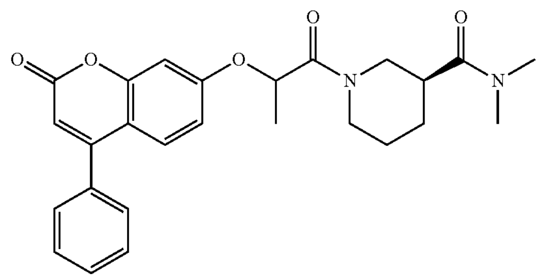 [SMILES: CC(Oc1ccc2c(-c3ccccc3)cc(=O)oc2c1)C(=O)N1CCC[C@H](C(=O)N(C)C)C1] | ¹H NMR (400 MHz, DMSO-d₆) δ 7.59-7.47 (m, 5H), 7.39-7.29 (m, 1H), 7.02-6.92 (m, 1H), 6.86 (t, J = 9.4 Hz, 1H), 6.23 (s, 1H), 5.57-5.39 (m, 1H), 4.39-4.12 (m, 1H), 3.92 (s, 1H), 3.24-2.95 (m, 4H), 2.83-2.75 (m, 5H), 2.74-2.53 (m, 1H), 1.95-1.50 (m, 2H), 1.48-1.39 (m, 4H). | 92% |
| 69 | 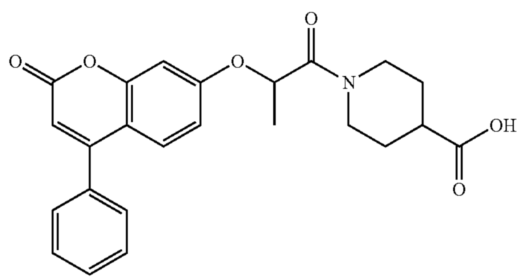 [SMILES: CC(Oc1ccc2c(-c3ccccc3)cc(=O)oc2c1)C(=O)N1CCC(C(=O)O)CC1] | ¹H NMR (400 MHz, DMSO-d₆) δ 7.59-7.47 (m, 5H), 7.33 (d, J = 9.2 Hz, 1H), 6.93 (d, J = 17.0 Hz, 1H), 6.85 (d, J = 9.1 Hz, 1H), 6.22 (s, 1H), 5.49-5.40 (m, 1H), 4.14 (s, 1H), 3.92 (d, J = 13.8 Hz, 1H), 3.14 (s, 2H), 2.78 (dt, J = 28.7, 14.1 Hz, 1H), 1.83 (s, 2H), 1.64-1.31 (m, 5H). | 92% |
| 70 | 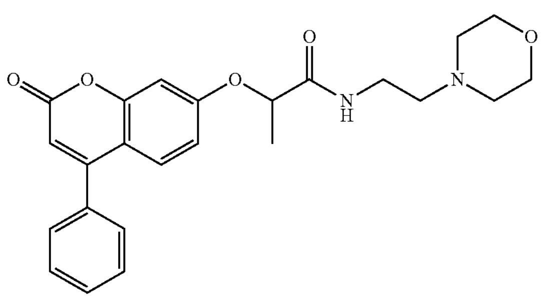 [SMILES: CC(Oc1ccc2c(-c3ccccc3)cc(=O)oc2c1)C(=O)NCCN1CCOCC1] | ¹H NMR (300 MHz, Chloroform-d) δ 7.50-7.40 (m, 3H), 7.45-7.28 (m, 3H), 6.89-6.69 (m, 3H), 6.18 (s, 1H), 4.69 (q, J = 6.7 Hz, 1H), 3.61-3.40 (m, 4H), 3.39-3.19 (m, 2H), 2.50-2.16 (m, 6H), 1.57 (d, J = 6.7 Hz, 3H). | 99% |
| 71 | 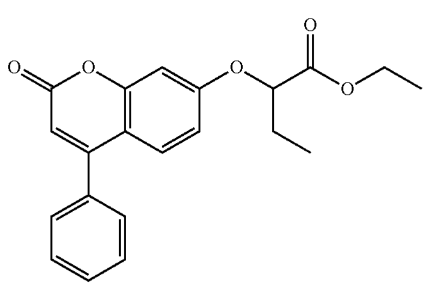 [SMILES: CCOC(=O)C(CC)Oc1ccc2c(-c3ccccc3)cc(=O)oc2c1] | ¹H NMR (400 MHz, Chloroform-d) δ 7.55-7.35 (m, 6H), 6.85-6.77 (m, 2H), 6.23 (s, 1H), 4.62 (t, J = 6.1 Hz, 1H), 4.24 (qd, J = 7.1, 1.1 Hz, 2H), 2.10-1.98 (m, 2H), 1.28 (td, J = 7.1, 1.0 Hz, 3H), 1.10 (td, J = 7.4, 1.0 Hz, 3H). | 99% |

TABLE 2-continued

Compounds of formula (I) of the invention

| | Structure | ¹H-NMR | LC purity |
|---|---|---|---|
| 72 | 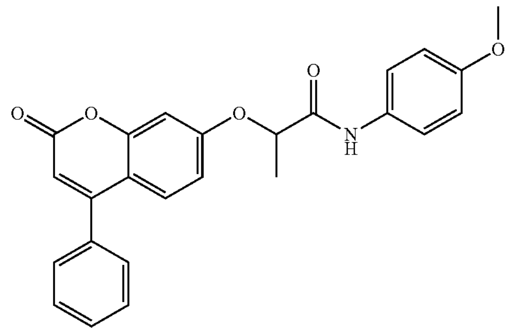 [SMILES: COc1ccc(NC(=O)C(C)Oc2ccc3c(-c4ccccc4)cc(=O)oc3c2)cc1] | CAS: 370583-75-8 | 100% |
| 73 | 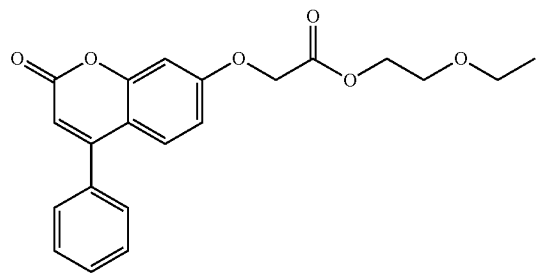 [SMILES: CCOCCOC(=O)COc1ccc2c(-c3ccccc3)cc(=O)oc2c1] | CAS: 449740-01-6 | 95% |
| 74 | 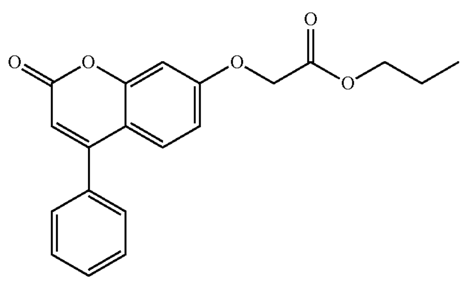 [SMILES: CCCOC(=O)COc1ccc2c(-c3ccccc3)cc(=O)oc2c1] | CAS: 449739-27-9 | 99% |
| 75 | 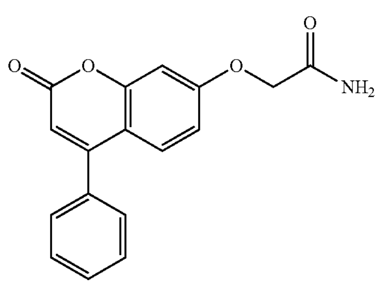 [SMILES: NC(=O)COc1ccc2c(-c3ccccc3)cc(=O)oc2c1] | ¹H NMR (300 MHz, DMSO-$d_6$) δ 7.63 (s, 1H), 7.60-7.53 (m, 5H), 7.48-7.32 (m, 2H), 7.10-6.93 (m, 2H), 6.26 (d, J = 1.7 Hz, 1H), 4.59 (s, 2H). | 95% |
| 76 | 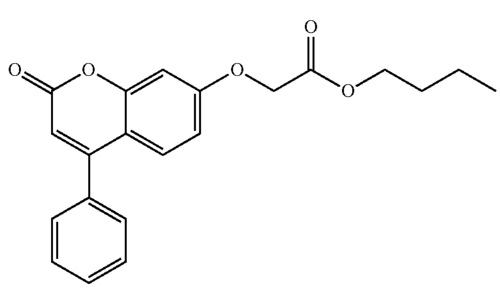 [SMILES: CCCCOC(=O)COc1ccc2c(-c3ccccc3)cc(=O)oc2c1] | CAS: 302939-33-9 | 100% |

TABLE 2-continued

Compounds of formula (I) of the invention

| # | Structure | ¹H-NMR | LC purity |
|---|---|---|---|
| 77 | [4-phenyl-coumarin-7-yloxy-acetic acid isobutyl ester] | CAS: 449739-26-8 | 99% |
| 78 | [6-chloro-4-phenyl-coumarin-7-yloxy-acetyl-3,4-dihydroquinoline] | CAS: 380324-70-9 | 96% |
| 79 | [6-chloro-4-phenyl-coumarin-7-yloxy-2-methyl-N-(2-morpholinoethyl)acetamide] | ¹H NMR (300 MHz, Chloroform-d) δ 7.53-7.40 (m, 4H), 7.38-7.32 (m, 2H), 7.23-7.12 (m, 1H), 6.87 (s, 1H), 6.22 (s, 1H), 4.77 (q, J = 6.7 Hz, 1H), 3.56 (dt, J = 7.3, 3.7 Hz, 4H), 3.34 (p, J = 5.4 Hz, 2H), 2.53-2.24 (m, 6H), 1.63 (d, J = 6.6 Hz, 3H). | 98% |
| 80 | [5-fluoro-4-phenyl-coumarin-7-yloxy-2-methyl-N,N-dimethylacetamide] | ¹H NMR (400 MHz, Chloroform-d) δ 7.43-7.31 (m, 3H), 7.36-7.24 (m, 2H), 6.57-6.41 (m, 2H), 6.05 (s, 1H), 4.97 (q, J = 6.7 Hz, 1H), 3.07 (s, 3H), 2.92 (s, 3H), 1.57 (d, J = 6.7 Hz, 3H). | 98% |
| 81 | [4-phenyl-coumarin-7-yloxy-acetic acid ethyl ester] | ¹H NMR (400 MHz, Chloroform-d) δ 7.51 (q, J = 2.6 Hz, 3H), 7.47-7.37 (m, 3H), 6.88-6.80 (m, 2H), 6.24 (q, J = 0.9 Hz, 1H), 4.69 (s, 2H), 4.34-4.24 (m, 2H), 1.37-1.27 (m, 3H). | 97% |

TABLE 2-continued

Compounds of formula (I) of the invention

| | Structure | $^1$H-NMR | LC purity |
|---|---|---|---|
| 82 | 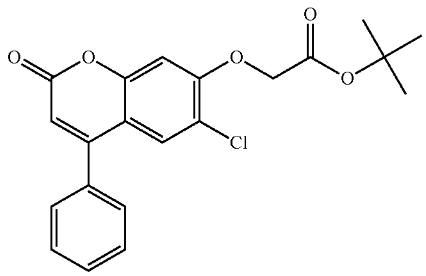 [SMILES: CC(C)(C)OC(=O)COc1cc2oc(=O)cc(-c3ccccc3)c2cc1Cl] | CAS: 307547-54-2 | 98% |
| 83 | 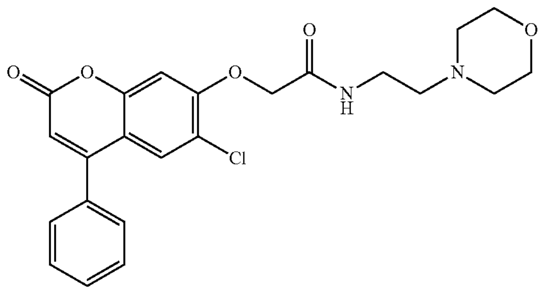 [SMILES: O=C(COc1cc2oc(=O)cc(-c3ccccc3)c2cc1Cl)NCCN1CCOCC1] | CAS: 901271-61-2 | 99% |
| 84 | 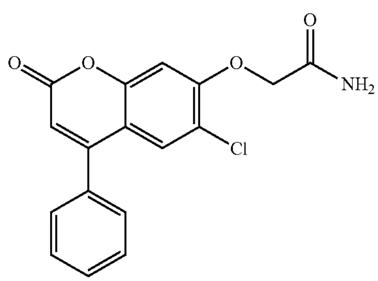 [SMILES: NC(=O)COc1cc2oc(=O)cc(-c3ccccc3)c2cc1Cl] | CAS: 307547-55-3 | 96% |
| 85 | 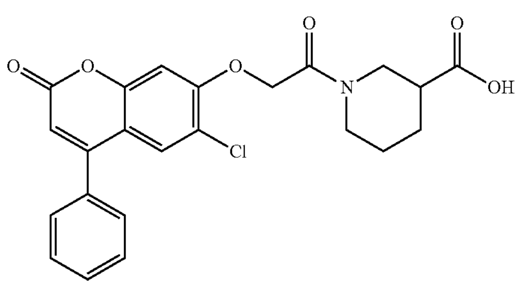 [SMILES: O=C(O)C1CCCN(C(=O)COc2cc3oc(=O)cc(-c4ccccc4)c3cc2Cl)C1] | CAS: 929807-99-8 | 98% |
| 86 | 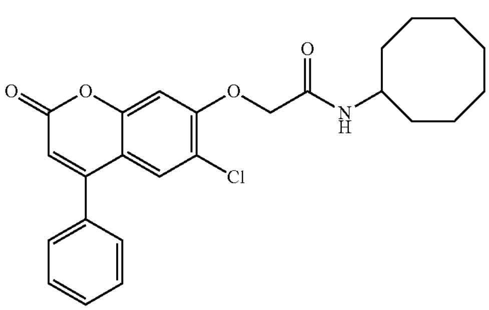 [SMILES: O=C(COc1cc2oc(=O)cc(-c3ccccc3)c2cc1Cl)NC1CCCCCCC1] | CAS: 380495-51-2 | 97% |

TABLE 2-continued

Compounds of formula (I) of the invention

| | Structure | ¹H-NMR | LC purity |
|---|---|---|---|
| 87 | 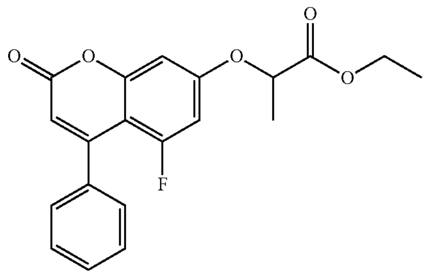 [SMILES: CCOC(=O)C(C)Oc1cc(F)c2c(-c3ccccc3)cc(=O)oc2c1] | ¹H NMR (400 MHz, Chloroform-d) δ 7.50-7.38 (m, 3H), 7.40-7.31 (m, 2H), 6.64 (dd, J = 2.5, 1.4 Hz, 1H), 6.56-6.47 (m, 1H), 6.13 (s, 1H), 4.78 (q, J = 6.8 Hz, 1H), 4.25 (q, J = 7.1 Hz, 2H), 1.66 (dd, J = 6.8, 0.9 Hz, 3H), 1.30 (td, J = 7.1, 0.9 Hz, 3H). | 100% |
| 88 | 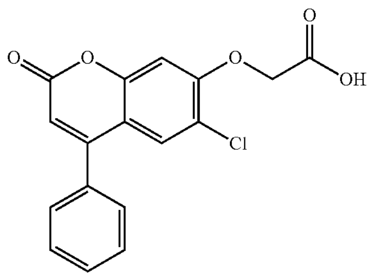 [SMILES: O=C(O)COc1cc2oc(=O)cc(-c3ccccc3)c2cc1Cl] | CAS: 130181-10-1 | 95% |
| 89 | 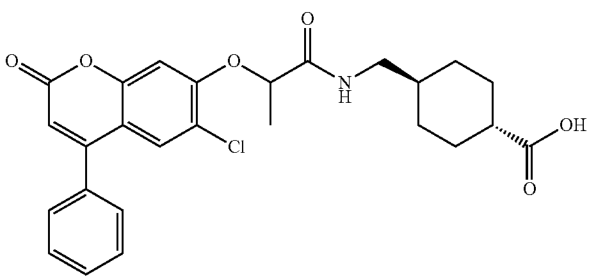 [SMILES: CC(Oc1cc2oc(=O)cc(-c3ccccc3)c2cc1Cl)C(=O)NC[C@H]1CC[C@H](C(=O)O)CC1] | CAS: 1212452-55-5 | 95% |
| 90 | 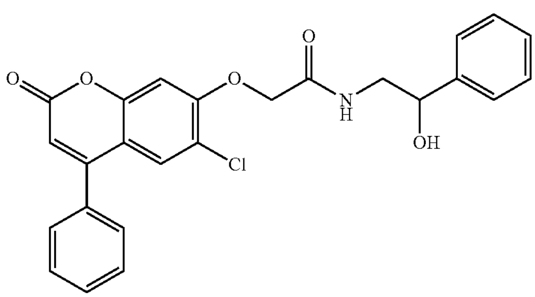 [SMILES: O=C(COc1cc2oc(=O)cc(-c3ccccc3)c2cc1Cl)NCC(O)c1ccccc1] | CAS: 879761-26-9 | 98% |
| 91 | 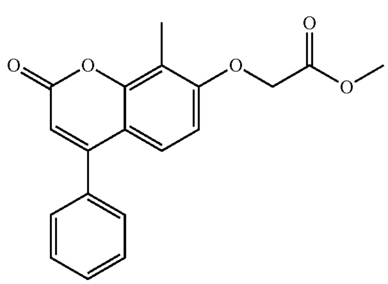 [SMILES: COC(=O)COc1ccc2c(-c3ccccc3)cc(=O)oc2c1C] | CAS: 307547-30-4 | 97% |

TABLE 2-continued

Compounds of formula (I) of the invention

| | Structure | ¹H-NMR | LC purity |
|---|---|---|---|
| 92 | 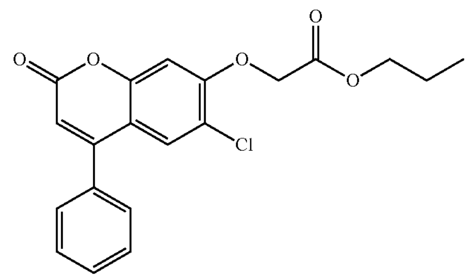 [SMILES: CCCOC(=O)COc1cc2oc(=O)cc(-c3ccccc3)c2cc1Cl] | CAS: 431939-13-8 | 98% |
| 93 | 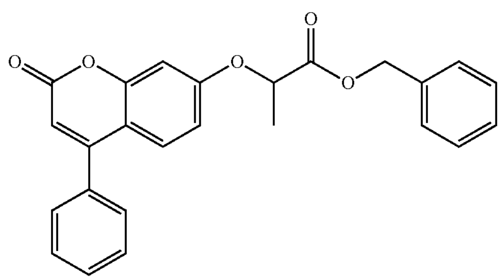 [SMILES: CC(Oc1ccc2c(-c3ccccc3)cc(=O)oc2c1)C(=O)OCc1ccccc1] | CAS: 449740-99-2 | 95% |
| 94 | 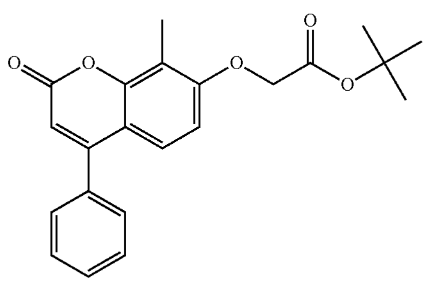 [SMILES: Cc1c(OCC(=O)OC(C)(C)C)ccc2c(-c3ccccc3)cc(=O)oc12] | CAS: 307547-33-7 | 98% |
| 95 | 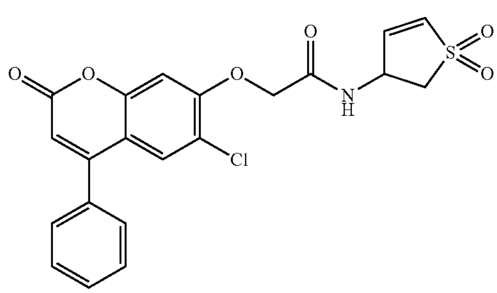 [SMILES: O=C(COc1cc2oc(=O)cc(-c3ccccc3)c2cc1Cl)NC1C=CS(=O)(=O)C1] | CAS: 921115-51-7 | 97% |
| 96 | 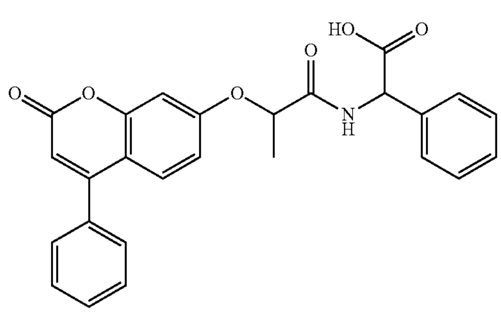 [SMILES: CC(Oc1ccc2c(-c3ccccc3)cc(=O)oc2c1)C(=O)NC(C(=O)O)c1ccccc1] | CAS: 353273-86-6 | 94% |

TABLE 2-continued

Compounds of formula (I) of the invention

| | Structure | ¹H-NMR | LC purity |
|---|---|---|---|
| 97 | 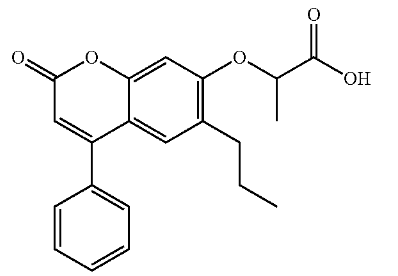 [SMILES: CCCc1cc2c(-c3ccccc3)cc(=O)oc2cc1OC(C)C(=O)O] | CAS: 314743-33-4 | 100% |
| 98 | 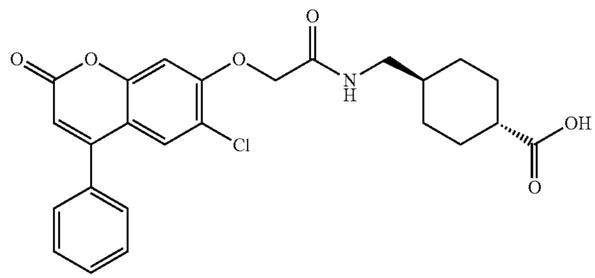 [SMILES: O=C(COc1cc2oc(=O)cc(-c3ccccc3)c2cc1Cl)NC[C@H]1CC[C@H](C(=O)O)CC1] | CAS: 1212416-54-0 | 98% |
| 99 | 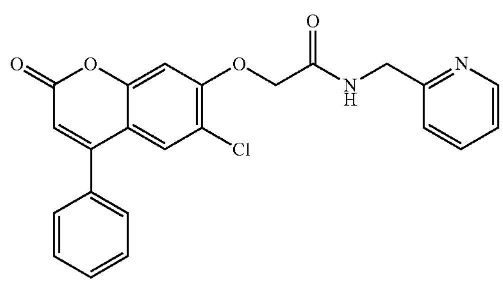 [SMILES: O=C(COc1cc2oc(=O)cc(-c3ccccc3)c2cc1Cl)NCc1ccccn1] | CAS: 900898-27-3 | 99% |

The IUPAC chemical names for the compounds shown in Table 2 are provided in Table 3 below.

4. Homogeneous TR-FRET Assay for HTS and Activity Determination

The TR-FRET assay was basically conducted as described in WO 2016/193231A1, especially as described in example 1 (hereby incorporated by reference). With respect to the background of the mitochondrial transcription it is referred to Falkenberg et al. (2002) and Posse et al. (Posse et al. 2015). The method monitors the activity of mitochondrial RNA-polymerase via detection of the formation of its product, a 407 bp long RNA sequence. Detection of the product is facilitated by hybridization of two DNA-oligonucleotide probes to specific and adjacent sequences within the RNA product sequence. Upon annealing of the probes, two fluorophores that are coupled directly to an acceptor nucleotide probe (ATT0647, 5') or introduced via a coupled streptavidin interacting with a biotinylated donor nucleotide probe on the other side (Europium cryptate, 3) are brought into sufficient proximity to serve as a fluorescence-donor-acceptor pair as generally described in Walters and Namchuk (2003). Thus, a FRET signal at 665 nm is generated upon excitation at 340 nm.

Briefly, the protocol described here was applied for screening and activity determination in a low-volume 384-well microtiter plate with non-binding surface. For high-throughput application in the 1536-well microtiter plate format, volumes of the reagent mixes were adjusted, maintaining the volumetric ratio. Proteins POLRMT (NM_172551.3), TFAM (NM_009360.4) and TFB2M (NM_008249.4) were diluted from their stocks to working concentrations of 150 nM, 1.8 µM and 330 nM respectively, in a dilution buffer containing 100 mM Tris-HCl pH 8.0, 200 mM NaCl, 10% (v/v) glycerole, 2 mM glutathione (GSH), 0.5 mM EDTA and 0.1 mg/mL BSA. Protein dilutions and template DNA, comprising a pUC18 plasmid encoding the mitochondrial light strand promoter, restriction linearized proximal to the promoter 3'-end (pUC-LSP), were mixed at the twofold final assay-concentration in a reaction buffer, containing 10 mM Tris-HCl pH 7.5, 10 mM MgCl$_2$, 40 mM NaCl, 2 mM GSH, 0.01% (w/v) Tween-20 and 0.1 mg/mL BSA.

5 µL of this mix were dispensed, depending on the chosen microtiter plate format, using multi-channel pipettes or a Multidrop® dispenser (Thermo Fisher Scientific, Waltham Mass.) into the wells of a microtiter plate and incubated at room temperature (RT) for 10 min. Chemical compounds under scrutiny in the assay were applied using contact-free acoustic droplet-dispensing (Echo520® Labcyte Inc., Sunnyvale Calif.) from 10 mM compound stocks in 100% DMSO, to a final concentration of 10 µM or in serial dilution series of the required concentration range. Equal amounts of DMSO without any compound were added to positive control samples, followed by an incubation step at RT for 10 min.

The enzymatic reaction was started by the addition of 5 µL of a mix of dNTPs in reaction buffer to a final concentration of 500 µM each. No nucleotide mix was added to negative control samples. The content of the wells was mixed using a VarioTeleshaker™ (Thermo Fisher Scientific, Waltham Mass.) at 1500 rpm for 45 sec after which the microtiter plate was centrifuged at 500×g for 1 min. The samples were incubated for 2 h at RT with humidity control to avoid evaporation. The detection reagents were prepared in a buffer that was composed, such that the enzymatic reaction was terminated due to chelating of Mg-ions and increased ionic strength, containing 50 mM Tris-HCl pH 7.5, 700 mM NaCl, 20 mM EDTA, and 0.01% (w/v) Tween-20. Importantly Eu-cryptate-coupled streptavidin had to be preincubated with a 100-fold molar excess of a random sequence oligonucleotide for 10 min at RT in the dark to block unspecific binding of single stranded RNA to the protein. Subsequently, the blocked streptavidin(-Eu) was mixed with the DNA-probes on ice and kept away from light until use.

At the end of the enzymatic reaction time 10 µL detection reagent mix was added, such that the final concentration of fluorescent-donor probe (bio-5'-AACACATCTCT(bio)GC-CAAACCCCA-bio-3'), fluorescent-acceptor probe (ATTO647N-5'-ACAAAGAACCCTAACACCAG-3') and streptavidin(-Eu) in each assay well was 1 nM, 3 nM, and 1 nM respectively. Assay plates were again mixed and centrifuged as above and stored at RT, protected from light for at least 2 h or until binding of the DNA probes to RNA product and binding of streptavidin(-Eu) to the biotinylated DNA probe led to the development of the maximal FRET signal. The generated signal was measured with an EnVision plate reader, including TRF light unit (Perkin Elmer, Waltham Mass.), using excitation at 320 nm, an integration time of 200 µs and a delay time of 100 µs, prior to detection at 620 nm and 665 nm. The ratio of donor- and acceptor-fluorescence was used to assess the specific FRET signal, as a measure of the generated product content (i.e. enzymatic activity).

5. Quantitative Real Time-PCR to Assess Cellular Activity

Quantitative real-time PCR (qRT-PCR), based on the TaqMan™ (Thermo Fisher Scientific, Waltham Mass.) technology, was carried out essentially as described in (Heid et al. 1996). HeLa cells were plated one day before compound treatment in RPMI medium supplemented with 10% Fetal Calf Serum and 2 mM L-glutamine. Cells were incubated with dilution series of compounds or vehicle (DMSO) for 4 h, prior to harvest and extraction of the RNA using the RNeasy Mini Kit (Qiagen, Hilden D), according to the manufacturer's instructions. RNA concentrations were measured spectroscopically, using a NanoDrop-2000 (Thermo Fisher Scientific, Waltham Mass.) and normalized prior to cDNA synthesis, using a 'High-Capacity cDNA Reverse Transcription Kit' (Thermo Fisher Scientific, Waltham Mass.). qRT-PCR was carried out using the 'TaqMan Fast Advance Master Mix' (Thermo Fisher Scientific, Waltham Mass.) on a 7500 Fast Real-Time PCR machine (Applied Biosystems, Foster City Calif.)

For these measurements, three genes were used to compare the effect of the scrutinized compounds in relation to their concentration. The POLRMT-gene was used to detect potential influences on nuclear transcription. Mitochondrial transcription in vivo was monitored by measurements 7S RNA. The TBP (TATA-box binding protein) gene was employed as the control (housekeeping gene) during qRT-PCR. The short-lived mitochondrial 7S RNA, which is not post-transcriptionally stabilized, allowed us to monitor rapid changes in mitochondrial transcription activity following compound addition. Biological triplicates were analyzed using the comparative CT Method ($\Delta\Delta Ct$) method (Bubner et al. 2004) and reported as Rq % values (Rq=Relative quantification=2-$\Delta\Delta Ct$).

6. Biological Activities of Compounds

Activities of compounds are listed in Table 3 together with compound number and IUPAC names as determined by the homogeneous TR-FRET assay for mitochondrial transcription activity according to Example 4 and the quantitative real time-PCR assay of inhibition of mitochondrial transcription according to Example 5 were grouped according to the following scheme:

|  | <20 nM | 20 nM ≤ x < 100 nM | 100 nM ≤ x < 1 µM | 1 µM ≤ x < 10 µM |
|---|---|---|---|---|
| mitochondrial transcription activity (IC-50) | +++ | ++ | + | (+) |

|  | <10 nM | 10 nM ≤ x < 50 nM | 50 nM ≤ x < 500 nM | 500 nM ≤ x < 10 µM |
|---|---|---|---|---|
| cellular qPCR assay IMT (IC-50) | +++ | ++ | + | (+) |

TABLE 3

IUPAC chemical names and biological activities

| IUPAC Name | mitochondrial transcription activity | cellular qPCR assay |
|---|---|---|
| 1 tert-butyl 2-(2-oxo-4-phenyl-chromen-7-yl)oxypropanoate | + | +++ |
| 2 N,N-dimethyl-2-(2-oxo-4-phenyl-chromen-7-yl)oxy-propanamide | + | ++ |
| 3 ethyl 2-[4-(4-chlorophenyl)-2-oxo-chromen-7-yl]oxypropanoate | + |  |
| 4 ethyl 2-[4-(3-chlorophenyl)-2-oxo-chromen-7-yl]oxypropanoate | + |  |
| 5 N-[4-(3-hydroxypropyl)phenyl]-2-(2-oxo-4-phenyl-chromen-7-yl)oxy-propanamide | + |  |
| 6 2-(2-oxo-4-phenyl-chromen-7-yl)oxy-N-(2-pyridyl)propanamide | + |  |
| 7 ethyl 2-[4-(3-fluorophenyl)-2-oxo-chromen-7-yl]oxypropanoate | ++ | ++ |
| 8 ethyl 2-[4-(4-fluorophenyl)-2-oxo-chromen-7-yl]oxypropanoate | + |  |
| 9 ethyl 2-[2-oxo-4-(p-tolyl)chromen-7-yl]oxypropanoate | + |  |
| 10 methyl 1-[2-(6-chloro-2-oxo-4-phenyl-chromen-7-yl)oxypropanoyl]piperidine-3-carboxylate | + |  |
| 11 2-(6-chloro-2-oxo-4-phenyl-chromen-7-yl)oxy-N-(2-pyridyl)propanamide | + |  |
| 12 N-isopropyl-2-(2-oxo-4-phenyl-chromen-7-yl)oxy-propanamide | + | + |
| 13 1-[2-(6-chloro-2-oxo-4-phenyl-chromen-7-yl)oxypropanoyl]piperidine-3-carboxylic acid | + |  |
| 14 1-[2-(2-oxo-4-phenyl-chromen-7-yl)oxypropanoyl]piperidine-3-carboxylic acid | + |  |

TABLE 3-continued

IUPAC chemical names and biological activities

| | IUPAC Name | mitochondrial transcription activity | cellular qPCR assay |
|---|---|---|---|
| 15 | methyl 1-[2-(2-oxo-4-phenyl-chromen-7-yl)oxypropanoyl]piperidine-3-carboxylate | + | + |
| 16 | N-[4-(2-hydroxyethyl)phenyl]-2-(2-oxo-4-phenyl-chromen-7-yl)oxy-propanamide | + | |
| 17 | 2-(6-chloro-2-oxo-4-phenyl-chromen-7-yl)oxy-N-[4-(2-hydroxyethyl)phenyl]propanamide | + | |
| 18 | N-[4-(2-hydroxyethyl)phenyl]-N-methyl-2-(2-oxo-4-phenyl-chromen-7-yl)oxy-propanamide | + | |
| 19 | 1-[2-(2-oxo-4-phenyl-chromen-7-yl)oxypropanoyl]piperidine-3-carbonitrile | +++ | +++ |
| 20 | 7-[1-methyl-2-oxo-2-[3-(2H-tetrazol-5-yl)-1-piperidyl]ethoxy]-4-phenyl-chromen-2-one | +++ | |
| 21 | (3S)-1-[(2R)-2-(2-oxo-4-phenyl-chromen-7-yl)oxypropanoyl]piperidine-3-carboxylic acid | + | |
| 22 | 2-(2-oxo-4-phenyl-chromen-7-yl)oxy-N-(2-pyridyl)acetamide | + | |
| 23 | methyl 1-[2-(2-oxo-4-phenyl-chromen-7-yl)oxyacetyl]piperidine-3-carboxylate | (+) | |
| 24 | phenyl 2-(2-oxo-4-phenyl-chromen-7-yl)oxypropanoate | (+) | |
| 25 | 2-(2-oxo-4-phenyl-chromen-7-yl)oxy-N-phenyl-propanamide | + | |
| 26 | N-methyl-2-(2-oxo-4-phenyl-chromen-7-yl)oxy-propanamide | + | |
| 27 | 2-(6-chloro-2-oxo-4-phenyl-chromen-7-yl)oxy-N-(2-hydroxy-2-phenyl-ethyl)propanamide | (+) | |
| 28 | 2-(6-chloro-2-oxo-4-phenyl-chromen-7-yl)oxy-N-[4-(3-hydroxypropyl)phenyl]propanamide | + | |
| 29 | N-(2-hydroxy-2-phenyl-ethyl)-2-(2-oxo-4-phenyl-chromen-7-yl)oxy-propanamide | (+) | |
| 30 | N-ethyl-2-(2-oxo-4-phenyl-chromen-7-yl)oxy-propanamide | (+) | + |
| 31 | 7-(1-methyl-2-oxo-2-pyrrolidin-1-yl-ethoxy)-4-phenyl-chromen-2-one | + | + |
| 32 | ethyl 2-methyl-2-(2-oxo-4-phenyl-chromen-7-yl)oxy-propanoate | + | ++ |
| 33 | ethyl (2R)-2-(2-oxo-4-phenyl-chromen-7-yl)oxypropanoate | + | +++ |
| 34 | (2R)-N,N-dimethyl-2-(2-oxo-4-phenyl-chromen-7-yl)oxy-propanamide | + | ++ |
| 35 | ethyl (3S)-1-[(2R)-2-(2-oxo-4-phenyl-chromen-7-yl)oxypropanoyl]piperidine-3-carboxylate | + | |
| 36 | (3S)-1-[2-(2-oxo-4-phenyl-chromen-7-yl)oxypropanoyl]piperidine-3-carboxylic acid | + | |
| 37 | (3R)-1-[2-(2-oxo-4-phenyl-chromen-7-yl)oxypropanoyl]piperidine-3-carboxylic acid | (+) | |
| 38 | methyl (3R)-1-[2-(2-oxo-4-phenyl-chromen-7-yl)oxypropanoyl]piperidine-3-carboxylate | (+) | |
| 39 | 7-[1-methyl-2-oxo-2-(1-piperidyl)ethoxy]-4-phenyl-chromen-2-one | + | |
| 40 | N-[4-(2-hydroxyethyl)phenyl]-N-methyl-2-(2-oxo-4-phenyl-chromen-7-yl)oxy-acetamide | + | |
| 41 | ethyl 2-[4-(4-bromophenyl)-2-oxo-chromen-7-yl]oxypropanoate | + | |
| 42 | 2-(6-chloro-2-oxo-4-phenyl-chromen-7-yl)oxy-N-(2-furylmethyl)propanamide | + | |
| 43 | ethyl 1-[2-(2-oxo-4-phenyl-chromen-7-yl)oxyacetyl]piperidine-3-carboxylate | (+) | |
| 44 | tert-butyl 2-(2-oxo-4-phenyl-chromen-7-yl)oxyacetate | + | |
| 45 | 6-chloro-7-(2-morpholino-2-oxo-ethoxy)-4-phenyl-chromen-2-one | (+) | |
| 46 | 2-(6-chloro-2-oxo-4-phenyl-chromen-7-yl)oxy-N-cyclopropyl-acetamide | + | |
| 47 | 2-(6-chloro-2-oxo-4-phenyl-chromen-7-yl)oxy-N,N-diethyl-acetamide | + | |
| 48 | N,N-diethyl-2-(2-oxo-4-phenyl-chromen-7-yl)oxy-acetamide | (+) | |
| 49 | ethyl 2-(6-chloro-2-oxo-4-phenyl-chromen-7-yl)oxyacetate | + | |
| 50 | ethyl 2-(6-chloro-2-oxo-4-phenyl-chromen-7-yl)oxypropanoate | + | |
| 51 | 2-(2-oxo-4-phenyl-chromen-7-yl)oxypropanoic acid | + | |
| 52 | ethyl 2-(2-oxo-4-phenyl-chromen-7-yl)oxypropanoate | + | + |
| 53 | isopropyl 2-(2-oxo-4-phenyl-chromen-7-yl)oxypropanoate | ++ | +++ |
| 54 | 1-[2-(2-oxo-4-phenyl-chromen-7-yl)oxyacetyl]piperidine-3-carboxylic acid | + | |
| 55 | 2-(2-oxo-4-phenyl-chromen-7-yl)oxy-N-(3-pyridyl)propanamide | (+) | |
| 56 | methyl 2-(2-oxo-4-phenyl-chromen-7-yl)oxypropanoate | + | |
| 57 | 2-(6-chloro-2-oxo-4-phenyl-chromen-7-yl)oxy-N-[4-(2-hydroxyethyl)phenyl]acetamide | + | |
| 58 | methyl 2-(6-chloro-2-oxo-4-phenyl-chromen-7-yl)oxypropanoate | + | |
| 59 | 2-(6-chloro-2-oxo-4-phenyl-chromen-7-yl)oxy-N-(3-pyridylmethyl)acetamide | (+) | |
| 60 | 1-[2-(2-oxo-4-phenyl-chromen-7-yl)oxypropanoyl]piperidine-3-carboxamide | (+) | |
| 61 | 2-(2-oxo-4-phenyl-chromen-7-yl)oxy-N-(4-pyridyl)propanamide | (+) | |
| 62 | N-methyl-1-[2-(2-oxo-4-phenyl-chromen-7-yl)oxypropanoyl]piperidine-3-carboxamide | (+) | |
| 63 | methyl 1-[2-(2-oxo-4-phenyl-chromen-7-yl)oxypropanoyl]piperidine-4-carboxylate | (+) | |
| 64 | ethyl rac-(3S)-1-[2-(2-oxo-4-phenyl-chromen-7-yl)oxypropanoyl]piperidine-3-carboxylate | (+) | |
| 65 | ethyl 2-[4-(4-methoxyphenyl)-2-oxo-chromen-7-yl]oxypropanoate | (+) | (+) |
| 66 | (2R)-2-(2-oxo-4-phenyl-chromen-7-yl)oxypropanoic acid | (+) | |
| 67 | 2-(2-oxo-4-phenyl-chromen-7-yl)oxypropanamide | (+) | |
| 68 | rac-(3S)-N,N-dimethyl-1-[2-(2-oxo-4-phenyl-chromen-7-yl)oxpropanoyl]piperidine-3-carboxamide | (+) | |
| 69 | 1-[2-(2-oxo-4-phenyl-chromen-7-yl)oxypropanoyl]piperidine-4-carboxylic acid | (+) | |
| 70 | N-(2-morpholinoethyl)-2-(2-oxo-4-phenyl-chromen-7-yl)oxy-propanamide | (+) | |
| 71 | ethyl 2-(2-oxo-4-phenyl-chromen-7-yl)oxybutanoate | (+) | |
| 72 | N-(4-methoxyphenyl)-2-(2-oxo-4-phenyl-chromen-7-yl)oxy-propanamide | (+) | |
| 73 | 2-ethoxyethyl 2-(2-oxo-4-phenyl-chromen-7-yl)oxyacetate | (+) | |
| 74 | propyl 2-(2-oxo-4-phenyl-chromen-7-yl)oxyacetate | (+) | |
| 75 | 2-(2-oxo-4-phenyl-chromen-7-yl)oxyacetamide | (+) | |
| 76 | butyl 2-(2-oxo-4-phenyl-chromen-7-yl)oxyacetate | (+) | |
| 77 | isobutyl 2-(2-oxo-4-phenyl-chromen-7-yl)oxyacetate | (+) | |
| 78 | 6-chloro-7-[2-(3,4-dihydro-2H-quinolin-1-yl)-2-oxo-ethoxy]-4-phenyl-chromen-2-one | (+) | |
| 79 | 2-(6-chloro-2-oxo-4-phenyl-chromen-7-yl)oxy-N-(2-morpholinoethyl)propanamide | (+) | |
| 80 | 2-(5-fluoro-2-oxo-4-phenyl-chromen-7-yl)oxy-N,N-dimethyl-propanamide | (+) | |
| 81 | ethyl 2-(2-oxo-4-phenyl-chromen-7-yl)oxyacetate | (+) | |
| 82 | tert-butyl 2-(6-chloro-2-oxo-4-phenyl-chromen-7-yl)oxyacetate | (+) | |
| 83 | 2-(6-chloro-2-oxo-4-phenyl-chromen-7-yl)oxy-N-(2-morpholinoethyl)acetamide | (+) | |
| 84 | 2-(6-chloro-2-oxo-4-phenyl-chromen-7-yl)oxyacetamide | (+) | |
| 85 | 1-[2-(6-chloro-2-oxo-4-phenyl-chromen-7-yl)oxyacetyl]piperidine-3-carboxylic acid | (+) | |
| 86 | 2-(6-chloro-2-oxo-4-phenyl-chromen-7-yl)oxy-N-cyclooctyl-acetamide | (+) | |
| 87 | ethyl 2-(5-fluoro-2-oxo-4-phenyl-chromen-7-yl)oxypropanoate | (+) | |
| 88 | 2-(6-chloro-2-oxo-4-phenyl-chromen-7-yl)oxyacetic acid | (+) | |

TABLE 3-continued

IUPAC chemical names and biological activities

| IUPAC Name | mitochondrial transcription activity | cellular qPCR assay |
|---|---|---|
| 89 4-[[2-(6-chloro-2-oxo-4-phenyl-chromen-7-yl)oxypropanoylamino]methyl]cyclohexanecarboxylic acid | (+) | |
| 90 2-(6-chloro-2-oxo-4-phenyl-chromen-7-yl)oxy-N-(2-hydroxy-2-phenyl-ethyl)acetamide | (+) | |
| 91 methyl 2-(8-methyl-2-oxo-4-phenyl-chromen-7-yl)oxyacetate | (+) | |
| 92 propyl 2-(6-chloro-2-oxo-4-phenyl-chromen-7-yl)oxyacetate | (+) | |
| 93 benzyl 2-(2-oxo-4-phenyl-chromen-7-yl)oxypropanoate | (+) | |
| 94 tert-butyl 2-(8-methyl-2-oxo-4-phenyl-chromen-7-yl)oxyacetate | (+) | |
| 95 2-(6-chloro-2-oxo-4-phenyl-chromen-7-yl)oxy-N-(1,1-dioxo-2,3-dihydrothiophen-3-yl)acetamide | (+) | |
| 96 2-[2-(2-oxo-4-phenyl-chromen-7-yl)oxypropanoylamino]-2-phenyl-acetic acid | (+) | |
| 97 2-(2-oxo-4-phenyl-6-propyl-chromen-7-yl)oxypropanoic acid | (+) | |
| 98 4-[[[2-(6-chloro-2-oxo-4-phenyl-chromen-7-yl)oxyacetyl]amino]methyl]cyclohexanecarboxylic acid | (+) | |
| 99 2-(6-chloro-2-oxo-4-phenyl-chromen-7-yl)oxy-N-(2-pyridylmethyl)acetamide | (+) | |

LITERATURE

Ariaans, G., et al. (2017). "Anti-tumor effects of everolimus and metformin are complementary and glucose-dependent in breast cancer cells." BMC Cancer 17(1): 232.

Arnold, J. J., et al. (2012). "Human mitochondrial RNA polymerase: structure-function, mechanism and inhibition." Biochim Biophys Acta 1819(9-10): 948-960.

Behera, M. A., et al. (2009). "Progesterone stimulates mitochondrial activity with subsequent inhibition of apoptosis in MCF-10A benign breast epithelial cells." Am J Physiol Endocrinol Metab 297(5): E1089-1096.

Bhat, M., et al. (2013). "The mTOR pathway in hepatic malignancies." Hepatology 58(2): 810-818.

Bralha, F. N., et al. (2015). "Targeting mitochondrial RNA polymerase in acute myeloid leukemia." Oncotarget 6(35): 37216-37228.

Brecht, K., et al. (2017). "Mechanistic insights into selective killing of OXPHOS-dependent cancer cells by arctigenin." Toxicol In Vitro 40: 55-65.

Bubner, B. and I. T. Baldwin (2004). "Use of real-time PCR for determining copy number and zygosity in transgenic plants." Plant Cell Rep 23(5): 263-271.

Caro, P., et al. (2012). "Metabolic signatures uncover distinct targets in molecular subsets of diffuse large B cell lymphoma." Cancer Cell 22(4): 547-560.

Carroll, S. S., et al. (2003). "Inhibition of hepatitis C virus RNA replication by 2'-modified nucleoside analogs." J Biol Chem 278(14): 11979-11984.

Denise. C., et al. (2015). "5-fluorouracil resistant colon cancer cells are addicted to OXPHOS to survive and enhance stem-like traits." Oncotarget 6(39): 41706-41721.

Dörr, J. R., et al. (2013). "Synthetic lethal metabolic targeting of cellular senescence in cancer therapy." Nature 501(7467): 421-425.

Falkenberg, M., et al. (2002). "Mitochondrial transcription factors B1 and B2 activate transcription of human mtDNA." Nat Genet 31(3): 289-294.

Fulda, S., et al. (2010). "Targeting mitochondria for cancer therapy." Nat Rev Drug Discov 9(6): 447-464.

Gosselin, F., et al. (2010). "A practical synthesis of 5-lipoxygenase inhibitor MK-0633." J Org Chem 75(12): 4154-4160.

Haq, R., et al. (2013). "Oncogenic BRAF regulates oxidative metabolism via PGC1alpha and MITF." Cancer Cell 23(3): 302-315.

Haynes, D. A., et al. (2005). "Occurrence of pharmaceutically acceptable anions and cations in the Cambridge Structural Database." Journal of Pharmaceutical Sciences 94(10): 2111-2120.

Heid, C. A., et al. (1996). "Real time quantitative PCR." Genome Res 6(10): 986-994.

Hsu, P. P. and D. M. Sabatini (2008). "Cancer cell metabolism: Warburg and beyond." Cell 134(5): 703-707.

Klomp, J. A., et al. (2010). "Birt-Hogg-Dube renal tumors are genetically distinct from other renal neoplasias and are associated with up-regulation of mitochondrial gene expression." BMC Med Genomics 3: 59.

Leonetti, F., et al. (2004). "Design, synthesis, and 3D QSAR of novel potent and selective aromatase inhibitors." J Med Chem 47(27): 6792-6803.

Ling, S., et al. (2017). "Combination of metformin and sorafenib suppresses proliferation and induces autophagy of hepatocellular carcinoma via targeting the mTOR pathway." Int J Oncol 50(1): 297-309.

Mitsunobu, O. and M. Yamada (1967). "Preparation of Esters of Carboxylic and Phosphoric Acid via Quaternary Phosphonium Salts." Bulletin of the Chemical Society of Japan 40(10): 2380-2382.

Nadji. M., et al. (2005). "Immunohistochemistry of estrogen and progesterone receptors reconsidered: experience with 5,993 breast cancers." Am J Clin Pathol 123(1): 21-27.

Pelicano, H., et al. (2006). "Glycolysis inhibition for anticancer treatment." Oncogene 25(34): 4633-4646.

Pelicano, H., et al. (2014). "Mitochondrial dysfunction in some triple-negative breast cancer cell lines: role of mTOR pathway and therapeutic potential." Breast Cancer Res 16(5): 434.

Posse, V., et al. (2015). "TEFM is a potent stimulator of mitochondrial transcription elongation in vitro." Nucleic Acids Res 43(5): 2615-2624.

Rodrigues, M. F., et al. (2016). "Enhanced OXPHOS, glutaminolysis and beta-oxidation constitute the metastatic phenotype of melanoma cells." Biochem J 473(6): 703-715.

Rodriguez-Enriquez, S., et al. (2015). "Mitochondrial free fatty acid beta-oxidation supports oxidative phosphorylation and proliferation in cancer cells." Int J Biochem Cell Biol 65: 209-221.

Roesch, A., et al. (2013). "Overcoming intrinsic multidrug resistance in melanoma by blocking the mitochondrial respiratory chain of slow-cycling JARID1B(high) cells." Cancer Cell 23(6): 811-825.

Salem. A. F., et al. (2012). "Two-compartment tumor metabolism: autophagy in the tumor microenvironment and oxidative mitochondrial metabolism (OXPHOS) in cancer cells." Cell Cycle 11(13): 2545-2556.

Sanchez-Alvarez. R., et al. (2013). "Mitochondrial dysfunction in breast cancer cells prevents tumor growth: understanding chemoprevention with metformin." Cell Cycle 12(1): 172-182.

Scarpulla, R. C. (2008). "Transcriptional paradigms in mammalian mitochondrial biogenesis and function." Physiol Rev 88(2): 611-638.

Scatena, R., et al. (2008). "Glycolytic enzyme inhibitors in cancer treatment." *Expert Opin Investig Drugs* 17(10): 1533-1545.

Schöckel, L., et al. (2015). "Targeting mitochondrial complex I using BAY 87-2243 reduces melanoma tumor growth." *Cancer Metab* 3: 11.

Sharma, D., et al. (2013). "Cyclohexyl iodide promoted approach for coumarin analog synthesis using small scaffold." *Mol Divers* 17(4): 651-659.

Siegel, R. L., et al. (2016). "Cancer statistics, 2016." *CA Cancer J Clin* 66(1): 7-30.

Tisdale, M. J. (2002). "Cachexia in cancer patients." *Nat Rev Cancer* 2(11): 862-871.

Vander Heiden, M. G., et al. (2009). "Understanding the Warburg effect: the metabolic requirements of cell proliferation." *Science* 324(5930): 1029-1033.

Waiters. W. P. and M. Namchuk (2003). "Designing screens: how to make your hits a hit." *Nat Rev Drug Discov* 2(4): 259-266.

Wanrooij, S. and M. Falkenberg (2010). "The human mitochondrial replication fork in health and disease." *Biochim Biophys Acta* 1797(8): 1378-1388.

Weinberg, S. E. and N. S. Chandel (2015). "Targeting mitochondria metabolism for cancer therapy." *Nat Chem Biol* 11(1): 9-15.

Whitaker-Menezes, D., et al. (2011). "Evidence for a stromal-epithelial "lactate shuttle" in human tumors: MCT4 is a marker of oxidative stress in cancer-associated fibroblasts." *Cell Cycle* 10(11): 1772-1783.

Yeung, K. Y., et al. (2014). "The identification of mitochondrial DNA variants in glioblastoma multiforme." *Acta Neuropathol Commun* 2: 1.

WO 2008/054475 A2
WO 2016/146583 A1
WO 2016/193231 A1

The invention claimed is:

1. A method of inhibiting POLRMT comprising administering a therapeutically effective amount of a compound of the general formula (I)

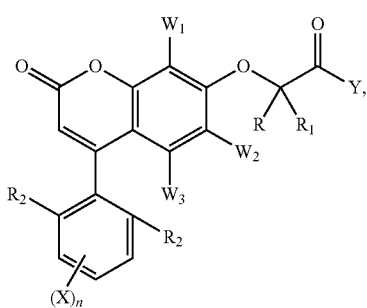

wherein
R is —H or —$C_1$-$C_4$-alkyl;
$R_1$ is —H or -methyl;
$R_2$ is —H;
n=0, 1 or 2;
X is -halogen, —$C_1$-$C_4$-alkyl, —OMe or —CN, with n=1 or 2;
Y is —$NR_3R_4$ with
  $R_3$ is —H, or —$C_1$-$C_4$-alkyl, and
  $R_4$ is —H, —$C_1$-$C_4$-alkyl or —$C_3$-$C_8$-cycloalkyl;
  an unsubstituted or substituted pyridine residue;
  an unsubstituted or substituted pyridinylmethyl residue;
  an unsubstituted or substituted morpholinylethyl residue;
  an unsubstituted or substituted furanylmethyl residue;
  an unsubstituted or substituted phenyl residue;
  an unsubstituted or substituted benzyl residue;
  an unsubstituted or substituted phenethyl residue;
  the group;

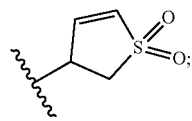 [SMILES: *C1C=CS(=O)(=O)C1]

or
the group

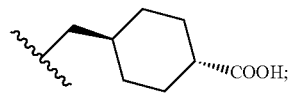 [SMILES: *C[C@H]1CC[C@H](C(=O)O)CC1]

or
Y is —$NR_3R_4$ with N, $R_3$ and $R_4$ forming an unsubstituted or substituted 5- or 6-membered saturated heterocycle,

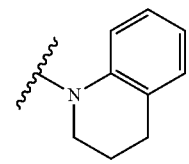 [SMILES: *N1CCCc2ccccc21]

or
Y is —$OR_{11}$, with $R_{11}$ is —H or —$C_1$-$C_4$-alkyl, phenyl, benzyl or 2-ethoxyethyl; and
$W_1$, $W_2$, and $W_3$ are identical or different, and are —H, -halogen, or —$C_1$-$C_4$-alkyl;
or a pharmaceutically or veterinary acceptable salt, hydrate or solvate thereof
to a patient in need thereof.

2. The method of claim 1, wherein
R is —H, -methyl or -ethyl;
$R_1$ is —H;
$R_2$ is —H;
n=0 or 1, preferably n=0;
X is -halogen, —$C_1$-$C_4$-alkyl, —OMe or —CN, with n=1;
Y is —$NR_3R_4$ with
  $R_3$ is —H, or —$C_1$-$C_4$-alkyl, preferably —H or -methyl, and
  $R_4$ is —H, —$C_1$-$C_4$-alkyl or —$C_3$-$C_8$-cycloalkyl;
  an unsubstituted or substituted pyridine residue;
  an unsubstituted or substituted pyridinylmethyl residue;
  an unsubstituted or substituted morpholinylethyl residue;
  an unsubstituted or substituted furanylmethyl residue;
  an unsubstituted or substituted phenyl residue;
  an unsubstituted or substituted benzyl residue;
  an unsubstituted or substituted phenethyl residue;

the group

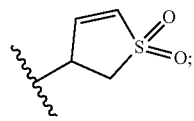 [SMILES: *C1C=CS(=O)(=O)C1]

or
the group

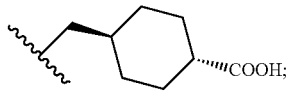 [SMILES: *C[C@H]1CC[C@H](C(=O)O)CC1]

or
Y is —NR₃R₄ with N, R₃ and R₄ forming an unsubstituted or substituted 5- or 6-membered saturated heterocycle,

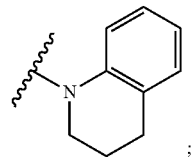 [SMILES: *N1CCCc2ccccc21 ; ";"]

or
Y is —OR₁₁, with R₁₁ is —H or —C₁-C₄-alkyl, phenyl, benzyl or 2-ethoxyethyl; and
W₁, W₂, and W₃ are identical or different, and are —H, -halogen, or —C₁-C₄-alkyl.

3. The method of claim 1, wherein
R is —H or -methyl;
R₁ is —H; and
W₁, W₂, and W₃ are identical or different, and are —H or —Cl.

4. The method of claim 1, wherein
W₁, W₂, and W₃ are identical and are —H.

5. The method of claim 1, wherein W₁ and W₃ are identical and are —H; and W₂ is —Cl.

6. The method of claim 1, wherein
R is -methyl; and
R₁ is —H.

7. The method of claim 1, wherein
R is —H and
R₁ is —H.

8. The method of claim 1, wherein
n=1; and
X is -halogen.

9. The method of claim 1, wherein
n=0, 1 or 2, preferably 0, or
X is -halogen, or —CN, with n=1 or 2;
Y is —NR₃R₄ with
R₃ is —H, or —C₁-C₄-alkyl, and
R₄ is —C₁-C₄-alkyl or —C₃-C₆-cycloalkyl; or
an unsubstituted or substituted pyridine residue; or
an unsubstituted or substituted phenyl residue;
Y is —NR₃R₄ with N, R₃ and R₄ forming an unsubstituted or substituted 5- or 6-membered saturated heterocycle; or
Y is —OR₁₁, with R₁₁ is —H or —C₁-C₄-alkyl.

10. The method of claim 1, wherein the compound of formula (I) is selected from tert-butyl 2-(2-oxo-4-phenyl-chromen-7-yl)oxypropanoate
N,N-dimethyl-2-(2-oxo-4-phenyl-chromen-7-yl)oxy-propanamide
ethyl 2-[4-(4-chlorophenyl)-2-oxo-chromen-7-yl]oxypropanoate
ethyl 2-[4-(3-chlorophenyl)-2-oxo-chromen-7-yl]oxypropanoate
N-[4-(3-hydroxypropyl)phenyl]-2-(2-oxo-4-phenyl-chromen-7-yl)oxy-propanamide
2-(2-oxo-4-phenyl-chromen-7-yl)oxy-N-(2-pyridyl)propanamide
ethyl 2-[4-(3-fluorophenyl)-2-oxo-chromen-7-yl]oxypropanoate
ethyl 2-[4-(4-fluorophenyl)-2-oxo-chromen-7-yl]oxypropanoate
ethyl 2-[2-oxo-4-(p-tolyl)chromen-7-yl]oxypropanoate
methyl 1-[2-(6-chloro-2-oxo-4-phenyl-chromen-7-yl)oxypropanoyl]piperidine-3-carboxylate
2-(6-chloro-2-oxo-4-phenyl-chromen-7-yl)oxy-N-(2-pyridyl)propanamide
N-isopropyl-2-(2-oxo-4-phenyl-chromen-7-yl)oxy-propanamide
1-[2-(6-chloro-2-oxo-4-phenyl-chromen-7-yl)oxypropanoyl]piperidine-3-carboxylic acid
1-[2-(2-oxo-4-phenyl-chromen-7-yl)oxypropanoyl]piperidine-3-carboxylic acid
methyl 1-[2-(2-oxo-4-phenyl-chromen-7-yl)oxypropanoyl]piperidine-3-carboxylate
N-[4-(2-hydroxyethyl)phenyl]-2-(2-oxo-4-phenyl-chromen-7-yl)oxy-propanamide
2-(6-chloro-2-oxo-4-phenyl-chromen-7-yl)oxy-N-[4-(2-hydroxyethyl)phenyl]propanamide
N-[4-(2-hydroxyethyl)phenyl]-N-methyl-2-(2-oxo-4-phenyl-chromen-7-yl)oxy-propanamide
1-[2-(2-oxo-4-phenyl-chromen-7-yl)oxypropanoyl]piperidine-3-carbonitrile
7-[1-methyl-2-oxo-2-[3-(2H-tetrazol-5-yl)-1-piperidyl]ethoxy]-4-phenyl-chromen-2-one
(3S)-1-[(2R)-2-(2-oxo-4-phenyl-chromen-7-yl)oxypropanoyl]piperidine-3-carboxylic acid
2-(2-oxo-4-phenyl-chromen-7-yl)oxy-N-(2-pyridyl)acetamide
methyl 1-[2-(2-oxo-4-phenyl-chromen-7-yl)oxyacetyl]piperidine-3-carboxylate
phenyl 2-(2-oxo-4-phenyl-chromen-7-yl)oxypropanoate
2-(2-oxo-4-phenyl-chromen-7-yl)oxy-N-phenyl-propanamide
N-methyl-2-(2-oxo-4-phenyl-chromen-7-yl)oxy-propanamide
2-(6-chloro-2-oxo-4-phenyl-chromen-7-yl)oxy-N-(2-hydroxy-2-phenyl-ethyl)propanamide
2-(6-chloro-2-oxo-4-phenyl-chromen-7-yl)oxy-N-[4-(3-hydroxypropyl)phenyl]propanamide
N-(2-hydroxy-2-phenyl-ethyl)-2-(2-oxo-4-phenyl-chromen-7-yl)oxy-propanamide
N-ethyl-2-(2-oxo-4-phenyl-chromen-7-yl)oxy-propanamide
7-(1-methyl-2-oxo-2-pyrrolidin-1-yl-ethoxy)-4-phenyl-chromen-2-one
ethyl 2-methyl-2-(2-oxo-4-phenyl-chromen-7-yl)oxypropanoate
ethyl (2R)-2-(2-oxo-4-phenyl-chromen-7-yl)oxypropanoate
(2R)—N,N-dimethyl-2-(2-oxo-4-phenyl-chromen-7-yl)oxy-propanamide ethyl (3S)-1-[(2R)-2-(2-oxo-4-phenyl-chromen-7-yl)oxy-propanoyl]piperidine-3-carboxylate
(3S)-1-[2-(2-oxo-4-phenyl-chromen-7-yl)oxypropanoyl]piperidine-3-carboxylic acid
(3R)-1-[2-(2-oxo-4-phenyl-chromen-7-yl)oxypropanoyl]piperidine-3-carboxylic acid
methyl (3R)-1-[2-(2-oxo-4-phenyl-chromen-7-yl)oxypropanoyl]piperidine-3-carboxylate
7-[1-methyl-2-oxo-2-(1-piperidyl)ethoxy]-4-phenyl-chromen-2-one
N-[4-(2-hydroxyethyl)phenyl]-N-methyl-2-(2-oxo-4-phenyl-chromen-7-yl)oxy-acetamide
ethyl 2-[4-(4-bromophenyl)-2-oxo-chromen-7-yl]oxypropanoate
2-(6-chloro-2-oxo-4-phenyl-chromen-7-yl)oxy-N-(2-furylmethyl)propanamide
ethyl 1-[2-(2-oxo-4-phenyl-chromen-7-yl)oxyacetyl]piperidine-3-carboxylate
tert-butyl 2-(2-oxo-4-phenyl-chromen-7-yl)oxyacetate
6-chloro-7-(2-morpholino-2-oxo-ethoxy)-4-phenyl-chromen-2-one
2-(6-chloro-2-oxo-4-phenyl-chromen-7-yl)oxy-N-cyclopropyl-acetamide
2-(6-chloro-2-oxo-4-phenyl-chromen-7-yl)oxy-N,N-diethyl-acetamide
N,N-diethyl-2-(2-oxo-4-phenyl-chromen-7-yl)oxy-acetamide
ethyl 2-(6-chloro-2-oxo-4-phenyl-chromen-7-yl)oxyacetate
ethyl 2-(6-chloro-2-oxo-4-phenyl-chromen-7-yl)oxypropanoate
2-(2-oxo-4-phenyl-chromen-7-yl)oxypropanoic acid
ethyl 2-(2-oxo-4-phenyl-chromen-7-yl)oxypropanoate
isopropyl 2-(2-oxo-4-phenyl-chromen-7-yl)oxypropanoate
1-[2-(2-oxo-4-phenyl-chromen-7-yl)oxyacetyl]piperidine-3-carboxylic acid
2-(2-oxo-4-phenyl-chromen-7-yl)oxy-N-(3-pyridyl)propanamide
methyl 2-(2-oxo-4-phenyl-chromen-7-yl)oxypropanoate
2-(6-chloro-2-oxo-4-phenyl-chromen-7-yl)oxy-N-[4-(2-hydroxyethyl)phenyl]acetamide
methyl 2-(6-chloro-2-oxo-4-phenyl-chromen-7-yl)oxypropanoate
2-(6-chloro-2-oxo-4-phenyl-chromen-7-yl)oxy-N-(3-pyridylmethyl)acetamide
1-[2-(2-oxo-4-phenyl-chromen-7-yl)oxypropanoyl]piperidine-3-carboxamide
2-(2-oxo-4-phenyl-chromen-7-yl)oxy-N-(4-pyridyl)propanamide
N-methyl-1-[2-(2-oxo-4-phenyl-chromen-7-yl)oxypropanoyl]piperidine-3-carboxamide
methyl 1-[2-(2-oxo-4-phenyl-chromen-7-yl)oxypropanoyl]piperidine-4-carboxylate
ethyl rac-(3S)-1-[2-(2-oxo-4-phenyl-chromen-7-yl)oxypropanoyl]piperidine-3-carboxylate
ethyl 2-[4-(4-methoxyphenyl)-2-oxo-chromen-7-yl]oxypropanoate
(2R)-2-(2-oxo-4-phenyl-chromen-7-yl)oxypropanoic acid
2-(2-oxo-4-phenyl-chromen-7-yl)oxypropanamide
rac-(3S)—N,N-dimethyl-1-[2-(2-oxo-4-phenyl-chromen-7-yl)oxypropanoyl]piperidine-3-carboxamide
1-[2-(2-oxo-4-phenyl-chromen-7-yl)oxypropanoyl]piperidine-4-carboxylic acid
N-(2-morpholinoethyl)-2-(2-oxo-4-phenyl-chromen-7-yl)oxy-propanamide
ethyl 2-(2-oxo-4-phenyl-chromen-7-yl)oxybutanoate
N-(4-methoxyphenyl)-2-(2-oxo-4-phenyl-chromen-7-yl)oxy-propanamide
2-ethoxyethyl 2-(2-oxo-4-phenyl-chromen-7-yl)oxyacetate
propyl 2-(2-oxo-4-phenyl-chromen-7-yl)oxyacetate
2-(2-oxo-4-phenyl-chromen-7-yl)oxyacetamide
butyl 2-(2-oxo-4-phenyl-chromen-7-yl)oxyacetate
isobutyl 2-(2-oxo-4-phenyl-chromen-7-yl)oxyacetate
6-chloro-7-[2-(3,4-dihydro-2H-quinolin-1-yl)-2-oxo-ethoxy]-4-phenyl-chromen-2-one
2-(6-chloro-2-oxo-4-phenyl-chromen-7-yl)oxy-N-(2-morpholinoethyl)propanamide
2-(5-fluoro-2-oxo-4-phenyl-chromen-7-yl)oxy-N,N-dimethyl-propanamide
ethyl 2-(2-oxo-4-phenyl-chromen-7-yl)oxyacetate
tert-butyl 2-(6-chloro-2-oxo-4-phenyl-chromen-7-yl)oxyacetate
2-(6-chloro-2-oxo-4-phenyl-chromen-7-yl)oxy-N-(2-morpholinoethyl)acetamide
2-(6-chloro-2-oxo-4-phenyl-chromen-7-yl)oxyacetamide
1-[2-(6-chloro-2-oxo-4-phenyl-chromen-7-yl)oxyacetyl]piperidine-3-carboxylic acid
2-(6-chloro-2-oxo-4-phenyl-chromen-7-yl)oxy-N-cyclooctyl-acetamide
ethyl 2-(5-fluoro-2-oxo-4-phenyl-chromen-7-yl)oxypropanoate
2-(6-chloro-2-oxo-4-phenyl-chromen-7-yl)oxyacetic acid
4-[[2-(6-chloro-2-oxo-4-phenyl-chromen-7-yl)oxypropanoylamino]methyl]cyclohexanecarboxylic acid
2-(6-chloro-2-oxo-4-phenyl-chromen-7-yl)oxy-N-(2-hydroxy-2-phenyl-ethyl)acetamide
methyl 2-(8-methyl-2-oxo-4-phenyl-chromen-7-yl)oxyacetate
propyl 2-(6-chloro-2-oxo-4-phenyl-chromen-7-yl)oxyacetate
benzyl 2-(2-oxo-4-phenyl-chromen-7-yl)oxypropanoate
tert-butyl 2-(8-methyl-2-oxo-4-phenyl-chromen-7-yl)oxyacetate
2-(6-chloro-2-oxo-4-phenyl-chromen-7-yl)oxy-N-(1,1-dioxo-2,3-dihydrothiophen-3-yl)acetamide
2-[2-(2-oxo-4-phenyl-chromen-7-yl)oxypropanoylamino]-2-phenyl-acetic acid
2-(2-oxo-4-phenyl-6-propyl-chromen-7-yl)oxypropanoic acid
4-[[[2-(6-chloro-2-oxo-4-phenyl-chromen-7-yl)oxyacetyl]amino]methyl]cyclohexanecarboxylic acid
2-(6-chloro-2-oxo-4-phenyl-chromen-7-yl)oxy-N-(2-pyridylmethyl)acetamide, or a pharmaceutically or veterinary acceptable salt, hydrate or solvate thereof.

11. A method of treating cancer by inhibiting POLRMT comprising administering a therapeutically effective amount of a compound of the general formula (I)

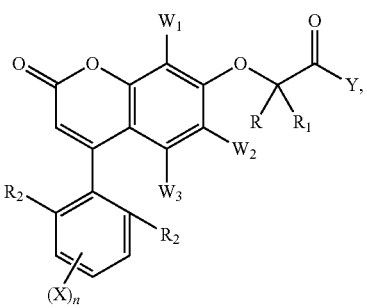 (I)

wherein
R is —H or —$C_1$-$C_4$-alkyl;
$R_1$ is —H or -methyl;
$R_2$ is —H;
n=0, 1 or 2;
X is -halogen, —$C_1$-$C_4$-alkyl, —OMe or —CN, with n=1 or 2;
Y is —$NR_3R_4$ with
  $R_3$ is —H, or —$C_1$-$C_4$-alkyl, and
  $R_4$ is —H, —$C_1$-$C_4$-alkyl or —$C_3$-$C_8$-cycloalkyl;
an unsubstituted or substituted pyridine residue;
an unsubstituted or substituted pyridinylmethyl residue;
an unsubstituted or substituted morpholinylethyl residue;
an unsubstituted or substituted furanylmethyl residue;
an unsubstituted or substituted phenyl residue;
an unsubstituted or substituted benzyl residue;
an unsubstituted or substituted phenethyl residue;
the group

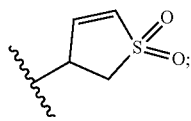

or the group

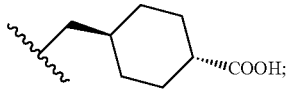

or
Y is —$NR_3R_4$ with N, $R_3$ and $R_4$ forming an unsubstituted or substituted 5- or 6-membered saturated heterocycle,

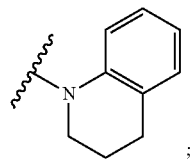 [SMILES: *N1CCCc2ccccc21 ; ";"];

or
Y is —$OR_1$, with $R_{11}$ is —H or —$C_1$-$C_4$-alkyl, phenyl, benzyl or 2-ethoxyethyl; and
$W_1$, $W_2$, and $W_3$ are identical or different, and are —H, -halogen, or —$C_1$-$C_4$-alkyl;
or a pharmaceutically or veterinary acceptable salt, hydrate or solvate thereof
to a patient in need thereof.

12. The method of claim 11, wherein the cancer is selected from the group consisting of melanoma, metastatic melanoma, pancreatic cancer, hepatocellular carcinoma, lymphoma, acute myeloid leukemia, breast cancer, glioblastoma, cervical cancer, renal cancer, colorectal cancer and ovarian cancer.

13. The method of claim 11, wherein the method is carried out in simultaneous, alternating or subsequent combination with a second cancer therapy.

14. The method of claim 13, wherein the second cancer therapy is selected from the group consisting of chemotherapy, immunotherapy, hormone therapy, stem cell transplantation therapy, radiation therapy and surgery.

* * * * *